United States Patent
Laine et al.

(10) Patent No.: US 11,613,513 B2
(45) Date of Patent: Mar. 28, 2023

(54) ORGANIC MATERIALS WITH SPECIAL OPTICAL EFFECTS

(71) Applicants: Centre National de la Recherche Scientifique (CNRS), Paris (FR); Universite Paris Diderot Paris 7, Paris (FR)

(72) Inventors: Philippe Laine, Paris (FR); Laurélie Poulard, Aulnay-sous-Bois (FR); Grégory Dupeyre, La Queue en Brie (FR)

(73) Assignees: Centre National de la Recherche Scientifique (CNRS), Paris (FR); Université Paris Cité, Paris (FR)

( * ) Notice: Subject to any disclaimer, the term of this patent is extended or adjusted under 35 U.S.C. 154(b) by 0 days.

(21) Appl. No.: 16/473,782

(22) PCT Filed: Dec. 28, 2017

(86) PCT No.: PCT/EP2017/084782
§ 371 (c)(1),
(2) Date: Jun. 26, 2019

(87) PCT Pub. No.: WO2018/122359
PCT Pub. Date: Jul. 5, 2018

(65) Prior Publication Data
US 2019/0337885 A1 Nov. 7, 2019

(30) Foreign Application Priority Data
Dec. 29, 2016 (EP) .................................... 16306849

(51) Int. Cl.
| | | |
|---|---|---|
| *C07C 211/50* | (2006.01) |
| *C07C 43/205* | (2006.01) |
| *C07C 211/52* | (2006.01) |
| *C07C 217/76* | (2006.01) |
| *C07C 217/84* | (2006.01) |
| *C07C 217/92* | (2006.01) |
| *C07C 217/94* | (2006.01) |
| *C07C 255/53* | (2006.01) |
| *C07D 209/88* | (2006.01) |
| *C07D 295/135* | (2006.01) |
| *C07D 471/04* | (2006.01) |
| *C07F 7/08* | (2006.01) |
| *C09B 11/02* | (2006.01) |
| *C09B 11/06* | (2006.01) |
| *C09B 11/12* | (2006.01) |
| *C09B 11/22* | (2006.01) |
| *C09B 11/28* | (2006.01) |
| *C09B 57/00* | (2006.01) |
| *C07F 9/535* | (2006.01) |

(52) U.S. Cl.
CPC ........ *C07C 211/50* (2013.01); *C07C 43/2055* (2013.01); *C07C 211/52* (2013.01); *C07C 217/76* (2013.01); *C07C 217/84* (2013.01); *C07C 217/92* (2013.01); *C07C 217/94* (2013.01); *C07C 255/53* (2013.01); *C07D 209/88* (2013.01); *C07D 295/135* (2013.01); *C07D 471/04* (2013.01); *C07F 7/08* (2013.01); *C07F 9/535* (2013.01); *C09B 11/02* (2013.01); *C09B 11/06* (2013.01); *C09B 11/12* (2013.01); *C09B 11/22* (2013.01); *C09B 11/28* (2013.01); *C09B 57/008* (2013.01)

(58) Field of Classification Search
CPC ... C07C 211/50; C07C 211/52; C07C 217/76; C07C 217/84; C07C 217/92; C07C 217/94; C07C 43/2055; C07C 255/53; C07D 209/88; C07D 295/135; C07D 471/04; C07F 7/08; C07F 9/535; C09B 11/02; C09B 11/06; C09B 11/12; C09B 11/22; C09B 11/28
See application file for complete search history.

(56) References Cited

FOREIGN PATENT DOCUMENTS

JP          10035107       *   2/1998   ............. B41M 5/26

OTHER PUBLICATIONS

Database CA [Online] Chemical Abstracts Service, Columbus, Ohio, US; Wada, Masanori et al. Unusual Stabilities and Reactivities of Tris- and Bis(2,4,6-trimethoxyphenyl)carbenium Salts, XP002769628, retrievec rom STN Database accession No. 1997:719517 abstract. 1997.*
Database CA [Online] Chemical Abstracts Service, Columbus, Ohio, US; Wada, Masanori et al. "Unusual Stabilities and Reactivities of Tris- and Bis(2,4,6-trimethoxyphenyl)carbenium Salts", XP002769628, retrieved from STN Database accession No. 1997:719517 abstract.

(Continued)

Primary Examiner — Amina S Khan
(74) Attorney, Agent, or Firm — Banner & Witcoff, Ltd.

(57) ABSTRACT

The present invention relates to a compound of the following formula (I). The invention also relates to uses thereof as a chromophore as such or for building pigments displaying special optical effects, including metal-like reflection.

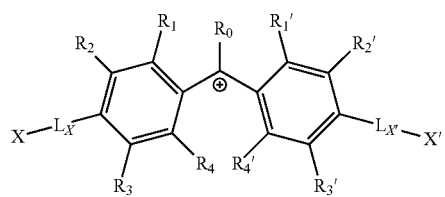

(I)

7 Claims, 13 Drawing Sheets

(56) References Cited

OTHER PUBLICATIONS

Figure 1:
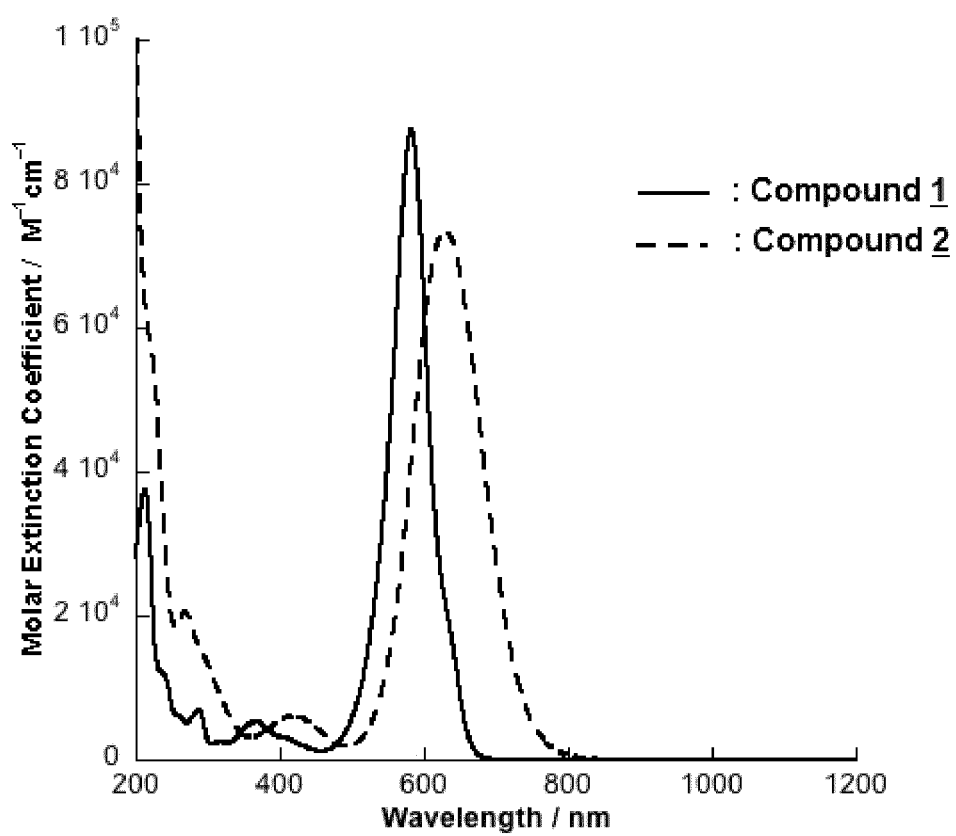

Wada et al. "Unusual Stabilities and Reactivities of Tris- and Bis(2,4,6-trimethoxyphenyl)carbenium salts". Bull. Chem Soc. Jpn., 70, 2737-2741 (1997).
Laursen et al. "2,6,10-Tris(dialkylamino)trioxatriangulenium salts: a new promising fluorophore. Ion-pair formation and aggregation in non-polar solvents". Photochem. Photobiol. Sci. 2005, 4, 568-576.
Kondo et al. "Gold-colored Organic Crystals of an Azobenzene Derivative". Langmuir 2014, 30, 4422-4426.
Evans et al. "(E)-5,5'-Di(thiophen-2-yl)-3,3'-bi [thiophen-3(2H)ylidene]—2,2'-diones-from conspicuous blue impurities to "quasi-metallic" golden-bronze crystals" Org. Biomol. Chem., 2013, 11, 3871-3879.
Mar. 2, 2018 (WO) International Search Report PCT/EP2017/084782.
Olah, George A. "Stable Carbonium Ions in Solution". Science, Jun. 12, 1970, New Series, vol. 168, No. 3937 (Jun. 12, 1970), pp. 1298-1311.
Deno et al. "Carbonium Ions. II. Linear Free Energy Relationships in Arylcarbonium Ion Equilibria". J. Am. Chem. Soc. Jun. 1, 1955, 77, 11, 3051-3054.

\* cited by examiner

ORGANIC MATERIALS WITH SPECIAL OPTICAL EFFECTS

RELATED APPLICATION DATA

The present application is a National Stage Application under 35 U.S.C. 371 of co-pending PCT application number PCT/EP2017/084782 designating the United States and filed Dec. 28, 2017; which claims the benefit of EP application number 16306849.7 and filed Dec. 29, 2016, each of which are hereby incorporated herein by reference in their entireties.

FIELD OF THE INVENTION

The present invention relates to sterically congested, V-shaped diarylcarbenium derivatives (that encompasses triarylcarbenium species comprised of only two main "electroactive arms" so that their overall key V-shaped topology is preserved), as well as their use as molecular chromophores of interest as such (e.g. dye molecules) and as components of pigments displaying special optical effects.

Indeed, said diarylcarbenium derivatives of tunable electronic features can serve as the building blocks of organized organic molecular materials exhibiting special optical properties including (1) metal-like reflection or (2) iridescence or pearl-luster effects, that are referred to as special optical effects that respectively originate from interaction of light with the material surface, in the former case (1), or with the bulk material, in the latter case (2).

BACKGROUND OF THE INVENTION

Carbocations represent key intermediates in organic chemistry that were thoroughly studied by G. A. Olah (Nobel prize laureate 1994), who continuously sought to form persistent types of these species, notably by manipulating them at low temperature in superacidic systems. [Olah, G. A. *Angew. Chem., Int. Ed. Engl.* 1995, 34, 1393-1405]

In this peculiar field of organic chemistry, there exists, however, some stable compounds of the triarylcarbenium type, some of them being of the utmost importance (e.g. for dye implementations), like triarylmethane dyes (methyl violet, malachite green and fuchsine dyes, phenol dyes, Victoria blue dyes) and xanthene dyes that are their bridged counterparts (among which rhodamine and fluorescein, for instance). On the other hand, diarylcarbeniums are usually just stable enough to be spectroscopically studied without being isolated in their pure form. Indeed, these are often generated in situ (in solution) via suitable precursors, and immediately reacted with proper nucleophilic species.

For example, diphenylcarbenium ions have been previously reported in the literature. Notably, Mayr et al. [Mayr et al. *J. Am. Chem. Soc.* 2001, 123(39), 9500-9512] have synthetized analogues of the well-known Michler's Hydrol Blue.

Mayr's diphenylcarbeniums have proved to be very useful reference compounds since they allowed establishing extensive electrophilicity and nucleophilicity scales, in spite of their disputable stability, especially in solution, that precludes any further utilization as such. Indeed, very scarce examples of stable diarylcarbenium have been published hitherto.

Diarylcarbeniums possessing a 3-guaiazulenyl (or azulen-1-yl) group have been synthesized by Takekuma et al. [Takekuma et al. *Tetrahedron* 2007, 63, 12058-12070], whereas Barbero et al. have recently reported the synthesis of bench-stable diarylcarbenium tetrafluoroborates bearing indolyl or pyrrolyl moieties (see [Barbero et al. *J. Org. Chem.* 2012, 77, 4278-4287] and [Barbero et al. *J. Org. Chem.* 2015, 80, 4791-4796]).

Interestingly, Sorensen et al. have described triazatriangulenium tetrafluoroborate salts, which constitute a specific class of triphenylcarbenium ions, which phenyl rings are bound together by means of nitrogen atoms [Sorensen et al. *J. Mater. Chem.* 2012, 22, 4797-4805]. The said triazatriangulenium molecules are electroactive dyes, and self-assemble to form highly ordered supramolecular structures. It has been shown that as an anisotropic polycrystalline thin film structure, they ensure an efficient exciton transport.

Specular reflection of light is generally related to electronic conduction (surface plasmon). However, the development of metal-free, non-conductive, reflective organic molecular materials, relying on excitonic processes would pave the way for a wide variety of applications in a broad spectrum of areas: from reflectors or mirrors to photonics, paints and coatings (including niche implementations for which co-existence of electronic conduction and light reflection is detrimental), security inks, cosmetics, optoelectronics and laser technology, amongst others.

Special effect pigments are nano- or meso-particulate materials that give additional color effects, such as angular color dependence (iridescence, luster) or texture. Also named "luster pigments", these pigments are subdivided in 2 classes: metal effect pigments and pearl luster pigments (see [Special Effect Pigments, G. Pfaff, 2008, $2^{nd}$ Rev. ed., Vincentz Network GmbH & Co. KG, Hannover/Germany] and [Metal Effect Pigments, Fundamentals and Applications, P. Wipling, 2006, Vincentz Network GmbH & Co. KG, Hannover/Germany]).

With the exception of examples of "effect pigments" based on organic structures, amongst which so-called "photonic crystals" mostly encountered in Nature (e.g. guanine platelets isolated from fish scales and certain liquid crystals), the industry of "effect pigments" relies almost exclusively on metallic particles and purposely-structured inorganic materials (e.g. crystalline $HgCl_2$ platelets, lead, arsenic or bismuth salts, platelet-shaped $PbHPO_4$, mica-$TiO_2$ combination, basic lead carbonate, bismuth oxychloride, aluminium platelets coated with $Fe_2O_3$, metal oxide-coated synthetic mica, iron oxides mica, chromium(III) oxide mica, $Al_2O_3$ flakes, $SiO_2$ flakes, borosilicate flakes).

Most of these pigments suffer from environmental and/or durability issues: for instance, mercury, lead, arsenic and chromium are considered to be highly toxic.

Hence, there is a need for organic iridescent/pearlescent pigments, environmentally benign and durable.

Hitherto, by definition, "metallic effect pigment" is a subfamily of the "metallic pigment" group that includes "metal pigments" (consisting of pure metals or metal alloys) and either inorganic or organic color pigments possessing at least one metal atom in their formula. Here we propose to use purely organic molecular materials as "metallic effect pigments".

Although conductive polymers are known to display a metallic luster (see [Tanaka et al. *Bull. Chem. Soc. Jpn.* 1980, 53, 3430-3435], [Morikita et al. *Adv. Mater.* 2001, 13, 1862-1864] and [Yamamoto et al. *Macromolecules* 2003, 36, 4262-4267]), very few low molecular weight materials exhibit such a behavior and none is of any significance for industry. Only scarce examples can be cited from the literature, such as 1-aryl-2-[5-(tricyanoethenyl)-2-thienyl]pyrroles, (E)-5,5'-di(thiophen-2-yl)-3,3'-bi[thiophen-3(2H)- ylidene]-2,2'-diones, bis[4-(2-dimethylaminoethoxy)
phenyl]diazene and a donor-acceptor molecule bearing two
boron(III) diketonate moieties (see [Ogura et al. *Org. Biomol. Chem.* 2003, 1, 3845-3850], [Ogura et al. *Tetrahedron* 2006, 62, 2484-2491], [Evans et al. *Org. Biomol. Chem.* 2013, 11, 3871-3879], [Kondo et al. *Langmuir* 2014, 30, 4422-4426] and [Poon et al. *Angew. Chem. Int. Ed.* 2016, 128, 3711-3715]). Those compounds are resulting from serendipity rather than from a specific molecular design, and most often, they are not fully characterized, including from the standpoint of the rationalization of their unusual optical properties.

Noteworthy, however, is the reported example of a polymeric material based on polyvinyl alcohol (PVA) and doped with J-aggregates of TDBC (5,6-dichloro-2-[[5,6-dichloro-1-ethyl-3-(4-sulphobutyl)-benzimidazol-2-ylidene]-propenyl]-1-ethyl-3-(4-sulphobutyl)benzimidazolium hydroxide, sodium salt), that displays metal-like optical properties (see [Gentile et al. *Nano Lett.* 2014, 14, 2339-2344] and [Gentile et al. *J. Opt.* 2016, 18, 015001]).

Therefore, there is a need for reflective organic materials alternative to inorganic and metal-based compounds. For this purpose, the present invention relies on the self-assembly of specifically-conceived chromophores that feature huge molar extinction coefficients and very sharp absorption bands.

In this context, there exists a strong interest in developing chromophoric building blocks featuring above-mentioned electronic features that are namely new stable diarylcarbenium derivatives of V-shaped topology. Indeed, on the one hand, the individual compounds are interesting by themselves, as highly efficient chromophores. On the other hand, these salts can self-assemble, allowing the formation of anisotropic organic supramolecular materials displaying "special optical effects".

SUMMARY OF THE INVENTION

The present invention relates thus to a compound of the following formula (I):

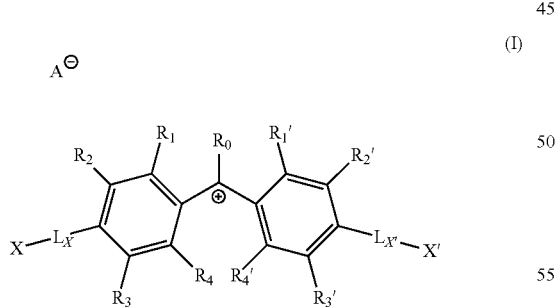

(I)

wherein:

$R_0$ represents a hydrogen atom, a halogen atom, a $(C_1-C_6)$alkyl, $(C_1-C_6)$haloalkyl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_5$, $SR_6$, $NR_7R_8$, $PR_9R_{10}$, $COR_{11}$, $CO_2R_{12}$, $CONR_{13}R_{14}$, $SO_2R_{15}$, $SO_3H$, CN, $NO_2$, $OCOR_{16}$, $OCO_2R_{17}$, $NR_{18}COR_{19}$ or $NR_{20}SO_2R_{21}$ group, or is selected from the group consisting of:

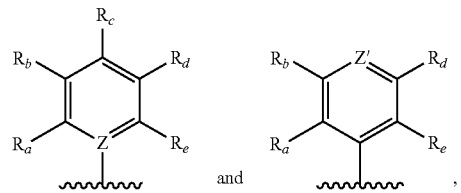

and wherein:

Z represents C or $N^+$ $A_z^-$ and Z' represents N or $N^+$—$R_c'$ $A_z^-$, wherein $A_z^-$ represents a monovalent organic or inorganic anion, and $R_c'$ represents a hydrogen atom or a $(C_1-C_6)$alkyl group, $R_a$ and $R_e$ each represent, independently of each other, a halogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_{22}$ or $SR_{23}$ group, and $R_b$, $R_c$ and $R_d$ each represent, independently of each other, a hydrogen atom, a halogen atom or a $(C_1-C_6)$alkyl, $(C_1-C_6)$haloalkyl, cycloalkyl, cycloalkyl-$(C_1-C_6)$alkyl, heterocycle or heterocycle-$(C_1-C_6)$alkyl group;

$R_1$, $R_1'$, $R_4$ and $R_4'$ each represent, independently of each other, a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_mOR_{24}$, $(CH_2)_mSR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;

with the proviso that when $R_1$, $R_1'$, $R_4$ and $R_4'$ are the same, at least one of $R_a$ and $R_e$ is not the same as $R_1$;

$R_2$, $R_2'$, $R_3$ and $R_3'$ each represent, independently of each other, a hydrogen atom, a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$ alkyl, cycloalkyl, cycloalkyl-$(C_1-C_6)$alkyl, heterocycle, heterocycle-$(C_1-C_6)$alkyl, $OR_{42}$, $SR_{43}$, $NR_{44}R_{45}$, $COR_{46}$, $CO_2R_{47}$ or $CONR_{48}R_{49}$ group;

$L_X$ and $L_{X'}$ each represent, independently of each other, a bond, or a group selected from the group consisting of:

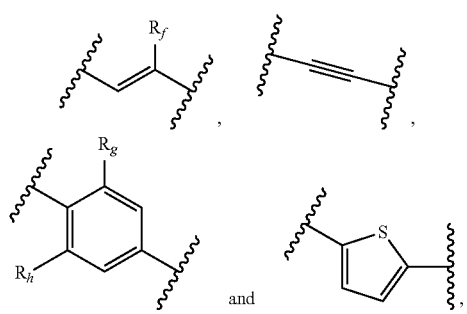

and wherein $R_f$, $R_g$ and $R_h$ each represent, independently of each other, a hydrogen or halogen atom, a $(C_1-C_6)$alkyl or $(C_1-C_6)$haloalkyl group;

X and X' each represent, independently of each other, $NR_{50}R_{51}$, $PR_{52}R_{53}$, $OR_{54}$, $SR_{55}$, heterocycle, heteroaryl or aryl, wherein:

said heterocycle and heteroaryl comprise at least one heteroatom bearing a lone pair of electrons conjugated with $C^+$, and are optionally substituted by one or more groups selected from a halogen atom, $(C_1-C_6)$alkyl, $(C_1-C_6)$haloalkyl, $OR_{56}$, $SR_{57}$ and $NR_{58}R_{59}$, and said aryl is para-substituted by a group selected from $NR_{60}R_{61}$, $PR_{62}R_{63}$, $OR_{64}$, and $SR_{65}$, and optionally substituted by one or more groups selected from a halogen atom, $(C_1-C_6)$alkyl, $(C_1-C_6)$haloalkyl, $OR_{66}$, $SR_{67}$ and $NR_{68}R_{69}$;

or $R_1$ and $R_2$, $R_3$ and $R_4$, $R_1'$ and $R_2'$, and/or $R_3'$ and $R_4'$, independently of each other, form together with the carbon atoms that carry them a cycle selected from the group consisting of cycloalkenyl, heterocycle, aryl and heteroaryl, said cycle being optionally substituted by one or more groups selected from a halogen atom, $(C_1-C_6)$alkyl, $(C_1-C_6)$haloalkyl, $OR_{70}$, $SR_{71}$ and $NR_{72}R_{73}$;

and/or $R_4$ and $R_4'$ form together a bond or a chain selected from the group consisting of $—C(R_{74}R_{75})—$, $—(CH_2)_n—$, $—Si(R_{76}R_{77})—$, $—(CH_2)_p—Y—(CH_2)_q—$ and $—Y—(CR_{78}R_{79})_r—Y'—$, wherein:

Y and Y' each represent, independently of each other, O, S or $NR_{80}$, n is equal to 2 or 3, p is equal to 1 or 2, q is equal to 0 or 1, r is equal to 1 or 2, $R_{74}$, $R_{75}$, $R_{78}$ to $R_{80}$ each represent, independently of each other, a hydrogen atom, a $(C_1-C_6)$alkyl or an aryl group, and $R_{76}$ and $R_{77}$ each represent, independently of each other, a $(C_1-C_6)$alkyl or an aryl group;

and/or $L_X$ represents a bond; X represents $NR_{50}'R_{51}'$, $PR_{52}'R_{53}'$, $OR_{54}'$ or $SR_{55}'$; and $R_2$ and $NR_{50}'$, $R_2$ and $PR_{52}'$, $R_2$ and $OR_{54}'$, $R_2$ and $SR_{55}'$, $R_3$ and $NR_{51}'$, $R_3$ and $PR_{53}'$, $R_3$ and $OR_{54}'$ and/or $R_3$ and $SR_{55}'$, independently of each other, form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$; and $R_{50}'$, $R_{51}'$, $R_{52}'$ and $R_{53}'$ represent respectively $R_{50}$, $R_{51}$, $R_{52}$ and $R_{53}$ when they are not linked with $R_2$ or $R_3$;

and/or $L_{X'}$ represents a bond; X' represents $NR_{50}'R_{51}'$, $PR_{52}'R_{53}'$, $OR_{54}'$ or $SR_{55}'$; and $R_2'$ and $NR_{50}'$, $R_2'$ and $PR_{52}'$, $R_2'$ and $OR_{54}'$, $R_2'$ and $SR_{55}'$, $R_3'$ and $NR_{51}'$, $R_3'$ and $PR_{53}'$, $R_3'$ and $OR_{54}'$ and/or $R_3'$ and $SR_{55}'$, independently of each other, form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$; and $R_{50}'$, $R_{51}'$, $R_{52}'$ and $R_{53}'$ represent respectively $R_{50}$, $R_{51}$, $R_{52}$ and $R_{53}$ when they are not linked with $R_2'$ or $R_3'$;

and/or $L_X$ represents

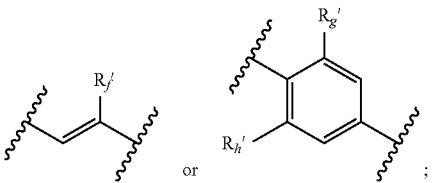

and $R_2$ and $R_f'$, $R_2$ and $R_g'$ and/or $R_3$ and $R_h'$, independently of each other, form together with the carbon atoms that carry them a cycloalkenyl or aryl group;

and/or $L_{X'}$ represents

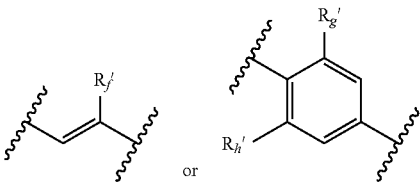

and $R_2'$ and $R_f'$, $R_2'$ and $R_g'$ and/or $R_3'$ and $R_h'$, independently of each other, form together with the carbon atoms that carry them a cycloalkenyl or aryl group;

and $R_5$ to $R_{53}$, $R_{56}$ to $R_{63}$, $R_{66}$ to $R_{73}$ and $R_{81}$ to $R_{84}$ each represent, independently of each other, a hydrogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1-C_6)$alkyl group;

and $R_{54}$, $R_{55}$, $R_{64}$ and $R_{65}$ each represent, independently of each other, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1-C_6)$alkyl group;

and $A^-$ represents a monovalent or multivalent, organic or inorganic anion.

In particular, the present invention relates to a compound of the above formula (I), wherein:

$R_0$ represents a hydrogen atom, a halogen atom, a $(C_1-C_6)$alkyl, $(C_1-C_6)$haloalkyl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_5$, $SR_6$, $NR_7R_8$, $PR_9R_{10}$, $COR_{11}$, $CO_2R_{12}$, $CONR_{13}R_{14}$, $SO_2R_{15}$, $SO_3H$, CN, $NO_2$, $OCOR_{16}$, $OCO_2R_{17}$, $NR_{18}COR_{19}$ or $NR_{20}SO_2R_{21}$ group, or is selected from the group consisting of:

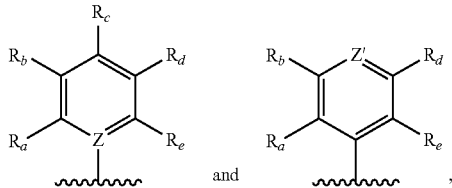

and wherein:
Z represents C or $N^+ A_z^-$ and Z' represents N or $N^+$—$R_c' A_z^-$, wherein
$A_z^-$ represents a monovalent organic or inorganic anion, and
$R_c'$ represents a hydrogen atom or a $(C_1-C_6)$alkyl group,
$R_a$ and $R_e$ each represent, independently of each other, a halogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_{22}$ or $SR_{23}$ group, and
$R_b$, $R_c$ and $R_d$ each represent, independently of each other, a hydrogen atom, a halogen atom or a $(C_1-C_6)$alkyl, $(C_1-C_6)$haloalkyl, cycloalkyl, cycloalkyl-$(C_1-C_6)$alkyl, heterocycle or heterocycle-$(C_1-C_6)$alkyl group;
$R_1$=$R_1'$, and $R_1$ represents a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_mOR_{24}$, $(CH_2)_mSR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;
$R_4$=$R_4'$, and $R_4$ represents a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_mOR_{24}$, $(CH_2)_mSR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;
with the proviso that when $R_1$ and $R_4$ are the same, at least one of $R_a$ and $R_e$ is not the same as $R_1$;
or
$R_4$ and $R_4'$ form together a bond or a chain selected from the group consisting of —$C(R_{74}R_{75})$—, —$(CH_2)_n$—, —$Si(R_{76}R_{77})$—, —$(CH_2)_p$—Y—$(CH_2)_q$—, and —Y—$(CR_{78}R_{79})_r$—Y'—, wherein:
Y and Y' each represent, independently of each other, O, S or $NR_{80}$,
n is equal to 2 or 3,
p is equal to 1 or 2,
q is equal to 0 or 1,
r is equal to 1 or 2,
$R_{74}$, $R_{75}$, $R_{78}$ to $R_{80}$ each represent, independently of each other, a hydrogen atom, a $(C_1-C_6)$alkyl or an aryl group, and
$R_{76}$ and $R_{77}$ each represent, independently of each other, a $(C_1-C_6)$alkyl or an aryl group;

$R_2$=$R_2'$, $R_3$=$R_3'$, and $R_2$ and $R_3$ each represent, independently of each other, a hydrogen atom, a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_{42}$, $SR_{43}$, $NR_{44}R_{45}$, $COR_{46}$, $CO_2R_{47}$ or $CONR_{48}R_{49}$ group, preferably a hydrogen atom;
$L_X$=$L_{X'}$, and $L_X$ represents a bond, or a group selected from the group consisting of:

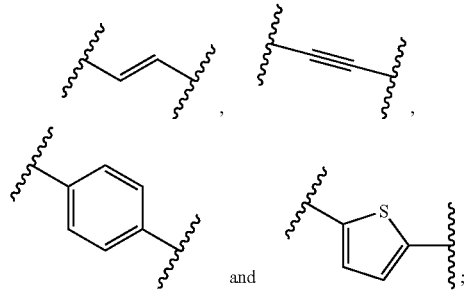

and

X=X', and X represents $NR_{50}R_{51}$, heterocycle, heteroaryl or aryl, wherein:
said heterocycle and heteroaryl group comprise at least one nitrogen atom bearing a lone pair of electrons conjugated with $C^+$, and are optionally substituted by one or more groups selected from a halogen atom, a $(C_1-C_6)$alkyl, $(C_1-C_6)$haloalkyl, $OR_{56}$, $SR_{57}$ and $NR_{58}R_{59}$ group, and
said aryl is para-substituted by a $NR_{60}R_{61}$ group, and optionally substituted by one or more groups selected from a halogen atom, a $(C_1-C_6)$alkyl, $(C_1-C_6)$haloalkyl, $OR_{66}$, $SR_{67}$ and $NR_{68}R_{69}$ group;
or
$R_1$ together with $R_2$, and $R_1'$ together with $R_2'$ form with the carbon atoms that carry them an identical cycle selected from the group consisting of cycloalkenyl, heterocycle, aryl and heteroaryl, said cycle being optionally substituted by one or more groups selected from a halogen atom, $(C_1-C_6)$alkyl, $(C_1-C_6)$haloalkyl, $OR_{70}$, $SR_{71}$ and $NR_{72}R_{73}$;
and/or
$R_3$ together with $R_4$, and $R_3'$ together with $R_4'$ form with the carbon atoms that carry them an identical cycle selected from the group consisting of cycloalkenyl, heterocycle, aryl and heteroaryl, said cycle being optionally substituted by one or more groups selected from a halogen atom, $(C_1-C_6)$alkyl, $(C_1-C_6)$haloalkyl, $OR_{70}$, $SR_{71}$ and $NR_{72}R_{73}$;
and/or
$L_X$=$L_{X'}$ and $L_X$ represents a bond; X=X' and X represents $NR_{50}'R_{51}'$, $PR_{52}'R_{53}'$, $OR_{54}'$ or $SR_{55}'$; and
$R_2$ and $NR_{50}'$, and $R_2'$ and $NR_{50}'$; $R_2$ and $PR_{52}'$, and $R_2'$ and $PR_{52}'$; $R_2$ and $OR_{54}'$, and $R_2'$ and $OR_{54}'$; or $R_2$ and $SR_{55}'$, and $R_2'$ and $SR_{55}'$ form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$;
and/or
$R_3$ and $NR_{51}'$, and $R_3'$ and $NR_{51}'$; $R_3$ and $PR_{53}'$, and $R_3'$ and $PR_{53}'$; $R_3$ and $OR_{54}'$, and $R_3'$ and $OR_{54}'$; or $R_3$ and $SR_{55}'$, and $R_3'$ and $SR_{55}'$ form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$;

and $R_{50}'$, $R_{51}'$, $R_{52}'$ and $R_{53}'$ represent respectively $R_{50}$, $R_{51}$, $R_{52}$ and $R_{53}$ when they are not linked with $R_2$ or $R_3$;

and $R_5$ to $R_{53}$, $R_{56}$ to $R_{63}$, $R_{66}$ to $R_{73}$ and $R_{81}$ to $R_{84}$ each represent, independently of each other, a hydrogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1-C_6)$alkyl group;

and $R_{54}$, $R_{55}$, $R_{64}$ and $R_{65}$ each represent, independently of each other, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1-C_6)$alkyl group;

and $A^-$ represents a monovalent or multivalent, organic or inorganic anion.

Definitions

The term "halogen" as used in the present invention refers to an atom of fluorine, bromine, chlorine or iodine. Advantageously, this is an atom of fluorine.

The term "$(C_1-C_6)$alkyl" as used in the present invention refers to a saturated, linear or branched hydrocarbon chain comprising from 1 to 6 carbon atoms, including, but not limited to, methyl, ethyl, n-propyl, isopropyl, n-butyl, isobutyl, sec-butyl, tert-butyl, n-pentyl, n-hexyl and the like.

The term "$(C_1-C_6)$haloalkyl" as used in the present invention refers to any $(C_1-C_6)$alkyl group as defined above in which one or more hydrogen atoms have been each replaced with a halogen atom. It can be notably a trifluoromethyl group.

The term "$(C_2-C_6)$alkenyl" as used in the present invention refers to a linear or branched hydrocarbon chain comprising at least one double bond and comprising from 2 to 6 carbon atoms including, but not limited to, ethenyl (e.g. vinyl), propenyl (e.g. allyl) and the like.

The term "$(C_2-C_6)$alkynyl" as used in the present invention refers to a linear or branched hydrocarbon chain comprising at least one triple bond and comprising from 2 to 6 carbon atoms including, but not limited to, ethynyl, propynyl and the like.

The term "cycloalkyl" as used in the present invention refers to a saturated hydrocarbon ring comprising from 3 to 7, advantageously from 5 to 7, carbon atoms including, but not limited to, cyclohexyl, cyclopentyl, cyclopropyl, cycloheptyl and the like.

The term "cycloalkenyl" as used in the present invention refers to an unsaturated hydrocarbon ring comprising from 3 to 7, advantageously from 5 to 6, carbon atoms, including, but not limited to, cyclopentenyl, cyclohexenyl, cyclopentadienyl, cyclohexadienyl and the like.

The term "heterocycle" as used in the present invention refers to a saturated or unsaturated non-aromatic monocycle or polycycle, comprising fused, bridged or spiro rings, preferably fused rings, advantageously comprising 3 to 10, notably 3 to 6, atoms in each ring, in which the atoms of the ring(s) comprise one or more, advantageously 1 to 3, heteroatoms selected from O, S and N, preferably O and N, the remainder being carbon atoms.

A saturated heterocycle is more particularly a 3-, 4-, 5- or 6-membered, even more particularly a 5- or 6-membered saturated monocyclic heterocycle such as an aziridine, an azetidine, a pyrrolidine, a tetrahydrofuran, a 1,3-dioxolane, a tetrahydrothiophene, a thiazolidine, an isothiazolidine, an oxazolidine, an isoxazolidine, an imidazolidine, a pyrazolidine, a triazolidine, a piperidine, a piperazine, a 1,4-dioxane, a morpholine or a thiomorpholine.

An unsaturated heterocycle is more particularly an unsaturated monocyclic or bicyclic heterocycle, each cycle comprising 5 or 6 members, such as 1H-azirine, a pyrroline, a dihydrofuran, a 1,3-dioxolene, a dihydrothiophene, a thiazoline, an isothiazoline, an oxazoline, an isoxazoline, an imidazoline, a pyrazoline, a triazoline, a dihydropyridine, a tetrahydropyridine, a dihydropyrimidine, a tetrahydropyrimidine, a dihydropyridazine, a tetrahydropyridazine, a dihydropyrazine, a tetrahydropyrazine, a dihydrotriazine, a tetrahydrotriazine, a 1,4-dioxene, an indoline, a 2,3-dihydrobenzofuran (coumaran), a 2,3-dihydrobenzothiophene, a 1,3-benzodioxole, a 1,3-benzoxathiole, a benzoxazoline, a benzothiazoline, a benzimidazoline, a chromane or a chromene.

The term "aryl", as used in the present invention, refers to an aromatic hydrocarbon group comprising preferably 6 to 14 carbon atoms and comprising one or more fused rings, such as, for example, a phenyl, naphthyl or anthracenyl group. Advantageously, it will be a phenyl group.

The term "heteroaryl" as used in the present invention refers to an aromatic heterocycle as defined above. It can be more particularly an aromatic monocyclic, bicyclic or tricyclic heterocycle, each cycle comprising 5 or 6 members, such as a pyrrole, a furan, a thiophene, a thiazole, an isothiazole, an oxazole, an isoxazole, an imidazole, a pyrazole, a triazole, a pyridine, a pyrimidine, an indole, a benzofuran, a benzothiophene, a benzothiazole, a benzoxazole, a benzimidazole, an indazole, a benzotriazole, a quinoline, an isoquinoline, a cinnoline, a quinazoline, a quinoxaline, a carbazole, or a julolidine.

The term "cycloalkyl-$(C_1-C_6)$alkyl" as used in the present invention refers to any cycloalkyl group as defined above, which is bound to the molecule by means of a $(C_1-C_6)$-alkyl group as defined above.

The term "heterocycle-$(C_1-C_6)$alkyl" as used in the present invention refers to a heterocycle group as defined above, which is bound to the molecule by means of a $(C_1-C_6)$-alkyl group as defined above.

The term "aryl-$(C_1-C_6)$-alkyl" as used in the present invention refers to any aryl group as defined above, which is bound to the molecule by means of a $(C_1-C_6)$-alkyl group as defined above. In particular, it can be a benzyl group.

The term "heteroaryl-$(C_1-C_6)$alkyl" as used in the present invention refers to a heteroaryl group as defined above, which is bound to the molecule by means of a $(C_1-C_6)$-alkyl group as defined above.

The expression "organic or inorganic anion" refers, within the sense of the present invention, to a negatively-charged counter-ion. It can be in particular a halide (fluoride, chloride, bromide, iodide), perchlorate, nitrate, sulfate, alkylsulfate, benzenesulfonate, p-toluene sulfonate, chlorosulfonate, fluorosulfonate, trifluorosulfonate, methanesulfonate, benzenesulfinate, tetrafluoroborate, tetraphenylborate, tetrakis(pentafluorophenyl)borate, tris(tetrachlorobenzenediolato)phosphate(V) (TRISPHAT), (1,1'-binaphthalene-2,2'diolato)(bis(tetrachloro-1,2-benzenediolato)phosphate(V) (BINPHAT), acetate, trifluoroacetate, propionate, benzoate, oxalate, succinate, oleate, stearate, citrate, 4-hydroxyphenolate, 2,3,5,6-tetrachloro-4-hydroxyphenolate, 2,3-dichloro-5,6-dicyano-4-hydroxyphenolate (DDQH$^-$), hydrogenophosphate, dihydrogenophosphate or hexafluorophosphate anion. Preferably, it is a hexafluorophosphate, 2,3-dichloro-5,6-dicyano-4-hydroxyphenolate (DDQH$^-$), tetrafluoroborate, halide or triflate anion, more preferably a 2,3-dichloro-5,6-dicyano-4-hydroxyphenolate (DDQH$^-$) or hexafluorophosphate anion, notably a hexafluorophosphate anion.

In the context of the present invention, "C$^+$" refers to the trivalent carbon atom that is linked to R$_0$.

In the context of the present invention, the terms "precursor" or "intermediate" are used indifferently.

DETAILED DESCRIPTION AND ADDITIONAL EMBODIMENTS

According to a particular embodiment, R$_0$ represents a hydrogen atom, a halogen atom, a (C$_1$-C$_6$)alkyl, (C$_1$-C$_6$)haloalkyl, OR$_5$, SR$_6$, NR$_7$R$_8$, CN or NO$_2$ group, or is selected from the group consisting of:

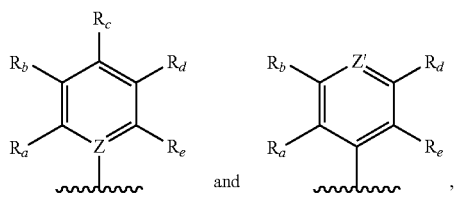

wherein R$_a$, R$_b$, R$_c$, R$_d$, R$_e$, Z and Z' are as defined above.

According to another particular embodiment, R$_0$ represents a hydrogen atom, a (C$_1$-C$_6$)haloalkyl, NR$_7$R$_8$, CN or NO$_2$ group, or is selected from the group consisting of:

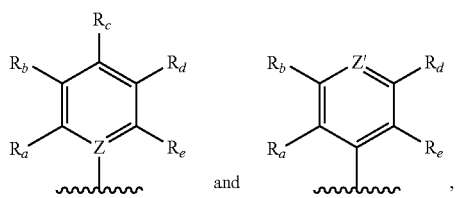

wherein:
Z represents C or N$^+$ A$_z^-$ and Z' represents N or N$^+$—R$_c$' A$_z^-$, wherein
A$_z^-$ represents a hexafluorophosphate, tetrafluoroborate, tetraphenylborate, DDQH$^-$, halide or triflate anion, preferably a DDQH$^-$ or hexafluorophosphate anion, notably a hexafluorophosphate anion, and
R$_c$' represents a hydrogen atom or a (C$_1$-C$_6$)alkyl group, notably a methyl, ethyl or propyl group,
R$_a$ and R$_e$ each represent, independently of each other, a (C$_1$-C$_6$)alkyl, aryl or OR$_{22}$ group, and R$_b$, R$_c$ and R$_d$ are the same and represent a hydrogen atom or a (C$_1$-C$_6$)alkyl group.

According to still another particular embodiment, R$_0$ represents a hydrogen atom, a (C$_1$-C$_6$)alkyl, NR$_7$R$_8$, CN, CF$_3$ or NO$_2$ group, or is selected from the group consisting of:

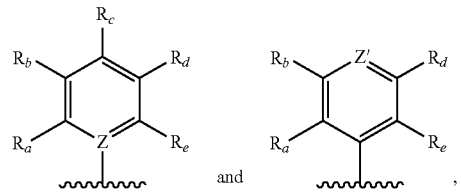

wherein R$_a$ and R$_e$ each represent, independently of each other, a (C$_1$-C$_6$)alkyl, aryl or OR$_{22}$ group, notably a methyl, OCH$_3$ or phenyl group; and R$_b$, R$_c$ and R$_d$ each represent a hydrogen atom.

According to yet another particular embodiment, R$_0$ represents a hydrogen atom, a NR$_7$R$_8$, CN, CF$_3$ or NO$_2$ group, or is selected from the group consisting of:

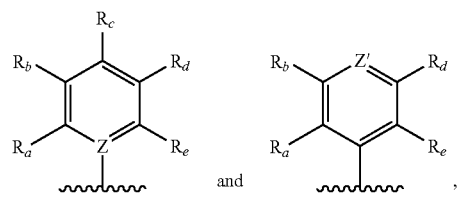

wherein R$_a$ and R$_e$ each represent, independently of each other, a (C$_1$-C$_6$)alkyl, aryl or OR$_{22}$ group, notably a methyl, OCH$_3$ or phenyl group; and R$_b$, R$_c$ and R$_d$ each represent a hydrogen atom.

According to still another particular embodiment, R$_0$ represents a hydrogen atom, a CF$_3$, NR$_7$R$_8$, CN or NO$_2$ group, wherein R$_7$ and R$_8$ each represent, independently of each other, a hydrogen atom, a (C$_1$-C$_6$)alkyl, aryl, heteroaryl, aryl-(C$_1$-C$_6$)alkyl, heteroaryl-(C$_1$-C$_6$)alkyl, cycloalkyl, cycloalkyl-(C$_1$-C$_6$)alkyl, heterocycle or heterocycle-(C$_1$-C$_6$)alkyl group, said group being optionally substituted by one or more groups selected from a halogen atom, a (C$_1$-C$_6$)alkyl, (C$_1$-C$_6$)haloalkyl, OR$_{85}$, SR$_{86}$ and NR$_{87}$R$_{88}$ group, wherein R$_{85}$ to R$_{88}$ each represent, independently of each other, a hydrogen atom or a (C$_1$-C$_6$)alkyl group; or is selected from the group consisting of:

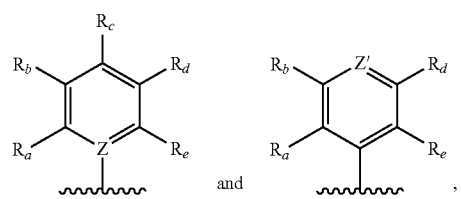

wherein:
Z represents C or N$^+$ A$_z^-$ and Z' represents N or N$^+$—R$_c$' A$_z^-$, wherein
A$_z^-$ represents a hexafluorophosphate, tetrafluoroborate, tetraphenylborate, DDQH$^-$, halide or triflate anion, and $R_c'$ represents a hydrogen atom or a $(C_1-C_6)$alkyl group, notably a methyl, ethyl or n-propyl group, $R_a$ and $R_e$ are the same, and represent a $(C_1-C_6)$alkyl, aryl or $OR_{22}$, wherein $R_{22}$ represents a $(C_1-C_6)$alkyl group, and $R_b$, $R_c$ and $R_d$ are a hydrogen atom.

According to yet another particular embodiment, $R_0$ represents a hydrogen atom, a $CF_3$, $NR_7R_8$, CN or $NO_2$ group, wherein $R_7$ and $R_8$ each represent, independently of each other, a hydrogen atom, a $(C_1-C_6)$alkyl, aryl, aryl-$(C_1-C_6)$alkyl or cycloalkyl group, notably a hydrogen atom, a methyl, ethyl, n-propyl, isopropyl, n-butyl, isobutyl, sec-butyl, tert-butyl, phenyl, naphthyl, benzyl, cyclohexyl, cyclopentyl or cyclopropyl group; or is selected from the group consisting of:

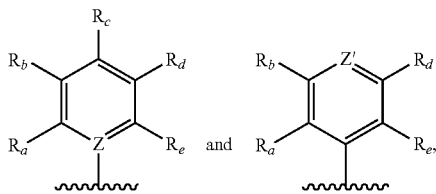

wherein:

Z represents $C$ or $N^+ A_z^-$ and Z' represents N or $N^+-R_c' A_z^-$, wherein $A_z^-$ represents a hexafluorophosphate, tetrafluoroborate, tetraphenylborate, $DDQH^-$, halide or triflate anion, and $R_c'$ represents a hydrogen atom or a methyl, ethyl or propyl group, $R_a$ and $R_e$ are the same, and represent a methyl, ethyl, propyl, phenyl, methoxy or ethoxy group, and $R_b$, $R_c$ and $R_d$ are a hydrogen atom.

According to still another particular embodiment, $R_0$ represents a hydrogen atom, or is selected from the group consisting of:

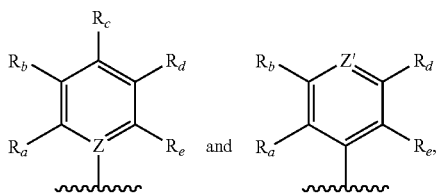

wherein Z represents $C$ or $N^+ A_z^-$ and Z' represents N or $N^+-R_c' A_z^-$, wherein $A_z^-$ represents a hexafluorophosphate, tetrafluoroborate, tetraphenylborate, $DDQH^-$, halide or triflate anion; $R_a$ and $R_e$ are the same, and represent a methyl, phenyl or methoxy group; and $R_b$, $R_c$ and $R_d$ are a hydrogen atom.

According to a preferred embodiment, $R_0$ represents a hydrogen atom, a $(C_1-C_6)$alkyl or a CN group, preferably a hydrogen atom or a CN group, notably a hydrogen atom.

According to a particular embodiment, $R_1$, $R_1'$, $R_4$ and $R_4'$ each represent, independently of each other, a halogen atom, a $(C_1-C_6)$alkyl, $(C_1-C_6)$haloalkyl, aryl, heteroaryl, aryl-$(C_1-C_6)$alkyl, cycloalkyl, heterocycle, $(CH_2)_mOR_{24}$, $(CH_2)_mSR_{25}$, $OR_{26}$, $SR_{27}$, $NR_{28}R_{29}$ or $PR_{30}R_{31}$ group.

According to another particular embodiment, $R_1$, $R_1'$, $R_4$ and $R_4'$ each represent, independently of each other, a $(C_1-C_6)$alkyl, $(C_1-C_6)$haloalkyl, aryl, heteroaryl, aryl-$(C_1-C_6)$alkyl, cycloalkyl, heterocycle, $(CH_2)_mOR_{24}$, $(CH_2)_mSR_{25}$, $OR_{26}$, $SR_{27}$, $NR_{28}R_{29}$ or $PR_{30}R_{31}$ group, wherein $R_{24}$ to $R_{31}$ each represent, independently of each other, a hydrogen atom, a $(C_1-C_6)$alkyl, aryl, heteroaryl, cycloalkyl or heterocycle group, said group being optionally substituted by one or more groups selected from a halogen atom or a $(C_1-C_6)$alkyl group.

According to still another particular embodiment, $R_1$, $R_1'$, $R_4$ and $R_4'$ each represent, independently of each other, a $(C_1-C_6)$alkyl, $(C_1-C_6)$haloalkyl, aryl, benzyl, cyclohexyl, cyclopentyl, cyclopropyl, $(CH_2)_mOR_{24}$, $(CH_2)_mSR_{25}$, $OR_{26}$, $SR_{27}$, $NR_{28}R_{29}$ or $PR_{30}R_{31}$ group, wherein $R_{24}$ to $R_{31}$ each represent, independently of each other, a hydrogen atom or a $(C_1-C_6)$alkyl group.

According to yet another particular embodiment, $R_1$, $R_1'$, $R_4$ and $R_4'$ each represent, independently of each other, a $(C_1-C_6)$alkyl, $(C_1-C_6)$haloalkyl, aryl, $(CH_2)_mOR_{24}$, $(CH_2)_mSR_{25}$, $OR_{26}$, or $SR_{27}$ group.

According to a preferred embodiment, $R_1$, $R_1'$, $R_4$ and $R_4'$ each represent, independently of each other, a $(C_1-C_6)$alkyl, $(C_1-C_6)$haloalkyl, aryl, $(CH_2)_mOR_{24}$, $(CH_2)_mSR_{25}$, $OR_{26}$ or $SR_{27}$ group, wherein $R_{24}$ to $R_{27}$ each represent, independently of each other, a hydrogen atom or a $(C_1-C_6)$alkyl group. Preferably, $R_1$, $R_1'$, $R_4$ and $R_4'$ each represent, independently of each other, a methyl, ethyl, n-propyl, isopropyl, n-butyl, isobutyl, sec-butyl, tert-butyl, $CF_3$, phenyl, $CH_2OR_{24}$, $CH_2SR_{25}$, $OR_{26}$ or $SR_{27}$ group, wherein $R_{24}$ to $R_{27}$ each represent, independently of each other, a hydrogen atom or a methyl, ethyl, n-propyl, isopropyl, n-butyl, isobutyl, sec-butyl, tert-butyl group. More preferably, $R_1$, $R_1'$, $R_4$ and $R_4'$ each represent, independently of each other, a $CH_2OR_{24}$ or $OR_{26}$ group, wherein $R_{24}$ and $R_{26}$ represent a hydrogen atom or a methyl, ethyl, n-propyl group. Even more preferably, $R_1$ represents a OH, $CH_2OCH_3$ or methoxy group.

According to a particular embodiment, $R_1=R_1'$, and $R_4=R_4'$.

According to another particular embodiment, $R_1=R_4$, and $R_1'=R_4'$, notably $R_1=R_4=R_1'=R_4'$, with the proviso that when $R_1$, $R_1'$, $R_4$ and $R_4'$ are the same, at least one of $R_a$ and $R_e$ is not the same as $R_1$.

According to yet another particular embodiment, $R_1=R_4=R_1'=R_4'$, and $R_1$ represents a $(C_1-C_6)$alkyl, $(C_1-C_6)$haloalkyl, aryl, $(CH_2)_mOR_{24}$, $(CH_2)_mSR_{25}$, $OR_{26}$ or $SR_{27}$ group.

According to yet another particular embodiment, $R_1=R_4=R_1'=R_4'$, and $R_1$ represents a $(C_1-C_6)$alkyl, $(C_1-C_6)$haloalkyl, aryl, $CH_2OR_{24}$, $CH_2SR_{25}$, $OR_{26}$ or $SR_{27}$ group.

According to still another particular embodiment, $R_1=R_4=R_1'=R_4'$, and $R_1$ represents a methyl, ethyl, n-propyl, isopropyl, n-butyl, isobutyl, sec-butyl, tert-butyl, $CF_3$, phenyl, $CH_2OR_{24}$, $CH_2SR_{25}$, $OR_{26}$ or $SR_{27}$ group, wherein $R_{24}$ to $R_{27}$ each represent, independently of each other, a hydrogen atom or a methyl, ethyl or n-propyl group.

According to a particular embodiment, $R_1=R_4=R_1'=R_4'$, and $R_1$ represents a $CH_2OR_{24}$ or $OR_{26}$ group, wherein $R_{24}$ and $R_{26}$ represent a hydrogen atom or a methyl, ethyl or n-propyl group. Notably, $R_1$ represents a OH, $CH_2OCH_3$ or methoxy group, more preferably a methoxy group.

According to a preferred embodiment, $R_1=R_4=R_1'=R_4'$, and $R_1$ represents a $(C_1-C_6)$alkyl group, such as a methyl, ethyl, n-propyl, isopropyl, n-butyl, isobutyl, sec-butyl or tert-butyl group, or a $OR_{26}$ group, wherein $R_{26}$ represent a hydrogen atom or a methyl, ethyl or n-propyl group. Preferably, $R_1$ represents a methyl or methoxy group.

According to a particular embodiment, $R_2$, $R_2'$, $R_3$ and $R_3'$ each represent, independently of each other, a hydrogen or halogen atom, or a ($C_1$-$C_6$)alkyl group, notably a methyl, ethyl or n-propyl group.

According to a preferred embodiment, $R_2$, $R_2'$, $R_3$ and $R_3'$ each represent a hydrogen atom.

In a particular embodiment, $R_1=R_1'$, $R_2=R_2'$, $R_3=R_3'$ and $R_4=R_4'$.

In a particular embodiment, $R_1$ and $R_2$, $R_3$ and $R_4$, $R_1'$ and $R_2'$, and/or $R_3'$ and $R_4'$, independently of each other, form together with the carbon atoms that carry them a cycle selected from the group consisting of cycloalkenyl, heterocycle, aryl and heteroaryl, said cycle being optionally substituted by one or more groups selected from a halogen atom, ($C_1$-$C_6$)alkyl, ($C_1$-$C_6$)haloalkyl, $OR_{70}$, $SR_{71}$ and $NR_{72}R_{73}$, wherein $R_{70}$ to $R_{73}$ each represent, independently of each other, a hydrogen atom or a ($C_1$-$C_6$)alkyl group.

In another particular embodiment, $R_1$ and $R_2$, $R_3$ and $R_4$, $R_1'$ and $R_2'$, and/or $R_3'$ and $R_4'$, independently of each other, form together with the carbon atoms that carry them a cycle selected from the group consisting of cyclopentene, cyclohexene, benzene, naphthalene, 1,3-dioxolene and 1,4-dioxene.

In still another particular embodiment, $R_1$ and $R_2$, and $R_1'$ and $R_2'$, form together with the carbon atoms that carry them a benzene.

In yet another particular embodiment, $R_1$ and $R_2$, $R_3$ and $R_4$, $R_1'$ and $R_2'$, and $R_3'$ and $R_4'$, each other form together with the carbon atoms that carry them a benzene or a naphthalene.

In a particular embodiment, $L_X$ and $L_{X'}$ each represent, independently of each other, a bond or a group selected from the group consisting of:

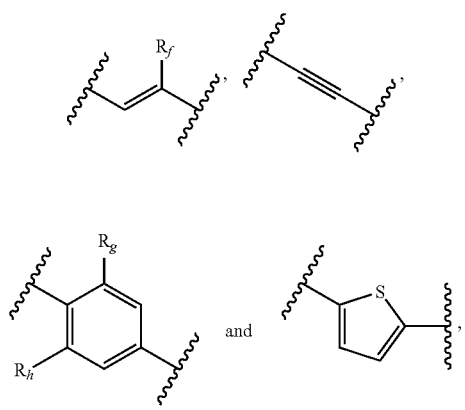

and wherein $R_f$, $R_g$ and $R_h$ each represent, independently of each other, a hydrogen or halogen atom, a ($C_1$-$C_6$)alkyl or ($C_1$-$C_6$)haloalkyl group; preferably, a hydrogen atom or a methyl, ethyl, n-propyl, isopropyl, n-butyl, isobutyl, sec-butyl, tert-butyl or $CF_3$ group, more preferably a hydrogen atom.

In a preferred embodiment, $L_X$ and $L_{X'}$ are the same.

In a particular embodiment, $L_X$ and $L_{X'}$ are the same, $R_f$, $R_g$ and $R_h$ are H, and hence the compounds according to the invention can have one of the following formulas:

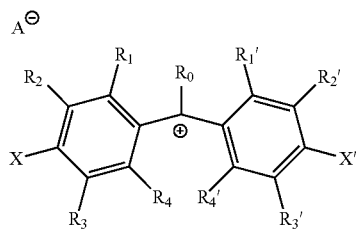
(Ia)

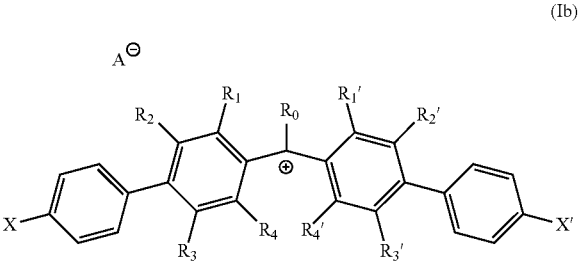
(Ib)

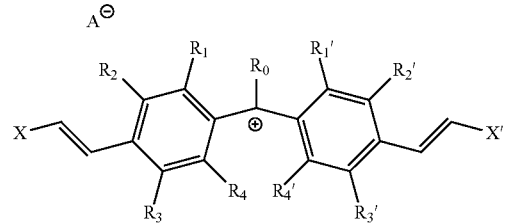
(Ic)

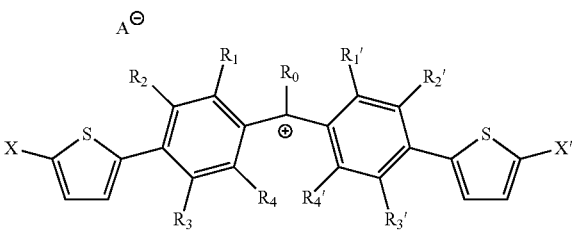
(Id)

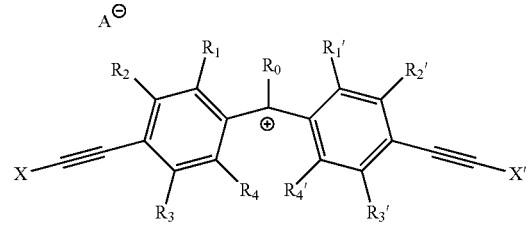
(Ie)

wherein $R_0$, $R_1$, $R_2$, $R_3$, $R_4$, $R_1'$, $R_2'$, $R_3'$, $R_4'$, X and X' are as defined above.

Advantageously, $L_X$ and $L_{X'}$ each represent a bond, and the compounds according to the invention thus correspond to the formula (Ia).

In a particular embodiment, X and X' each represent, independently of each other, $NR_{50}R_{51}$, $PR_{52}R_{53}$, $OR_{54}$, $SR_{55}$, heterocycle, heteroaryl or aryl, wherein:

$R_{50}$ to $R_{53}$ each represent, independently of each other, a hydrogen atom, a ($C_1$-$C_6$)alkyl, aryl, aryl-($C_1$-$C_6$)alkyl, heteroaryl-($C_1$-$C_6$)alkyl, cycloalkyl, heterocycle, said group being optionally substituted by one or more groups selected from a halogen atom, a ($C_1$-$C_6$)alkyl, ($C_1$-$C_6$)haloalkyl, $OR_{85}$, $SR_{86}$ and $NR_{87}R_{88}$ group, wherein $R_{85}$ to $R_{88}$ each represent, independently of each other, a hydrogen atom or a ($C_1$-$C_6$)alkyl group;

$R_{54}$ and $R_{55}$ each represent, independently of each other, a $(C_1$-$C_6)$alkyl, aryl, aryl-$(C_1$-$C_6)$alkyl, heteroaryl-$(C_1$-$C_6)$alkyl, cycloalkyl, heterocycle, said group being optionally substituted by one or more groups selected from a halogen atom, a $(C_1$-$C_6)$alkyl, $(C_1$-$C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1$-$C_6)$alkyl group;

said heterocycle and heteroaryl comprise at least one heteroatom bearing a lone pair of electrons conjugated with $C^+$, and are optionally substituted by one or more groups selected from a halogen atom, $(C_1$-$C_6)$alkyl, $(C_1$-$C_6)$haloalkyl, $OR_{56}$, $SR_{57}$ and $NR_{58}R_{59}$, $R_{56}$ to $R_{59}$ each represent, independently of each other, a hydrogen atom or a $(C_1$-$C_6)$alkyl group; and said aryl is para-substituted by a group selected from $NR_{60}R_{61}$, $PR_{62}R_{63}$, $OR_{64}$, and $SR_{65}$, and optionally substituted by one or more groups selected from a halogen atom, $(C_1$-$C_6)$alkyl, $(C_1$-$C_6)$haloalkyl, $OR_{66}$, $SR_{67}$ and $NR_{68}R_{69}$; wherein:

$R_{60}$ to $R_{63}$ each represent, independently of each other, a hydrogen atom, a $(C_1$-$C_6)$alkyl, aryl, aryl-$(C_1$-$C_6)$alkyl, heteroaryl-$(C_1$-$C_6)$alkyl, cycloalkyl, or heterocycle group;

$R_{64}$ and $R_{65}$ each represent, independently of each other, a $(C_1$-$C_6)$alkyl, aryl, aryl-$(C_1$-$C_6)$alkyl, heteroaryl-$(C_1$-$C_6)$alkyl, cycloalkyl, or heterocycle group; and $R_{66}$ to $R_{69}$ each represent, independently of each other, a hydrogen atom or a $(C_1$-$C_6)$alkyl group.

In another particular embodiment, X and X' each represent, independently of each other, $NR_{50}R_{51}$, heterocycle, heteroaryl or aryl, wherein:

$R_{50}$ and $R_{51}$ each represent, independently of each other, a hydrogen atom, or a methyl, ethyl, n-propyl, isopropyl, n-butyl, isobutyl, sec-butyl, tert-butyl, phenyl, naphthyl, benzyl, cyclohexyl, cyclopentyl or cyclopropyl group, said group being optionally substituted by one or more groups selected from a halogen atom, a $(C_1$-$C_6)$alkyl, $(C_1$-$C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1$-$C_6)$alkyl group;

said heterocycle and heteroaryl comprise at least one heteroatom bearing a lone pair of electrons conjugated with $C^+$, and are optionally substituted by one or more groups selected from a halogen atom, $(C_1$-$C_6)$alkyl, $(C_1$-$C_6)$haloalkyl, $OR_{56}$, $SR_{57}$ and $NR_{58}R_{59}$, wherein $R_{56}$ to $R_{59}$ each represent, independently of each other, a hydrogen atom or a $(C_1$-$C_6)$alkyl group;

advantageously, said heterocycle is selected from the group consisting of aziridine, azetidine, pyrrolidine, thiazolidine, isothiazolidine, oxazolidine, isoxazolidine, imidazolidine, pyrazolidine, triazolidine, piperidine, piperazine, morpholine, thiomorpholine, 1H-azirine, pyrroline, thiazoline, isothiazoline, oxazoline, isoxazoline, imidazoline, pyrazoline, triazoline, dihydropyridine, tetrahydropyridine, dihydropyrimidine, tetrahydropyrimidine, dihydropyridazine, tetrahydropyridazine, dihydropyrazine, tetrahydropyrazine, dihydrotriazine, tetrahydrotriazine, indoline, 1,3-benzoxathiole, benzoxazoline, benzothiazoline and benzimidazoline;

still advantageously, said heteroaryl is selected from the group consisting of pyrrole, thiazole, isothiazole, oxazole, isoxazole, imidazole, pyrazole, triazole, pyridine, pyrimidine, indole, benzothiazole, benzoxazole, benzimidazole, indazole, benzotriazole, quinoline, isoquinoline, cinnoline, quinazoline, quinoxaline and carbazole; and said aryl is para-substituted by a group selected from $NR_{60}R_{61}$, $PR_{62}R_{63}$, $OR_{64}$, and $SR_{65}$, and optionally substituted by one or more groups selected from a halogen atom, $(C_1$-$C_6)$alkyl, $(C_1$-$C_6)$haloalkyl, $OR_{66}$, $SR_{67}$ and $NR_{68}R_{69}$, wherein:

$R_{60}$ to $R_{63}$ each represent, independently of each other, a hydrogen atom, or a methyl, ethyl, n-propyl, isopropyl, n-butyl, isobutyl, sec-butyl, tert-butyl, phenyl, naphthyl, benzyl, cyclohexyl, cyclopentyl or cyclopropyl group;

$R_{64}$ and $R_{65}$ each represent, independently of each other, a methyl, ethyl, n-propyl, isopropyl, n-butyl, isobutyl, sec-butyl, tert-butyl, phenyl, naphthyl, benzyl, cyclohexyl, cyclopentyl or cyclopropyl group; and $R_{66}$ to $R_{69}$ each represent, independently of each other, a hydrogen atom or a $(C_1$-$C_6)$alkyl group.

In still another embodiment X and X' each represent, independently of each other, $NR_{50}R_{51}$, heterocycle, heteroaryl or aryl, wherein:

said heterocycle and heteroaryl comprise at least one nitrogen atom bearing a lone pair of electrons conjugated with $C^+$, and are optionally substituted by one or more groups selected from a halogen atom, a $(C_1$-$C_6)$ alkyl, $(C_1$-$C_6)$haloalkyl, $OR_{56}$, $SR_{57}$ and $NR_{58}R_{59}$ group, and said aryl is para-substituted by a $NR_{60}R_{61}$ group, and optionally substituted by one or more groups selected from a halogen atom, a $(C_1$-$C_6)$alkyl, $(C_1$-$C_6)$haloalkyl, $OR_{66}$, $SR_{67}$ and $NR_{68}R_{69}$ group.

In yet another embodiment X and X' each represent, independently of each other, $NR_{50}R_{51}$, heterocycle, heteroaryl or aryl, wherein:

$R_{50}$ and $R_{51}$ each represent, independently of each other, a hydrogen atom, or a methyl, ethyl, n-propyl, isopropyl, n-butyl, isobutyl, sec-butyl, tert-butyl, phenyl, naphthyl, benzyl, cyclohexyl, cyclopentyl or cyclopropyl group, said group being optionally substituted by one or more groups selected from a halogen atom, a $(C_1$-$C_6)$alkyl, $(C_1$-$C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1$-$C_6)$alkyl group;

said heterocycle and heteroaryl group comprises at least one nitrogen atom bearing a lone pair of electrons conjugated with $C^+$, and are optionally substituted by one or more groups selected from a $(C_1$-$C_6)$alkyl, $(C_1$-$C_6)$haloalkyl, $OR_{56}$, $SR_{57}$ and $NR_{58}R_{59}$ group, wherein $R_{56}$ to $R_{99}$ each represent, independently of each other, a hydrogen atom or a $(C_1$-$C_6)$alkyl group;

advantageously, said heterocycle is selected from the group consisting of aziridine, azetidine, pyrrolidine, piperidine, piperazine, morpholine, thiomorpholine, 1H-azirine, pyrroline and indoline;

still advantageously, said heteroaryl is selected from the group consisting of pyrrole, indole, julolidine and carbazole; and said aryl is para-substituted by a $NR_{60}R_{61}$ group, wherein $R_{60}$ and $R_{61}$ each represent, independently of each other, a hydrogen atom, or a methyl, ethyl, n-propyl, isopropyl, n-butyl, isobutyl, sec-butyl, tert-butyl, phenyl, benzyl, cyclohexyl, cyclopentyl or cyclopropyl group, and optionally substituted by one or more groups selected from a $(C_1$-$C_6)$alkyl, $(C_1$-$C_6)$haloalkyl, $OR_{66}$, $SR_{67}$ and $NR_{68}R_{69}$ group, wherein $R_{66}$ to $R_{69}$ each represent, independently of each other, a hydrogen atom or a ($C_1$-$C_6$)alkyl group; advantageously, said aryl is a phenyl, a naphthyl, or an anthracenyl.

In a preferred embodiment X and X' each represent, independently of each other, $NR_{50}R_{51}$, wherein $R_{50}$ and $R_{51}$ each represent, independently of each other, a hydrogen atom, or a methyl, ethyl, n-propyl, isopropyl, tert-butyl, phenyl, benzyl, cyclohexyl, cyclopentyl or cyclopropyl group, said group being optionally substituted by one or more groups selected from a halogen atom, a ($C_1$-$C_6$)alkyl, $OR_{85}$, $SR_{86}$ and $NR_{87}R_{88}$ group, wherein $R_{85}$ to $R_{88}$ each represent, independently of each other, a hydrogen atom or a ($C_1$-$C_6$)alkyl group, notably a methyl, ethyl or n-propyl group; preferably, $R_{50}$ and $R_{51}$ are the same.

Preferably, X and X' are the same.

In a particular embodiment, $A^-$ represents a hexafluorophosphate, tetrafluoroborate, tetraphenylborate, $DDQH^-$, halide or triflate anion, preferably a $DDQH^-$ or hexafluorophosphate anion, notably a hexafluorophosphate anion.

In a particular embodiment:

$L_X$ and $L_{X'}$ each represent, independently of each other, a bond or a group selected from the group consisting of:

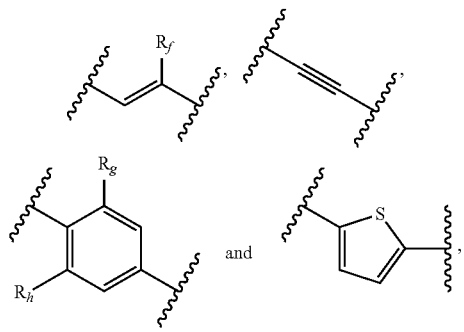

wherein $R_f$, $R_g$ and $R_h$ each represent a hydrogen atom; and X and X' each represent, independently of each other, $NR_{50}R_{51}$, heterocycle, heteroaryl or aryl, wherein:
said heterocycle and heteroaryl comprise at least one nitrogen atom bearing a lone pair of electrons conjugated with $C^+$, and are optionally substituted by one or more groups selected from a halogen atom, a ($C_1$-$C_6$) alkyl, ($C_1$-$C_6$)haloalkyl, $OR_{56}$, $SR_{57}$ and $NR_{58}R_{59}$ group, and
said aryl is para-substituted by a $NR_{60}R_{61}$ group, and optionally substituted by one or more groups selected from a halogen atom, a ($C_1$-$C_6$)alkyl, ($C_1$-$C_6$)haloalkyl, $OR_{66}$, $SR_{67}$ and $NR_{68}R_{69}$ group.

In a preferred embodiment, $L_X=L_{X'}$ and X=X'.

In yet another preferred embodiment, $L_X=L_{X'}$ and X=X', wherein $L_X$ and $L_{X'}$ each represent a bond, and X and X' each represent $NR_{50}R_{51}$, wherein $R_{50}$ and $R_{51}$ each represent, independently of each other, a hydrogen atom, or a methyl, ethyl, n-propyl, isopropyl, tert-butyl, phenyl, benzyl, cyclohexyl, cyclopentyl or cyclopropyl group, said group being optionally substituted by one or more groups selected from a halogen atom, a ($C_1$-$C_6$)alkyl, $OR_{85}$, $SR_{86}$ and $NR_{87}R_{88}$ group, wherein $R_{85}$ to $R_{88}$ each represent, independently of each other, a hydrogen atom or a ($C_1$-$C_6$)alkyl group, notably a methyl, ethyl or n-propyl group; preferably, $R_{50}$ and $R_{51}$ are the same.

In a particular embodiment, $L_X=L_{X'}$, X=X', $R_1=R_1'$, $R_2=R_2$, $R_3=R_3'$, and $R_4=R_4'$.

According to a particular embodiment, $R_0$ is as defined above;

$R_1=R_1'$, and $R_1$ represents a halogen atom, a ($C_1$-$C_6$) alkyl, ($C_2$-$C_6$)alkenyl, ($C_2$-$C_6$)alkynyl, ($C_1$-$C_6$)haloalkyl, aryl, heteroaryl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$)alkyl, $(CH_2)_mOR_{24}$, $(CH_2)_mSR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;

$R_4=R_4'$, and $R_4$ represents a halogen atom, a ($C_1$-$C_6$) alkyl, ($C_2$-$C_6$)alkenyl, ($C_2$-$C_6$)alkynyl, ($C_1$-$C_6$)haloalkyl, aryl, heteroaryl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$)alkyl, $(CH_2)_mOR_{24}$, $(CH_2)_mSR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;
with the proviso that when $R_1$ and $R_4$ are the same, at least one of $R_a$ and $R_e$ is not the same as $R_1$;

$R_2=R_2'$, $R_3=R_3'$, and $R_2$ and $R_3$ each represent, independently of each other, a hydrogen atom, a halogen atom, a ($C_1$-$C_6$)alkyl, ($C_2$-$C_6$)alkenyl, ($C_2$-$C_6$)alkynyl, ($C_1$-$C_6$)haloalkyl, aryl, heteroaryl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$)alkyl, $OR_{42}$, $SR_{43}$, $NR_{44}R_{45}$, $COR_{46}$, $CO_2R_{47}$ or $CONR_{48}R_{49}$ group, preferably a hydrogen atom;

$L_X=L_{X'}$, and $L_X$ represents a bond, or a group selected from the group consisting of:

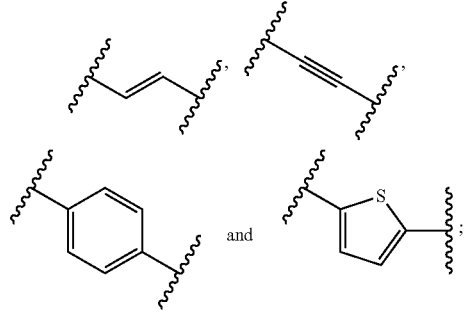

X=X', and X represents $NR_{50}R_{51}$, heterocycle, heteroaryl or aryl, wherein:
said heterocycle and heteroaryl group comprise at least one nitrogen atom bearing a lone pair of electrons conjugated with $C^+$, and are optionally substituted by one or more groups selected from a halogen atom, a ($C_1$-$C_6$)alkyl, ($C_1$-$C_6$)haloalkyl, $OR_{56}$, $SR_{57}$ and $NR_{58}R_{59}$ group, and
said aryl is para-substituted by a $NR_{60}R_{61}$ group, and optionally substituted by one or more groups selected from a halogen atom, a ($C_1$-$C_6$)alkyl, ($C_1$-$C_6$)haloalkyl, $OR_{66}$, $SR_{67}$ and $NR_{68}R_{69}$ group;

or $L_X=L_{X'}$ and $L_X$ represents a bond; X=X' and X represents $NR_{50}'R_{51}'$, $PR_{52}'R_{53}'$, $OR_{54}'$ or $SR_{55}'$; and $R_2$ and $NR_{50}'$, and $R_2'$ and $NR_{50}'$; $R_2$ and $PR_{52}'$, and $R_2'$ and $PR_{52}'$; $R_2$ and $OR_{54}'$, and $R_2'$ and $OR_{54}'$; or $R_2$ and $SR_{55}'$, and $R_2'$ and $SR_{55}'$ form together with the carbon atoms that carry them a heterocycle or heteroaryl group, said group being optionally substituted by one or more groups selected from a halogen atom, $(C_1-C_6)$ alkyl, $(C_1-C_6)$haloalkyl, $OR_{81}$, $SR_{82}$ and $NR_{83}R_{84}$;

and/or $R_3$ and $NR_{51}'$, and $R_3'$ and $NR_{51}'$; $R_3$ and $PR_{53}'$, and $R_3'$ and $PR_{53}'$; $R_3$ and $OR_{54}'$, and $R_3'$ and $OR_{54}'$; or $R_3$ and $SR_{55}'$, and $R_3'$ and $SR_{55}'$ form together with the carbon atoms that carry them a heterocycle or heteroaryl group, said group being optionally substituted by one or more groups selected from a halogen atom, $(C_1-C_6)$ alkyl, $(C_1-C_6)$haloalkyl, $OR_{81}$, $SR_{82}$ and $NR_{83}R_{84}$;

and $R_{50}'$, $R_{51}'$, $R_{52}'$ and $R_{53}'$ represent respectively $R_{50}$, $R_{51}$, $R_{52}$ and $R_{53}$ when they are not linked with $R_2$ or $R_3$;

and $R_5$ to $R_{88}$ are as defined above;

and $A^-$ is as defined above.

In a first embodiment, $L_X$ and $L_{X'}$ both represent a bond, and thus the compounds according to the invention have the following formula:

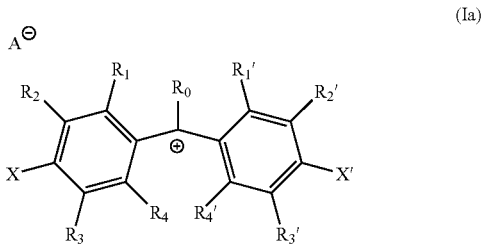

(Ia)

wherein:

$R_0$ represents a hydrogen atom, or is selected from the group consisting of:

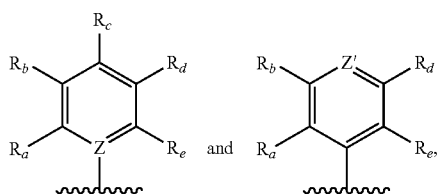

wherein Z represents C or $N^+ A_z^-$ and Z' represents N or $N^+$—$R_c'$ $A_z^-$, wherein $A_z^-$ represents a hexafluorophosphate, tetrafluoroborate, tetraphenylborate, DDQH$^-$, halide or triflate anion; $R_a$ and $R_e$ are the same, and represent a methyl, phenyl or methoxy group; and $R_b$, $R_c$ and $R_d$ are a hydrogen atom;

$R_1=R_4=R_1'=R_4'$, and $R_1$ represents a $(C_1-C_6)$alkyl, $(C_1-C_6)$haloalkyl, aryl, $(CH_2)_m OR_{24}$, $(CH_2)_m SR_{25}$, $OR_{26}$ or $SR_{27}$ group;

$R_2=R_2'=R_3=R_3'$ and each represent a hydrogen or halogen atom, or a $(C_1-C_6)$alkyl group, notably a methyl, ethyl or n-propyl group;

X=X' and each represent $NR_{50}R_{51}$, heterocycle, heteroaryl or aryl, wherein:

said heterocycle and heteroaryl comprise at least one nitrogen atom bearing a lone pair of electrons conjugated with C$^+$, and are optionally substituted by one or more groups selected from a halogen atom, a $(C_1-C_6)$alkyl, $(C_1-C_6)$haloalkyl, $OR_{56}$, $SR_{57}$ and $NR_{58}R_{59}$ group, and said aryl is para-substituted by a $NR_{60}R_{61}$ group, and optionally substituted by one or more groups selected from a halogen atom, a $(C_1-C_6)$alkyl, $(C_1-C_6)$haloalkyl, $OR_{66}$, $SR_{67}$ and $NR_{68}R_{69}$ group;

$A^-$ represents a hexafluorophosphate, tetrafluoroborate, tetraphenylborate, DDQH$^-$, halide or triflate anion, preferably a DDQH$^-$ or hexafluorophosphate anion, notably a hexafluorophosphate anion.

In a second embodiment, $L_X$ and $L_{X'}$ both represent a bond, and thus the compounds according to the invention correspond to formula (Ia), wherein:

$R_0$ represents a hydrogen atom;

$R_1=R_4=R_1'=R_4'$, and $R_1$ represents a methyl, ethyl, n-propyl, isopropyl, n-butyl, isobutyl, sec-butyl, tert-butyl, $CF_3$, phenyl, $CH_2OR_{24}$, $CH_2SR_{25}$, $OR_{26}$ or $SR_{27}$ group, wherein $R_{24}$ to $R_{27}$ each represent a hydrogen atom or a methyl, ethyl or n-propyl group;

$R_2$, $R_2'$, $R_3$ and $R_3'$ each represent a hydrogen atom;

X=X' each represent $NR_{50}R_{51}$, wherein $R_{50}$ and $R_{51}$ each represent, independently of each other, a hydrogen atom, or a methyl, n-propyl, isopropyl, tert-butyl, phenyl, benzyl, cyclohexyl, cyclopentyl or cyclopropyl group, said group being optionally substituted by one or more groups selected from a halogen atom, a $(C_1-C_6)$alkyl, $OR_{85}$, $SR_{86}$ and $NR_{87}R_{88}$ group, wherein $R_{85}$ to $R_{88}$ each represent, independently of each other, a hydrogen atom or a $(C_1-C_6)$alkyl group, notably a methyl, ethyl or n-propyl group; preferably, $R_{50}$ and $R_{51}$ are the same; and $A^-$ represents a hexafluorophosphate, tetrafluoroborate, tetraphenylborate, DDQH$^-$, halide or triflate anion, preferably a DDQH$^-$ or hexafluorophosphate anion, notably a hexafluorophosphate anion.

According to a particular embodiment, $R_4$ and $R_4'$ form together a bond or a chain selected from the group consisting of —$C(R_{74}R_{75})$—, —$(CH_2)_n$—, —$Si(R_{76}R_{77})$—, —$(CH_2)_p$—Y—$(CH_2)_q$— and —Y—$(CR_{78}R_{79})_r$—Y'—.

According to another particular embodiment, $R_4$ and $R_4'$ form together a chain selected from the group consisting of —$C(R_{74}R_{75})$— and —$Si(R_{76}R_{77})$—, wherein:

$R_{74}$ and $R_{75}$ each represent, independently of each other, a hydrogen atom, a $(C_1-C_6)$alkyl or an aryl group, notably a hydrogen atom or a methyl, ethyl, n-propyl or phenyl group; and $R_{76}$ and $R_{77}$ each represent, independently of each other, a $(C_1-C_6)$alkyl or an aryl group, notably a methyl, ethyl, n-propyl or phenyl group.

In a preferred embodiment, $R_4$ and $R_4'$ form together a bond or a chain selected from the group consisting of —$(CH_2)_n$—, —$(CH_2)_p$—Y—$(CH_2)_q$— and —Y—$(CR_{78}R_{79})_r$—Y'—, wherein Y and Y' each represent, independently of each other, O, S or $NR_{80}$; n is equal to 2 or 3; p is equal to 1 or 2; q is equal to 0 or 1; preferably, p=q=1; r is equal to 1 or 2; and $R_{78}$ to $R_{80}$ each represent, independently of each other, a $(C_1-C_6)$alkyl or an aryl group, notably a methyl, ethyl, n-propyl or phenyl group.

In a particular embodiment, $L_X=L_{X'}$ and each represent a bond or a group selected from the group consisting of:

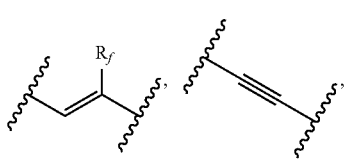

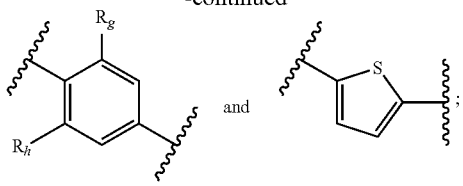

and

R$_4$ and R$_4$' form together a bond or a chain selected from the group consisting of —C(R$_{74}$R$_{75}$)—, —(CH$_2$)$_n$—, —Si(R$_{76}$R$_{77}$)—, —(CH$_2$)$_p$—Y—(CH$_2$)$_q$— and —Y—(CR$_{78}$R$_{79}$)$_r$—Y'—.

In a particular embodiment, L$_X$ and L$_{X'}$ both represent a bond and, a compound according to the invention can thus be represented by the following formula (II):

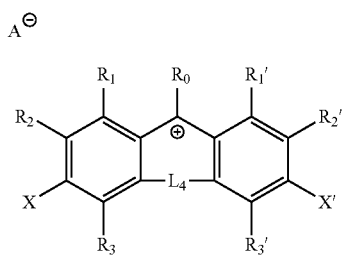

(II)

wherein:

L$_4$ represents a bond or a chain selected from the group consisting of —C(R$_{74}$R$_{75}$)—, —(CH$_2$)$_n$—, —Si(R$_{76}$R$_{77}$)—, —(CH$_2$)$_p$—Y—(CH$_2$)$_q$— and —Y—(CR$_{78}$R$_{79}$)$_r$—Y'—, preferably a bond or a chain selected from the group consisting of —(CH$_2$)$_n$—, —(CH$_2$)$_p$—Y—(CH$_2$)$_q$— and —Y—(CR$_{78}$R$_{79}$)$_r$—Y'—, wherein Y, Y', n, p, q, r and R$_{74}$ to R$_{79}$ are as defined above; and R$_0$, R$_1$, R$_2$, R$_3$, R$_1$', R$_2$', R$_3$', X and X' are as defined above.

Advantageously, L$_4$ can represent a bond, or a chain selected from the group consisting of —(CH$_2$)$_2$—, —(CH$_2$)$_3$—, —CH$_2$—NR$_{74}$—CH$_2$—, —O—CR$_{78}$R$_{79}$—O— and —O—(CH$_2$)$_2$—O—.

In a particular embodiment, a compound according to the invention is represented by formula (II), wherein R$_2$, R$_2$', R$_3$ and R$_3$' each represent a hydrogen atom.

In another particular embodiment, a compound according to the invention is represented by formula (II), wherein R$_1$=R$_1$', and R$_1$ represents a (C$_1$-C$_6$)alkyl, (C$_1$-C$_6$)haloalkyl, aryl, (CH$_2$)$_m$OR$_{24}$, (CH$_2$)$_m$SR$_{25}$, OR$_{26}$ or SR$_{27}$ group; preferably a methyl, ethyl, n-propyl, isopropyl, n-butyl, isobutyl, sec-butyl, tert-butyl, CF$_3$, phenyl, CH$_2$OR$_{24}$, CH$_2$SR$_{25}$, OR$_{26}$ or SR$_{27}$ group, wherein R$_{24}$ to R$_{27}$ each represent a hydrogen atom or a methyl, ethyl or n-propyl group; more preferably a CH$_2$OR$_{24}$ or OR$_{26}$ group, wherein R$_{24}$ and R$_{26}$ represent a hydrogen atom or a methyl, ethyl or n-propyl group; even more preferably, R$_1$ represents a methoxy group.

In still another particular embodiment, a compound according to the invention is represented by formula (II), wherein X=X' and each represent NR$_{50}$R$_{51}$, heterocycle, heteroaryl or aryl, wherein:

said heterocycle and heteroaryl comprise at least one nitrogen atom bearing a lone pair of electrons conjugated with C$^+$, and are optionally substituted by one or more groups selected from a halogen atom, a (C$_1$-C$_6$)alkyl, (C$_1$-C$_6$)haloalkyl, OR$_{56}$, SR$_{57}$ and NR$_{58}$R$_{59}$ group, and said aryl is para-substituted by a NR$_{60}$R$_{61}$ group, and optionally substituted by one or more groups selected from a halogen atom, a (C$_1$-C$_6$)alkyl, (C$_1$-C$_6$)haloalkyl, OR$_{66}$, SR$_{67}$ and NR$_{68}$R$_{69}$ group.

In a third embodiment, according to the invention is represented by formula (II), wherein:

L$_4$ represents a bond or a chain selected from the group consisting of —C(R$_{74}$R$_{75}$)—, —(CH$_2$)$_n$—, —Si(R$_{76}$R$_{77}$)—, —(CH$_2$)$_p$—Y—(CH$_2$)$_q$— and —Y—(CR$_{78}$R$_{79}$)$_r$—Y'—, preferably a bond or a chain selected from the group consisting of —(CH$_2$)$_n$—, —(CH$_2$)$_p$—Y—(CH$_2$)$_q$— and —Y—(CR$_{78}$R$_{79}$)$_r$—Y'—, wherein Y, Y', n, p, q, r and R$_{74}$ to R$_{79}$ are as defined above;

R$_0$ represents a hydrogen atom;

R$_1$=R$_1$', and R$_1$ represents a methyl, ethyl, n-propyl, isopropyl, n-butyl, isobutyl, sec-butyl, tert-butyl, CF$_3$, phenyl, CH$_2$OR$_{24}$, CH$_2$SR$_{25}$, OR$_{26}$ or SR$_{27}$ group, wherein R$_{24}$ to R$_{27}$ each represent a hydrogen atom or a methyl, ethyl or n-propyl group;

R$_2$, R$_2$', R$_3$ and R$_3$' each represent a hydrogen atom;

X=X' each represent NR$_{50}$R$_{51}$, wherein R$_{50}$ and R$_{51}$ each represent, independently of each other, a hydrogen atom, or a methyl, ethyl, n-propyl, isopropyl, tert-butyl, phenyl, benzyl, cyclohexyl, cyclopentyl or cyclopropyl group, said group being optionally substituted by one or more groups selected from a halogen atom, a (C$_1$-C$_6$)alkyl, OR$_{85}$, SR$_{86}$ and NR$_{87}$R$_{88}$ group, wherein R$_{85}$ to R$_{88}$ each represent, independently of each other, a hydrogen atom or a (C$_1$-C$_6$)alkyl group, notably a methyl, ethyl or n-propyl group; preferably, R$_{50}$ and R$_{51}$ are the same; and A$^-$ represents a hexafluorophosphate, tetrafluoroborate, tetraphenylborate, halide, DDQH$^-$ or triflate anion, preferably a DDQH$^-$ or hexafluorophosphate anion, notably a hexafluorophosphate anion.

In a particular embodiment:

L$_X$ represents a bond; X represents NR$_{50}$'R$_{51}$', PR$_{52}$'R$_{53}$', OR$_{54}$' or SR$_{55}$'; and R$_2$ and NR$_{50}$', R$_2$ and PR$_{52}$', R$_2$ and OR$_{54}$', R$_2$ and SR$_{55}$', R$_3$ and NR$_{51}$', R$_3$ and PR$_{53}$', R$_3$ and OR$_{54}$' and/or R$_3$ and SR$_{55}$', independently of each other, form together with the carbon atoms that carry them a heterocycle or heteroaryl group, said group being optionally substituted by one or more groups selected from a halogen atom, (C$_1$-C$_6$)alkyl, (C$_1$-C$_6$)haloalkyl, OR$_{81}$, SR$_{82}$ and NR$_{83}$R$_{84}$; and R$_{50}$', R$_{51}$', R$_{52}$' and R$_{53}$' represent respectively R$_{50}$, R$_{51}$, R$_{52}$ and R$_{53}$ when they are not linked with R$_2$ or R$_3$;

and/or

L$_{X'}$ represents a bond; X' represents NR$_{50}$'R$_{51}$', PR$_{52}$'R$_{53}$', OR$_{54}$' or SR$_{55}$'; and R$_2$' and NR$_{50}$', R$_2$' and PR$_{52}$', R$_2$' and OR$_{54}$', R$_2$' and SR$_{55}$', R$_3$' and NR$_{51}$', R$_3$' and PR$_{53}$', R$_3$' and OR$_{54}$' and/or R$_3$' and SR$_{55}$', independently of each other, form together with the carbon atoms that carry them a heterocycle or heteroaryl group, said group being optionally substituted by one or more groups selected from a halogen atom, (C$_1$-C$_6$)alkyl, (C$_1$-C$_6$)haloalkyl, OR$_{81}$, SR$_{82}$ and NR$_{83}$R$_{84}$; and R$_{50}$', R$_{51}$', R$_{52}$' and R$_{53}$' represent respectively R$_{50}$, R$_{51}$, R$_{52}$ and R$_{53}$ when they are not linked with R$_2$ or R$_3$.

In another particular embodiment:

L$_X$ represents a bond; X represents NR$_{50}$'R$_{51}$'; and R$_2$ and NR$_{50}$', and/or R$_3$ and NR$_{51}$', independently of each other, form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$; and $R_{50}'$ and $R_{51}'$ represent respectively $R_{50}$ and $R_{51}$ when they are not linked with $R_2$ or $R_3$;

and/or $L_{X'}$ represents a bond; X' represents $NR_{50}'R_{51}'$; and $R_2'$ and $NR_{50}'$, and/or $R_3'$ and $NR_{51}'$, independently of each other, form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$; and $R_{50}'$ and $R_{51}'$ represent respectively $R_{50}$ and $R_{51}$ when they are not linked with $R_2$ or $R_3$;

$R_{81}$ to $R_{84}$ each represent, independently of each other, a hydrogen atom or a $(C_1-C_6)$alkyl.

In still another particular embodiment:

$L_X$ represents a bond; X represents $NR_{50}'R_{51}'$; and $R_2$ and $NR_{50}'$, and/or $R_3$ and $NR_{51}'$, independently of each other, form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$; wherein:

said heterocycle is selected from the group consisting of pyrrolidine, thiazolidine, isothiazolidine, oxazolidine, isoxazolidine, imidazolidine, pyrazolidine, triazolidine, piperidine, piperazine, morpholine, thiomorpholine, 1H-azirine, pyrroline, thiazoline, isothiazoline, oxazoline, isoxazoline, imidazoline, pyrazoline, triazoline, dihydropyridine, tetrahydropyridine, dihydropyrimidine, tetrahydropyrimidine, dihydropyridazine, tetrahydropyridazine, dihydropyrazine, tetrahydropyrazine, dihydrotriazine, tetrahydrotriazine, indoline, 1,3-benzoxathiole, benzoxazoline, benzothiazoline and benzimidazoline; and said heteroaryl is selected from the group consisting of pyrrole, thiazole, isothiazole, oxazole, isoxazole, imidazole, pyrazole, triazole, pyridine, pyrimidine, indole, benzothiazole, benzoxazole, benzimidazole, indazole, benzotriazole, quinoline, isoquinoline, cinnoline, quinazoline, quinoxaline and carbazole;

and/or $L_{X'}$ represents a bond; X' represents $NR_{50}'R_{51}'$; and $R_2'$ and $NR_{50}'$, and/or $R_3'$ and $NR_{51}'$, independently of each other, form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$; wherein:

said heterocycle is selected from the group consisting of pyrrolidine, thiazolidine, isothiazolidine, oxazolidine, isoxazolidine, imidazolidine, pyrazolidine, triazolidine, piperidine, piperazine, morpholine, thiomorpholine, 1H-azirine, pyrroline, thiazoline, isothiazoline, oxazoline, isoxazoline, imidazoline, pyrazoline, triazoline, dihydropyridine, tetrahydropyridine, dihydropyrimidine, tetrahydropyrimidine, dihydropyridazine, tetrahydropyridazine, dihydropyrazine, tetrahydropyrazine, dihydrotriazine, tetrahydrotriazine, indoline, 1,3-benzoxathiole, benzoxazoline, benzothiazoline and benzimidazoline; and said heteroaryl is selected from the group consisting of pyrrole, thiazole, isothiazole, oxazole, isoxazole, imidazole, pyrazole, triazole, pyridine, pyrimidine, indole, benzothiazole, benzoxazole, benzimidazole, indazole, benzotriazole, quinoline, isoquinoline, cinnoline, quinazoline, quinoxaline and carbazole;

$R_{81}$ to $R_{84}$ each represent, independently of each other, a hydrogen atom or a $(C_1-C_6)$alkyl.

In yet another particular embodiment:

$L_X$ represents a bond; X represents $NR_{50}'R_{51}'$; and $R_2$ and $NR_{50}'$, and/or $R_3$ and $NR_{51}'$, independently of each other, form together with the carbon atoms that carry them a heterocycle or heteroaryl group, said group being optionally substituted by one or more groups selected from $(C_1-C_6)$alkyl, $OR_{81}$ and $NR_{83}R_{84}$, wherein:

said heterocycle is selected from the group consisting of pyrrolidine, imidazolidine, pyrazolidine, piperidine, piperazine, morpholine, pyrroline, imidazoline, pyrazoline, triazoline, dihydropyridine, tetrahydropyridine, dihydropyrimidine, tetrahydropyrimidine, dihydropyridazine, tetrahydropyridazine, dihydropyrazine, tetrahydropyrazine, dihydrotriazine and tetrahydrotriazine; and said heteroaryl is selected from the group consisting of pyrrole, imidazole, pyrazole, triazole, pyridine and pyrimidine;

and/or $L_{X'}$ represents a bond; X' represents $NR_{50}'R_{51}'$; and $R_2'$ and $NR_{50}'$, and/or $R_3'$ and $NR_{51}'$, independently of each other, form together with the carbon atoms that carry them a heterocycle or heteroaryl group, said group being optionally substituted by one or more groups selected from $(C_1-C_6)$alkyl, $OR_{81}$ and $NR_{83}R_{84}$; wherein:

said heterocycle is selected from the group consisting of pyrrolidine, imidazolidine, pyrazolidine, piperidine, piperazine, morpholine, pyrroline, imidazoline, pyrazoline, triazoline, dihydropyridine, tetrahydropyridine, dihydropyrimidine, tetrahydropyrimidine, dihydropyridazine, tetrahydropyridazine, dihydropyrazine, tetrahydropyrazine, dihydrotriazine and tetrahydrotriazine; and said heteroaryl is selected from the group consisting of pyrrole, imidazole, pyrazole, triazole, pyridine and pyrimidine;

$R_{81}$ to $R_{84}$ each represent, independently of each other, a hydrogen atom or a $(C_1-C_6)$alkyl, notably a methyl, ethyl or n-propyl group.

In a particular embodiment:

$L_X=L_{X'}$ and $L_X$ represents a bond; X=X' and X represents $NR_{50}'R_{51}'$; and $R_2$ and $NR_{50}'$, $R_2'$ and $NR_{50}'$, $R_3$ and $NR_{51}'$, and $R_3'$ and $NR_{51}'$ form together with the carbon atoms that carry them a heterocycle group.

In a fourth embodiment, $L_X$ and $L_{X'}$ both represent a bond, and thus the compounds according to the invention correspond to formula (Ia), wherein:

$R_0$ represents a hydrogen atom, or is selected from the group consisting of:

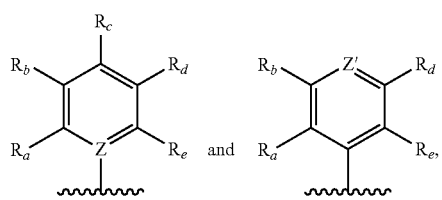

wherein Z represents C or N⁺A$_z$⁻ and Z' represents N or N⁺—R$_c$'A$_z$⁻, wherein A$_z$⁻ represents a hexafluorophosphate, tetrafluoroborate, tetraphenylborate, DDQH⁻, halide or triflate anion; R$_a$ and R$_e$ are the same, and represent a methyl, phenyl or methoxy group; and R$_b$, R$_c$ and R$_d$ are a hydrogen atom;

R$_1$=R$_4$=R$_1$'=R$_4$', and R$_1$ represents a (C$_1$-C$_6$)alkyl, (C$_1$-C$_6$)haloalkyl, aryl, (CH$_2$)$_m$OR$_{24}$, (CH$_2$)$_m$SR$_{25}$, OR$_{26}$ or SR$_{27}$ group;

X represents NR$_{50}$'R$_{51}$'; and R$_2$ and NR$_{50}$', and/or R$_3$ and NR$_{51}$', independently of each other, form together with the carbon atoms that carry them a heterocycle or heteroaryl group, said group being optionally substituted by one or more groups selected from a halogen atom, (C$_1$-C$_6$)alkyl, (C$_1$-C$_6$)haloalkyl, OR$_5$, SR$_{82}$ and NR$_{83}$R$_{84}$;

and/or

X' represents NR$_{50}$'R$_{51}$'; and R$_2$' and NR$_{50}$', and/or R$_3$' and NR$_{51}$', independently of each other, form together with the carbon atoms that carry them a heterocycle or heteroaryl group, said group being optionally substituted by one or more groups selected from a halogen atom, (C$_1$-C$_6$)alkyl, (C$_1$-C$_6$)haloalkyl, OR$_5$, SR$_{82}$ and NR$_{83}$R$_{84}$;

A⁻ represents a hexafluorophosphate, tetrafluoroborate, tetraphenylborate, DDQH⁻, halide or triflate anion, preferably a DDQH⁻ or hexafluorophosphate anion, notably a hexafluorophosphate anion.

In a fifth embodiment, L$_X$ and L$_{X'}$ both represent a bond, and thus the compounds according to the invention correspond to formula (Ia), wherein:

R$_0$ represents a hydrogen atom;

R$_1$=R$_4$=R$_1$'=R$_4$', and R$_1$ represents a methyl, ethyl, n-propyl, isopropyl, n-butyl, iso-butyl, sec-butyl, tert-butyl, CF$_3$, phenyl, CH$_2$OR$_{24}$, CH$_2$SR$_{25}$, OR$_{26}$ or SR$_{27}$ group, wherein R$_{24}$ to R$_{27}$ each represent a hydrogen atom or a methyl, ethyl or n-propyl group;

X represents NR$_{50}$'R$_{51}$'; and R$_2$ and NR$_{50}$', and/or R$_3$ and NR$_{51}$', independently of each other, form together with the carbon atoms that carry them a heterocycle or heteroaryl group, said group being optionally substituted by one or more groups selected from a halogen atom, (C$_1$-C$_6$)alkyl, (C$_1$-C$_6$)haloalkyl, OR$_5$, SR$_{82}$ and NR$_{83}$R$_{84}$; and/or X' represents NR$_{50}$'R$_{51}$'; and R$_2$' and NR$_{50}$', and/or R$_3$' and NR$_{51}$', independently of each other, form together with the carbon atoms that carry them a heterocycle or heteroaryl group, said group being optionally substituted by one or more groups selected from a halogen atom, (C$_1$-C$_6$)alkyl, (C$_1$-C$_6$)haloalkyl, OR$_{81}$, SR$_{82}$ and NR$_{83}$R$_{84}$;

R$_{81}$ to R$_{84}$ each represent, independently of each other, a hydrogen atom or a (C$_1$-C$_6$)alkyl, notably a methyl, ethyl or n-propyl group;

A⁻ represents a hexafluorophosphate, tetrafluoroborate, tetraphenylborate, DDQH⁻, halide or triflate anion, preferably a DDQH⁻ or hexafluorophosphate anion, notably a hexafluorophosphate anion.

In a particular embodiment, L$_X$ and L$_{X'}$ both represent

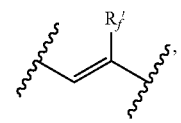

and

R$_2$ and R$_f$', and R$_2$' and R$_f$', independently of each other, form together with the carbon atoms that carry them a cycloalkenyl or aryl group, notably a cyclohexadienyl or phenyl group.

In another particular embodiment, L$_X$ and L$_{X'}$ both represent

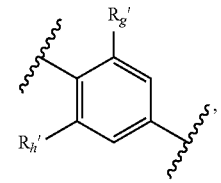

and

R$_2$ and R$_g$', R$_3$ and R$_h$', R$_2$' and R$_g$' and R$_3$' and R$_h$', independently of each other, form together with the carbon atoms that carry them a cycloalkenyl or aryl group, notably a cyclohexadienyl or phenyl group.

In a particular embodiment, a compound of the present invention is chosen among the following compounds:

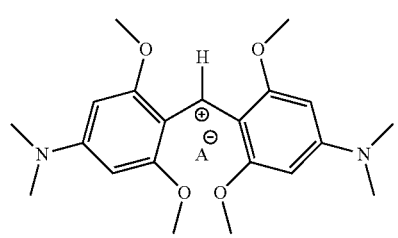

1

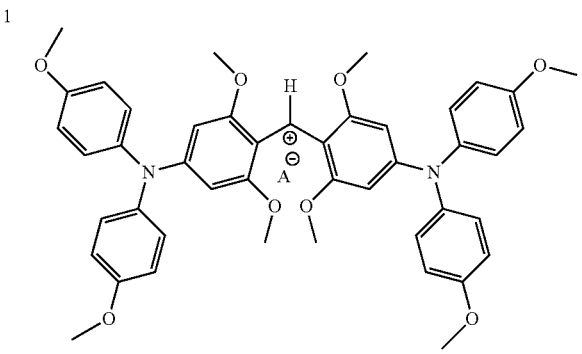

2

-continued
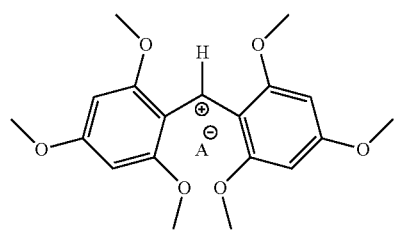 3
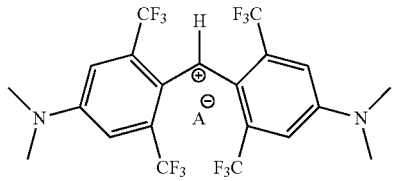 4
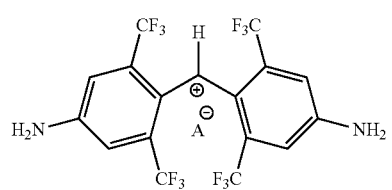 5
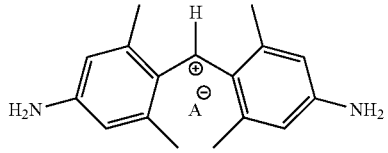 6
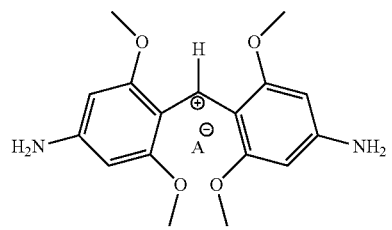 7
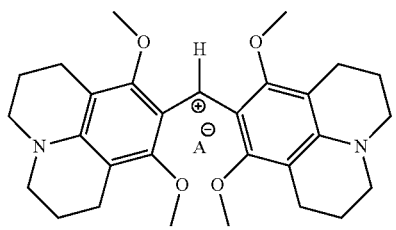 8
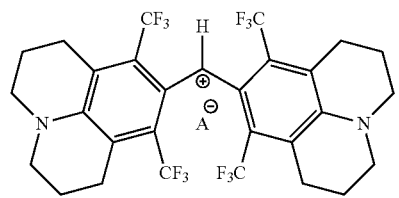 9
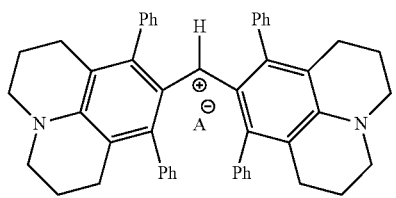 10
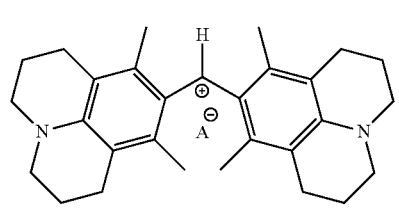 11
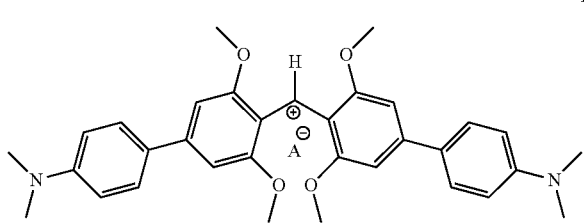 12
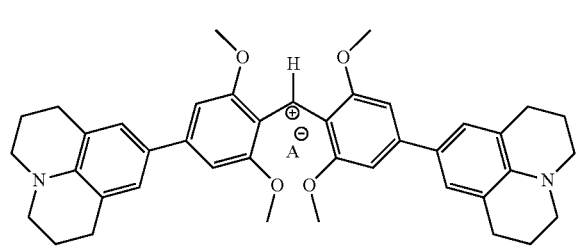 13
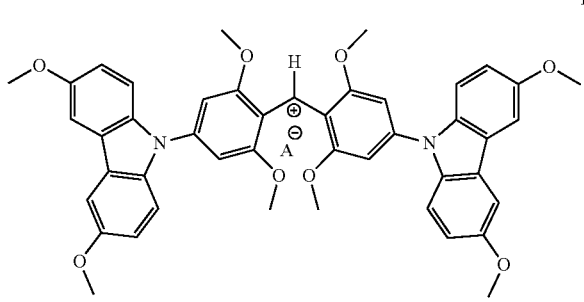 14
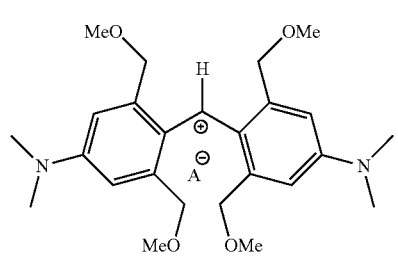 15
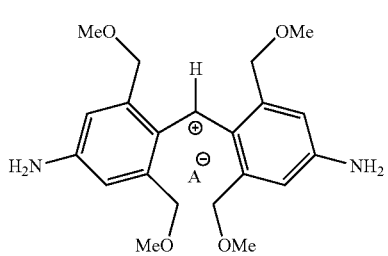 16

-continued
17
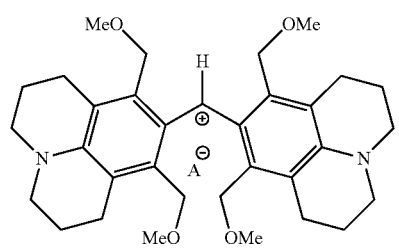
18
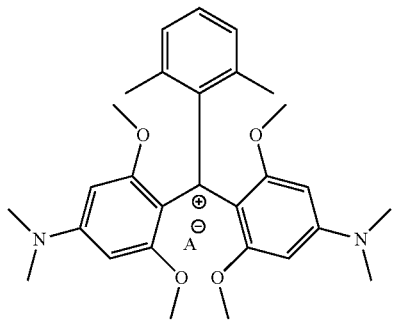
19
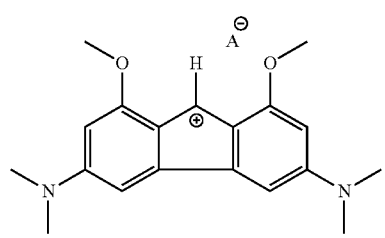
20
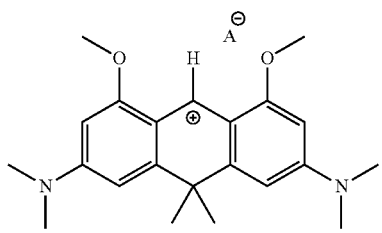
21
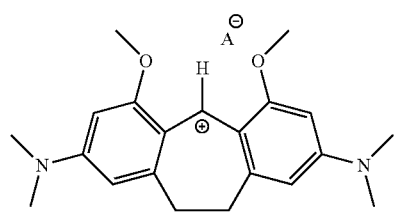
22
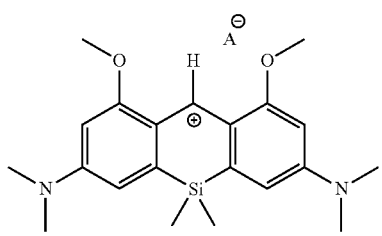
23
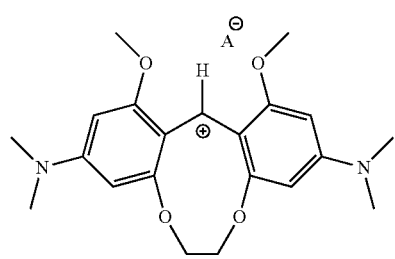
24
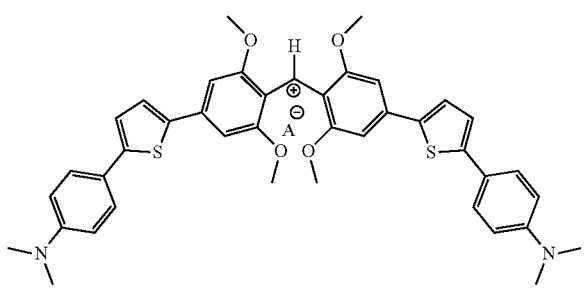
25
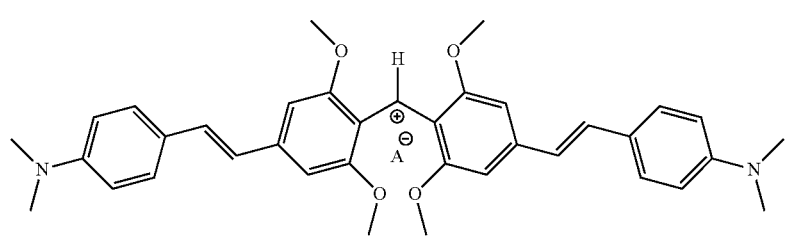
26
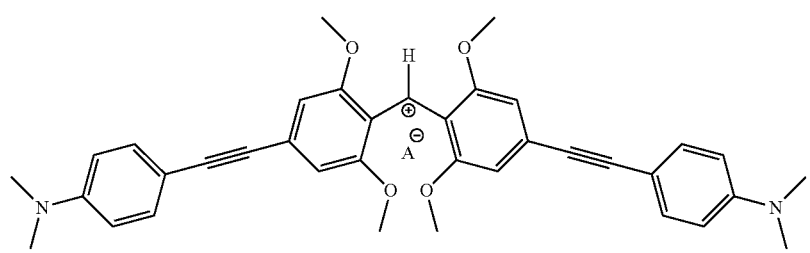

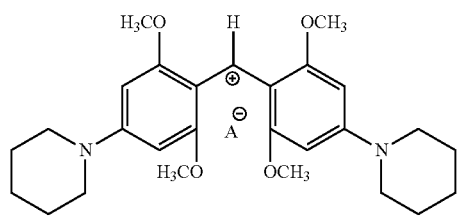
27

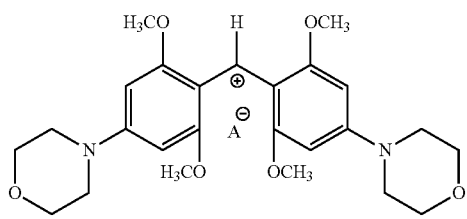
28

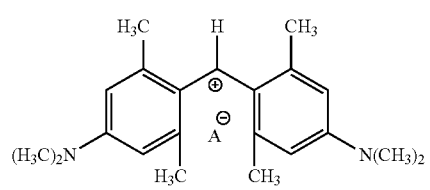
29

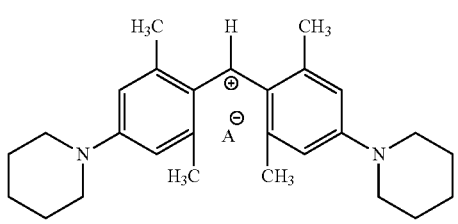
30

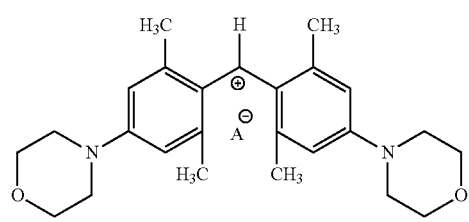
31

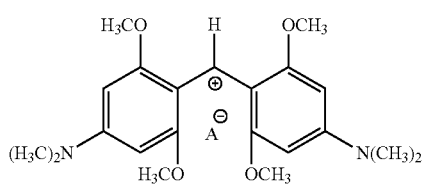
32 wherein A⁻ represents a hexafluorophosphate, tetrafluoroborate, tetraphenylborate, DDQH⁻, halide or triflate anion, preferably a DDQH⁻ or hexafluorophosphate anion, notably a hexafluorophosphate anion.

Notably, a compound of the present invention is chosen among compounds 1, 2, and 4 to 32.

Advantageously, a compound of the present invention is chosen among compounds 1, 2, 8, 11 and 27 to 32.

The invention also relates to the use of a compound according to the invention as a chromophore.

The term "chromophore" here refers to a molecule whose electronic absorption is at least situated in the spectral range of visible light (between ca. 400 nm and 700 nm), which is not exclusive of absorption in the near-UV and near-infrared domains.

The invention also relates to a material comprising at least one compound according to the invention.

As it has been previously mentioned, the compounds according to the invention tend to self-assemble and form supramolecular materials.

Said materials can be in the form of crystals, thin films, flakes, platelets or layers and other forms of low-dimensional materials that may result from self-assembly of chromophores.

Said supramolecular materials can be a pigment, advantageously a pigment of interest for its special optical effect(s).

Accordingly, the invention relates to the use of the compounds (or said supramolecular materials) according to the invention as a pigment.

Thus, the invention relates to the use as pigment of a compound of following general formula (I):

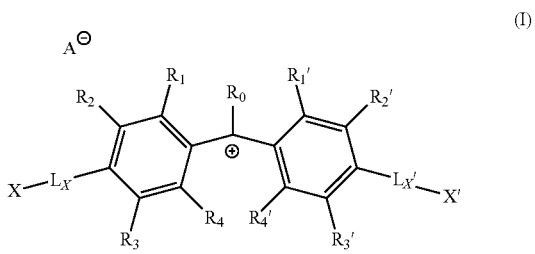

wherein:

$R_0$ represents a hydrogen atom, a halogen atom, a ($C_1$-$C_6$)alkyl, ($C_1$-$C_6$)haloalkyl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$)alkyl, $OR_5$, $SR_6$, $NR_7R_8$, $PR_9R_{10}$, $COR_{11}$, $CO_2R_{12}$, $CONR_{13}R_{14}$, $SO_2R_{15}$, $SO_3H$, $CN$, $NO_2$, $OCOR_{16}$, $OCO_2R_{17}$, $NR_{18}COR_{19}$ or $NR_{20}SO_2R_{21}$ group, or is selected from the group consisting of:

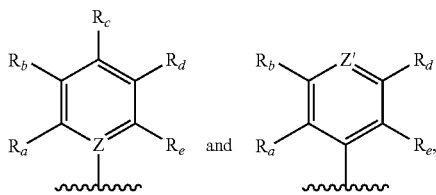

wherein:
- Z represents C or $N^+ A_z^-$ and Z' represents N or $N^+-R_c' A_z^-$, wherein
  - $A_z^-$ represents a monovalent organic or inorganic anion, and
  - $R_c'$ represents a hydrogen atom or a $(C_1-C_6)$alkyl group,
- $R_a$ and $R_e$ each represent, independently of each other, a halogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_{22}$ or $SR_{23}$ group, and
- $R_b$, $R_c$ and $R_d$ each represent, independently of each other, a hydrogen atom, a halogen atom or a $(C_1-C_6)$alkyl, $(C_1-C_6)$haloalkyl, cycloalkyl, cycloalkyl-$(C_1-C_6)$alkyl, heterocycle or heterocycle-$(C_1-C_6)$alkyl group;
- $R_1=R_1'$, and $R_1$ represents a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_mOR_{24}$, $(CH_2)_{m'}SR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;
- $R_4=R_4'$, and $R_4$ represents a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_mOR_{24}$, $(CH_2)_{m'}SR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;
- with the proviso that when $R_1$ and $R_4$ are the same, at least one of $R_a$ and $R_e$ is not the same as $R_1$;

or
- $R_4$ and $R_4'$ form together a bond or a chain selected from the group consisting of $-C(R_{74}R_{75})-$, $-(CH_2)_n-$, $-Si(R_{76}R_{77})-$, $-(CH_2)_p-Y-(CH_2)_q-$, and $-Y-(CR_{78}R_{79})_r-Y'-$, wherein:
  - Y and Y' each represent, independently of each other, O, S or $NR_{80}$,
  - n is equal to 2 or 3,
  - p is equal to 1 or 2,
  - q is equal to 0 or 1,
  - r is equal to 1 or 2,
  - $R_{74}$, $R_{75}$, $R_{78}$ to $R_{80}$ each represent, independently of each other, a hydrogen atom, a $(C_1-C_6)$alkyl or an aryl group, and
  - $R_{76}$ and $R_{77}$ each represent, independently of each other, a $(C_1-C_6)$alkyl or an aryl group;
- $R_2=R_2'$, $R_3=R_3'$, and $R_2$ and $R_3$ each represent, independently of each other, a hydrogen atom, a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_{42}$, $SR_{43}$, $NR_{44}R_{45}$, $COR_{46}$, $CO_2R_{47}$ or $CONR_{48}R_{49}$ group, preferably a hydrogen atom;
- $L_X=L_{X'}$, and $L_X$ represents a bond, or a group selected from the group consisting of:

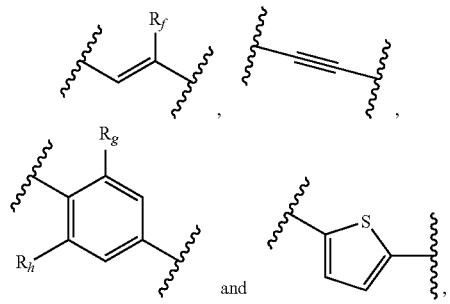

wherein $R_f$, $R_g$ and $R_h$ each represent, independently of each other, a hydrogen or halogen atom, a $(C_1-C_6)$alkyl or $(C_1-C_6)$haloalkyl group;
- X=X', and X represents $NR_{50}R_{51}$, $PR_{52}R_{53}$, $OR_{54}$, $SR_{55}$, heterocycle, heteroaryl or aryl, wherein:
  - said heterocycle and heteroaryl group comprise at least one heteroatom bearing a lone pair of electrons conjugated with $C^+$, and are optionally substituted by one or more groups selected from a halogen atom, $(C_1-C_6)$alkyl, $(C_1-C_6)$haloalkyl, $OR_{56}$, $SR_{57}$ and $NR_{58}R_{59}$, and
  - said aryl is para-substituted by a group selected from $NR_{60}R_{61}$, $PR_{62}R_{63}$, $OR_{64}$ and $SR_{65}$, and optionally substituted by one or more groups selected from a halogen atom, $(C_1-C_6)$alkyl, $(C_1-C_6)$haloalkyl, $OR_{66}$, $SR_{67}$ and $NR_{68}R_{69}$;

or
- $R_1$ together with $R_2$, and $R_1'$ together with $R_2'$ form with the carbon atoms that carry them an identical cycle selected from the group consisting of cycloalkenyl, heterocycle, aryl and heteroaryl, said cycle being optionally substituted by one or more groups selected from a halogen atom, $(C_1-C_6)$alkyl, $(C_1-C_6)$haloalkyl, $OR_{70}$, $SR_{71}$ and $NR_{72}R_{73}$;

and/or
- $R_3$ together with $R_4$, and $R_3'$ together with $R_4'$ form with the carbon atoms that carry them an identical cycle selected from the group consisting of cycloalkenyl, heterocycle, aryl and heteroaryl, said cycle being optionally substituted by one or more groups selected from a halogen atom, $(C_1-C_6)$alkyl, $(C_1-C_6)$haloalkyl, $OR_{70}$, $SR_{71}$ and $NR_{72}R_{73}$;

and/or
- $L_X=L_{X'}$ and $L_X$ represents a bond; X=X' and X represents $NR_{50}'R_{51}'$, $PR_{52}'R_{53}'$, $OR_{54}'$ or $SR_{55}'$; and
- $R_2$ and $NR_{50}'$, and $R_2'$ and $NR_{50}'$; $R_2$ and $PR_{52}'$, and $R_2'$ and $PR_{52}'$; $R_2$ and $OR_{54}'$, and $R_2'$ and $OR_{54}'$; or $R_2$ and $SR_{55}'$, and $R_2'$ and $SR_{55}'$ form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$;

and/or $R_3$ and $NR_{51}'$, and $R_3'$ and $NR_{51}'$; $R_3$ and $PR_{53}'$, and $R_3'$ and $PR_{53}'$; $R_3$ and $OR_{54}'$, and $R_3'$ and $OR_{54}'$; or $R_3$ and $SR_{55}'$, and $R_3'$ and $SR_{55}'$ form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$;

and $R_{50}'$, $R_{51}'$, $R_{52}'$ and $R_{53}'$ represent respectively $R_{50}$, $R_{51}$, $R_{52}$ and $R_{53}$ when they are not linked with $R_2$ or $R_3$;

and/or $L_X=L_{X'}$ and $L_x$ represents

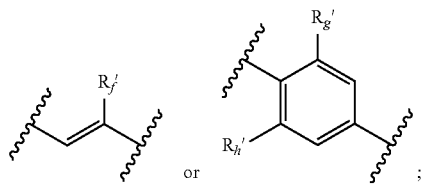

and $R_2$ and $R_f'$, and $R_2'$ and $R_f'$; or $R_2$ and $R_g'$ and $R_2'$ and $R_g'$ form together with the carbon atoms that carry them a cycloalkenyl or aryl group;

and/or $R_3$ and $R_g'$, and $R_3'$ and $R_g'$ form together with the carbon atoms that carry them a cycloalkenyl or aryl group;

and $R_f'$, $R_g'$ and $R_h'$ represent respectively $R_f$, $R_g$ and $R_h$ when they are not linked with $R_2$ or $R_3$;

and $R_5$ to $R_{53}$, $R_{56}$ to $R_{63}$, $R_{66}$ to $R_{73}$ and $R_{81}$ to $R_{84}$ each represent, independently of each other, a hydrogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1-C_6)$alkyl group;

and $R_{54}$, $R_{55}$, $R_{64}$ and $R_{65}$ each represent, independently of each other, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1-C_6)$alkyl group;

and $A^-$ represents a monovalent or multivalent, organic or inorganic anion.

In a particular embodiment:

$R_0$ represents a hydrogen atom, a $(C_1-C_6)$alkyl, $NR_7R_8$, CN, $CF_3$ or $NO_2$ group, or is selected from the group consisting of:

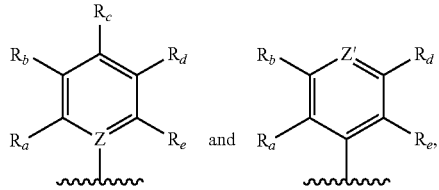

wherein:

$R_a$ and $R_e$ each represent, independently of each other, a methyl, $OCH_3$ or phenyl group, and $R_b$, $R_c$ and $R_d$ each represent a hydrogen atom;

preferably $R_0$ represents a hydrogen atom or a CN group, notably a hydrogen atom;

$R_1=R_4$ and $R_1$ represents a $(C_1-C_6)$alkyl, $(C_1-C_6)$haloalkyl, aryl, $CH_2OR_{24}$, $CH_2SR_{25}$, $OR_{26}$ or $SR_{27}$ group;

$L_X=L_{X'}$ and $L_x$ represents a bond; and $R_2=R_3$ and $R_2$ represents a hydrogen atom.

In particular, said compound is chosen among compounds 1 to 32, preferably among compounds 1 to 3, 8, 11 and 27 to 32.

In a particular embodiment, said compound is a compound of formula (I) wherein:

$R_0$ represents a hydrogen atom, a halogen atom, a $(C_1-C_6)$alkyl, $(C_1-C_6)$haloalkyl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_5$, $SR_6$, $NR_7R_8$, $PR_9R_{10}$, $COR_{11}$, $CO_2R_{12}$, $CONR_{13}R_{14}$, $SO_2R_{15}$, $SO_3H$, CN, $NO_2$, $OCOR_{16}$, $OCO_2R_{17}$, $NR_{18}COR_{19}$ or $NR_{20}SO_2R_{21}$ group, or is selected from the group consisting of:

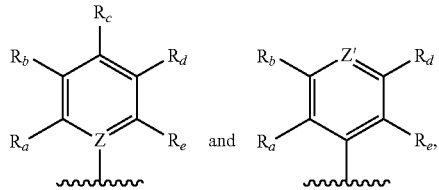

wherein:

Z represents C or $N^+ A_z^-$ and Z' represents N or $N^+-R_c' A_z^-$, wherein $A_z^-$ represents a monovalent organic or inorganic anion, and $R_c'$ represents a hydrogen atom or a $(C_1-C_6)$alkyl group, $R_a$ and $R_e$ each represent, independently of each other, a halogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_{22}$ or $SR_{23}$ group, and $R_b$, $R_c$ and $R_d$ each represent, independently of each other, a hydrogen atom, a halogen atom or a $(C_1-C_6)$alkyl, $(C_1-C_6)$haloalkyl, cycloalkyl, cycloalkyl-$(C_1-C_6)$alkyl, heterocycle or heterocycle-$(C_1-C_6)$alkyl group;

$R_1=R_1'$, and $R_1$ represents a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_mOR_{24}$, $(CH_2)_mSR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;

$R_4=R_4'$, and $R_4$ represents a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_mOR_{24}$, $(CH_2)_mSR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;

with the proviso that when $R_1$ and $R_4$ are the same, at least one of $R_a$ and $R_e$ is not the same as $R_1$;

or $R_4$ and $R_4'$ form together a bond or a chain selected from the group consisting of —$C(R_{74}R_{75})$—, —$(CH_2)_n$—, —$Si(R_{76}R_{77})$—, —$(CH_2)_p$—Y—$(CH_2)_q$—, and —Y—$(CR_{78}R_{79})_r$—Y'—, wherein:

Y and Y' each represent, independently of each other, O, S or $NR_{80}$, n is equal to 2 or 3, p is equal to 1 or 2, q is equal to 0 or 1, r is equal to 1 or 2, $R_{74}$, $R_{75}$, $R_{78}$ to $R_{80}$ each represent, independently of each other, a hydrogen atom, a $(C_1-C_6)$alkyl or an aryl group, and $R_{76}$ and $R_{77}$ each represent, independently of each other, a $(C_1-C_6)$alkyl or an aryl group;

$R_2=R_2'$, $R_3=R_3'$, and $R_2$ and $R_3$ each represent, independently of each other, a hydrogen atom, a halogen atom, a $(C_1-C_6)$alkyl, $(C_2-C_6)$alkenyl, $(C_2-C_6)$alkynyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_{42}$, $SR_{43}$, $NR_{44}R_{45}$, $COR_{46}$, $CO_2R_{47}$ or $CONR_{48}R_{49}$ group, preferably a hydrogen atom;

$L_X=L_{X'}$ and $L_X$ represents a bond, or a group selected from the group consisting of:

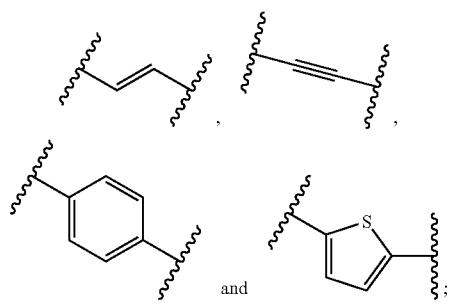

$X=X'$, and X represents $NR_{50}R_{51}$, heterocycle, heteroaryl or aryl, wherein:

said heterocycle and heteroaryl group comprise at least one nitrogen atom bearing a lone pair of electrons conjugated with $C^+$, and are optionally substituted by one or more groups selected from a halogen atom, a $(C_1-C_6)$alkyl, $(C_1-C_6)$haloalkyl, $OR_{56}$, $SR_{57}$ and $NR_{58}R_{59}$ group, and said aryl is para-substituted by a $NR_{60}R_{61}$ group, and optionally substituted by one or more groups selected from a halogen atom, a $(C_1-C_6)$alkyl, $(C_1-C_6)$haloalkyl, $OR_{66}$, $SR_{67}$ and $NR_{68}R_{69}$ group;

or $R_1$ and $R_2$, and $R_1'$ and $R_2'$ form together with the carbon atoms that carry them a cycle selected from the group consisting of cycloalkenyl, heterocycle, aryl and heteroaryl, said cycle being optionally substituted by one or more groups selected from a halogen atom, $(C_1-C_6)$alkyl, $(C_1-C_6)$haloalkyl, $OR_{70}$, $SR_{71}$ and $NR_{72}R_{73}$;

and/or $R_3$ and $R_4$, and $R_3'$ and $R_4'$ form together with the carbon atoms that carry them a cycle selected from the group consisting of cycloalkenyl, heterocycle, aryl and heteroaryl, said cycle being optionally substituted by one or more groups selected from a halogen atom, $(C_1-C_6)$alkyl, $(C_1-C_6)$haloalkyl, $OR_{70}$, $SR_{71}$ and $NR_{72}R_{73}$;

and/or $L_X=L_{X'}$ and $L_X$ represents a bond; $X=X'$ and X represents $NR_{50}'R_{51}'$, $PR_{52}'R_{53}'$, $OR_{54}'$ or $SR_{55}'$; and $R_2$ and $NR_{50}'$, and $R_2'$ and $NR_{50}'$; $R_2$ and $PR_{52}'$, and $R_2'$ and $PR_{52}'$; $R_2$ and $OR_{54}'$, and $R_2'$ and $OR_{54}'$; or $R_2$ and $SR_{55}'$, and $R_2'$ and $SR_{55}'$ form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$;

and/or $R_3$ and $NR_{51}'$, and $R_3'$ and $NR_{51}'$; $R_3$ and $PR_{53}'$, and $R_3'$ and $PR_{53}'$; $R_3$ and $OR_{54}'$, and $R_3'$ and $OR_{54}'$; or $R_3$ and $SR_{55}'$, and $R_3'$ and $SR_{55}'$ form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$;

and $R_{50}'$, $R_{51}'$, $R_{52}'$ and $R_{53}'$ represent respectively $R_{50}$, $R_{51}$, $R_{52}$ and $R_{53}$ when they are not linked with $R_2$ or $R_3$;

and $R_5$ to $R_{53}$, $R_{56}$ to $R_{63}$, $R_{66}$ to $R_{73}$ and $R_{81}$ to $R_{84}$ each represent, independently of each other, a hydrogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1-C_6)$alkyl group;

and $R_{54}$, $R_{55}$, $R_{64}$ and $R_{65}$ each represent, independently of each other, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1-C_6)$alkyl group;

and

A⁻ represents a monovalent or multivalent, organic or inorganic anion.

In a particular embodiment, A⁻ represents a hexafluorophosphate, tetrafluoroborate, tetraphenylborate, DDQH⁻, halide or triflate anion, preferably a DDQH⁻ or a hexafluorophosphate anion, notably a hexafluorophosphate anion.

More particularly, as exemplified in the experimental section, because of their special optical effect(s), said compounds are useful as a luster pigment; even more specifically as a metal effect pigment and/or a pearl luster pigment.

The invention also relates to a reflective, photonic, nanophotonic or optoelectronic device, that comprises at least one compound according to the invention.

In the context of the present invention, a reflective device can notably be a mirror.

The range of application media for the pigments with special optical effects (and in some cases for their constitutive chromophores) according to the invention includes notably paints, coatings, printing inks, cosmetic formulations (e.g. nail lacquers) as well as implementations in the recreational and artistic (e.g. enamel) fields.

Another possible application is the design of pigments for conception of new security inks that enter for example in the fabrication of banknotes, official identity documents, postage stamps, tax banderoles, security labels or product markings.

Another possible application is the design of pigments and/or materials for the conception of new optical reflectors that enter for example in the fabrication of small mirrors for optics/microscopy/interferometry, sensors, very small mirrors for lasers (optical cavity) or mirrors for nomad and embarked devices.

Another possible application is the design of pigments, materials and/or inks for the conception of VCSEL (vertical-cavity surface-emitting laser) or optical waveguides to be included in printed and/or integrated photonic circuits and/or devices, or excitonic nanostructures.

As regards molecular chromophores possible applications span from bioimaging purposes, notably to stain fibrillar structures like those associated with a variety of neurodegenerative diseases, among which Alzheimer's disease, to the conception of new high performance optical limiter devices relying on non-linear optical properties displayed by compounds objects of the invention.

In some embodiments, metal-like reflective coatings can be easily achieved by simple doctor-blade coating, spin-coating or vacuum deposition of pure compound dissolved or suspended in a suitable deposition medium.

Reflectance spectra can be recorded with dedicated equipment in order to evaluate quantitatively the efficiency of the thin film to reflect light as a function of wavelength and incidence angle.

The invention thus also relates to metal-like reflective coating that comprises at least one compound according to the invention.

The range of application media for mirror according to the invention includes notably reflective surfaces for the photonic industry, used for example inside equipment for telecommunication applications such as transceivers for data centers. The invention may be also used for larger mirrors used for example in solar electricity production.

FIGURES

FIG. 1 represents the absorption spectra of compounds 1-$PF_6^-$ and 2-$PF_6^-$ in solution in acetonitrile.

Figure 2:

FIG. 2 corresponds to a picture of a $10^{-5}$ mol·L⁻¹ solution of compound 1-$PF_6^-$ in acetonitrile, characterized by its intense deep blue color.

Figure 3:

FIG. 3 corresponds to a picture of a gold-like mirror of compound 1-$PF_6^-$ that forms on the wall of a round-bottom flask, resulting from the evaporation under reduced pressure of a concentrated acetonitrile solution of chromophoric compound 1-$PF_6^-$.

Figure 4A:
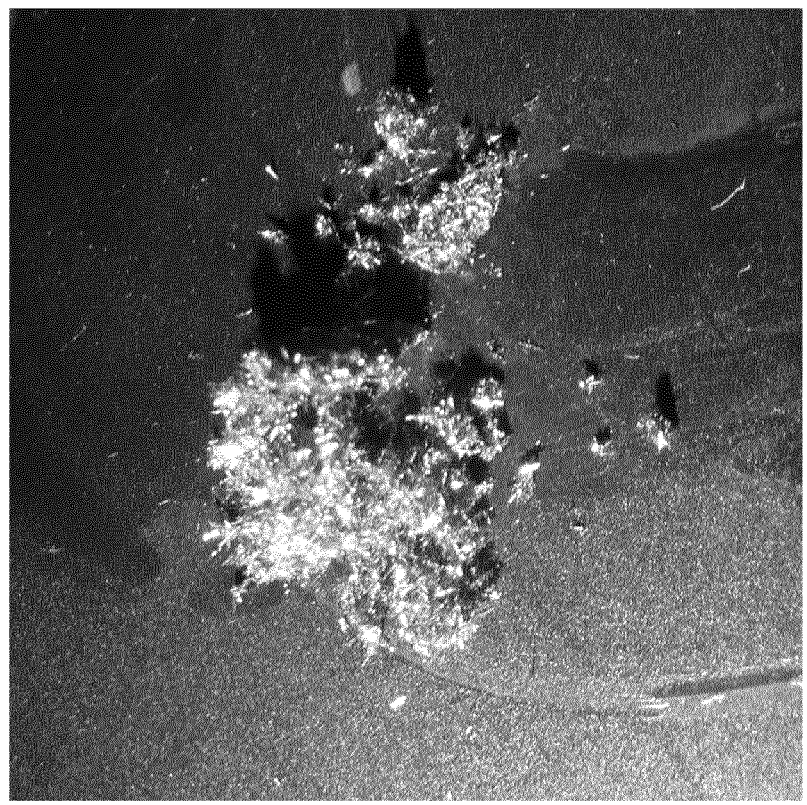

FIG. 4a represents a macroscopic view of compound 1-$PF_6^-$ in its microcrystallized form, characterized by its metallic and gold flakes appearance.

Figure 4B:
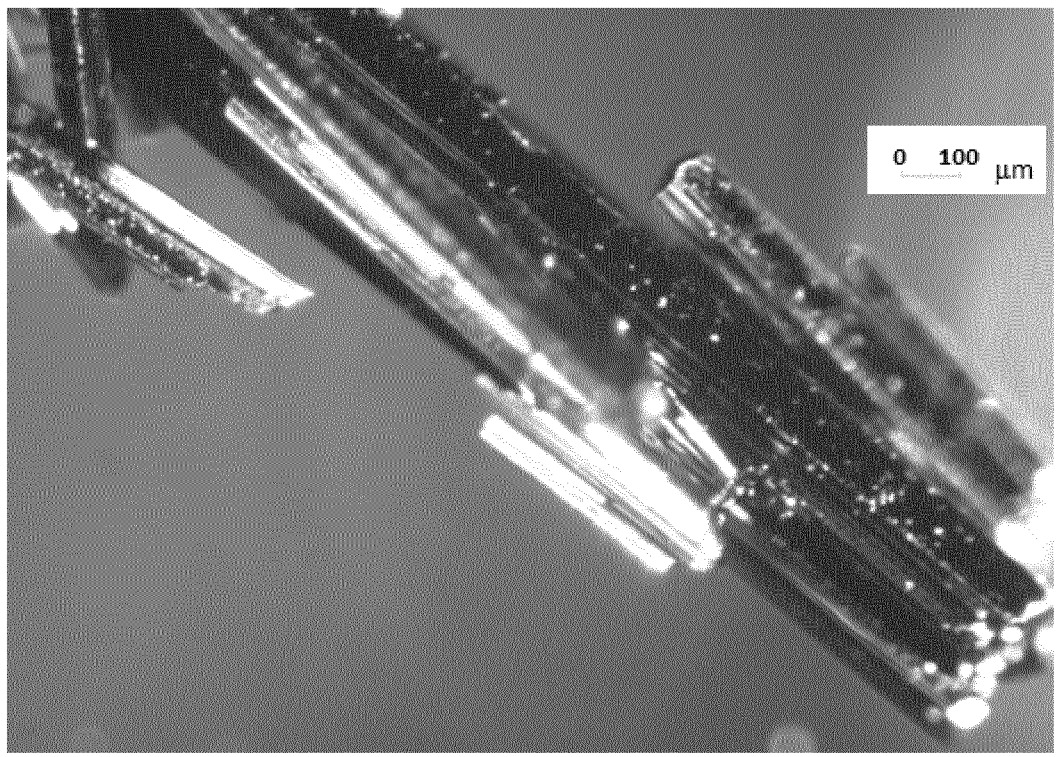
Figure 4C:
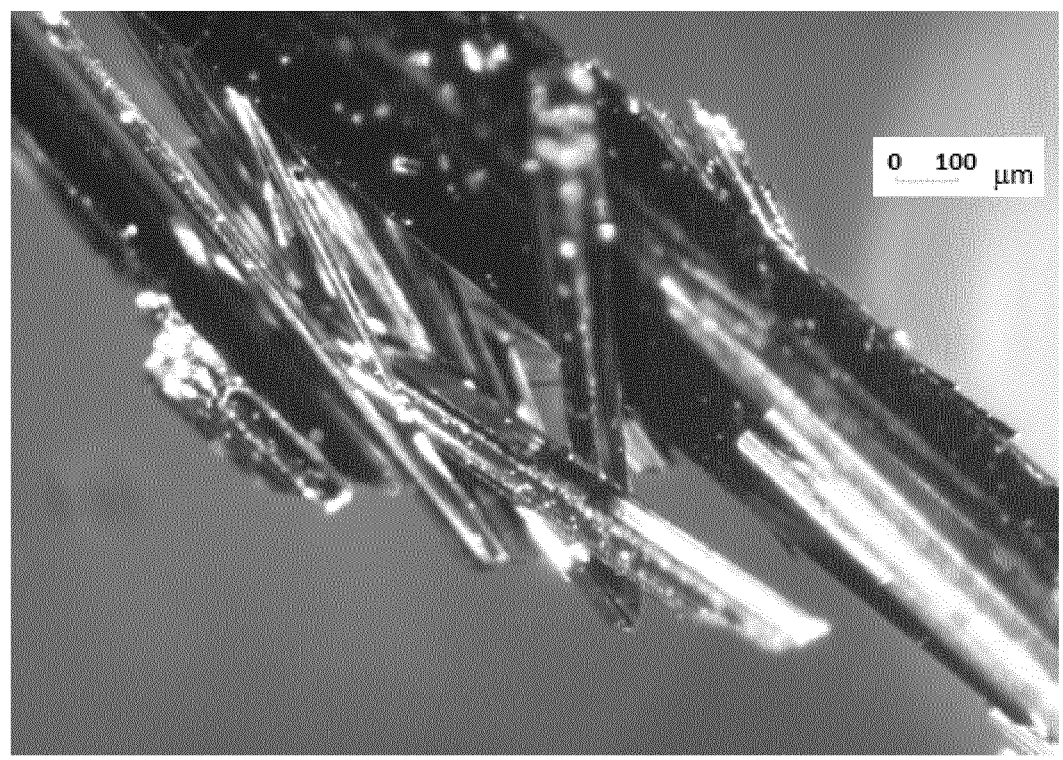

FIGS. 4b and 4c both display microscopic views of compound 1-$PF_6^-$ in the form of large single crystals, obtained with a Zeiss-Stemi 2000-C microscope.

Figure 5:
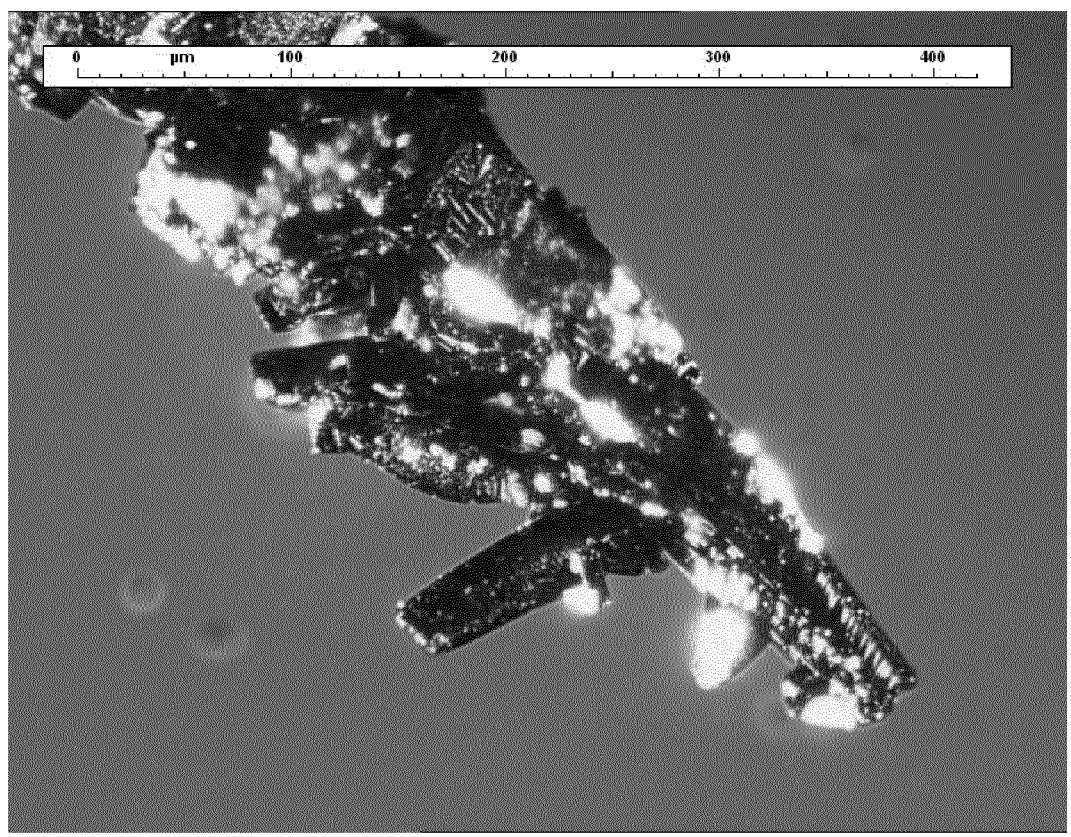

FIG. 5 displays a microscopic view of iridescent compound 2-$PF_6^-$ in a polycrystalline form, obtained with a Zeiss-Stemi 2000-C microscope.

Figure 6:
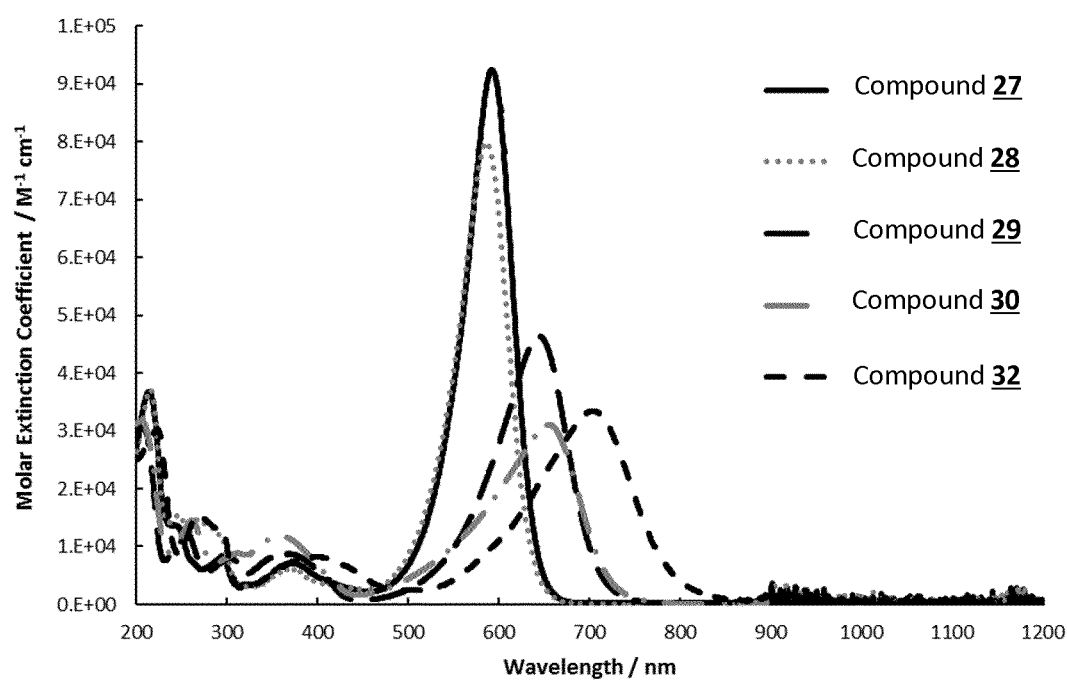

FIG. 6 represents the absorption spectra of compounds 27-$PF_6^-$, 28-$PF_6^-$, 29-$PF_6^-$, 30-$PF_6^-$, 32-$PF_6^-$ in solution in acetonitrile.

Figure 7A:
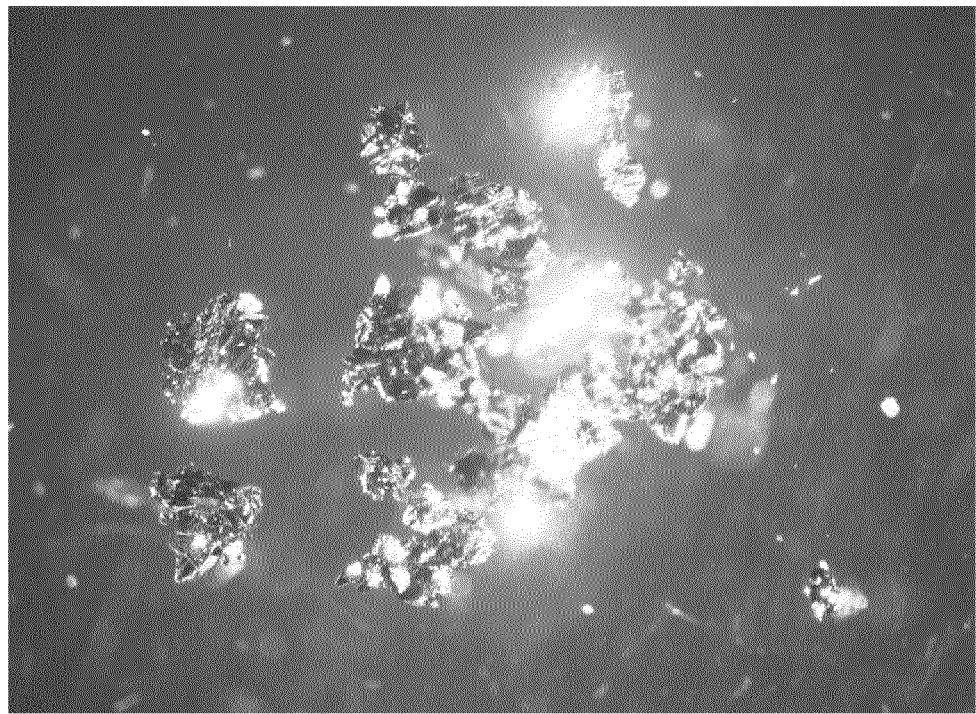
Figure 7B:
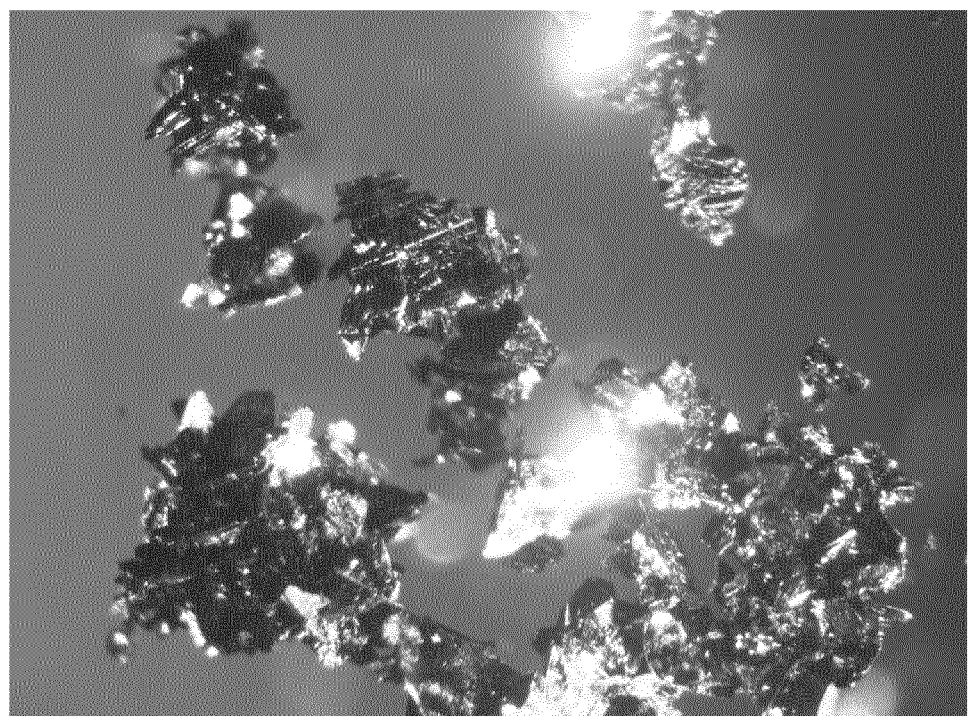

FIGS. 7a and 7b both display microscopic views of compound 27-DDQH⁻ in a polycrystalline form, obtained with a Zeiss-Stemi 2000-C microscope.

Figure 8A:
Figure 8B:

FIGS. 8a and 8b both display microscopic views of compound 27-$PF_6^-$ in a polycrystalline form, obtained with a Zeiss-Stemi 2000-C microscope.

Figure 9A:
Figure 9B:
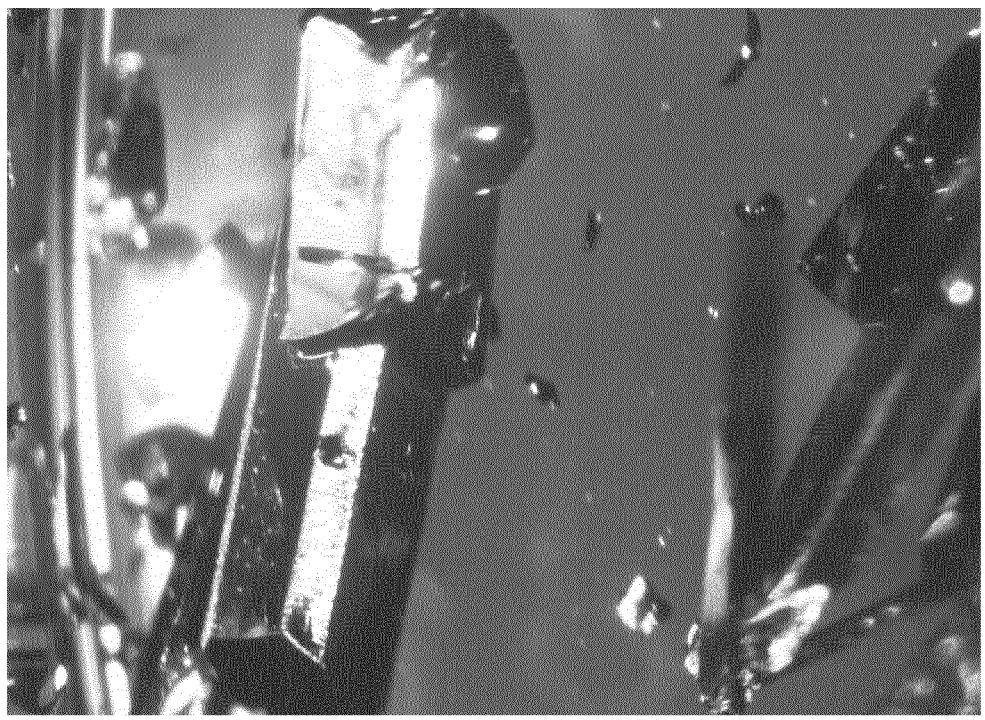

FIGS. 9a and 9b both display microscopic views of compound 28-$PF_6^-$ in the form of large single (columnar) crystals, obtained with a Zeiss-Stemi 2000-C microscope.

Figure 10A:
Figure 10B:
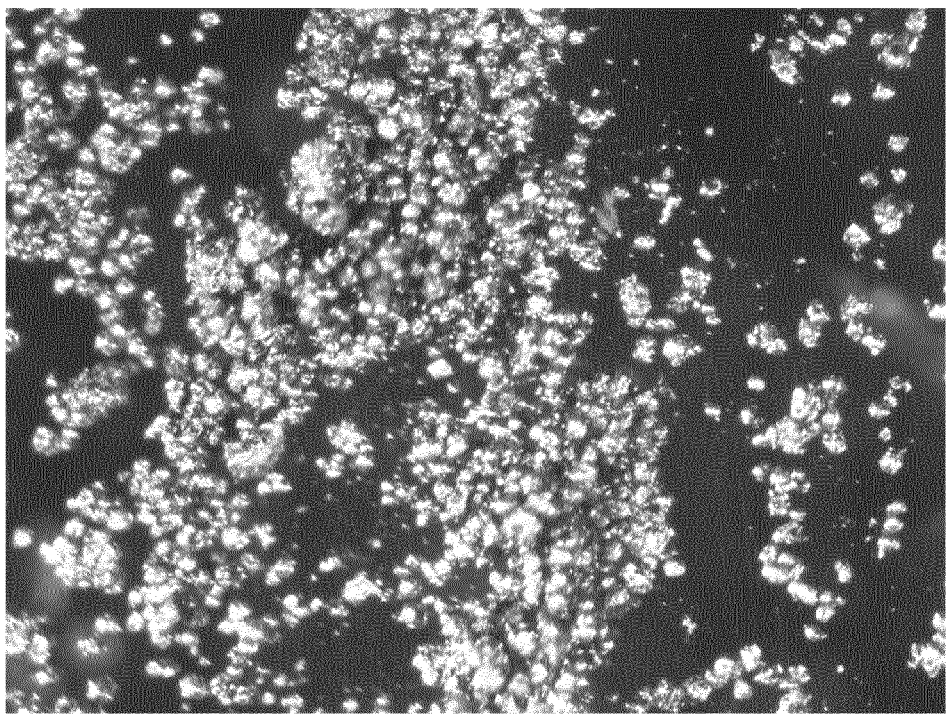

FIGS. 10a and 10b both display microscopic views of compound 29-DDQH⁻ in its microcrystallized form, characterized by its metallic and gold flakes appearance, obtained with a Zeiss-Stemi 2000-C microscope.

Figure 11A:
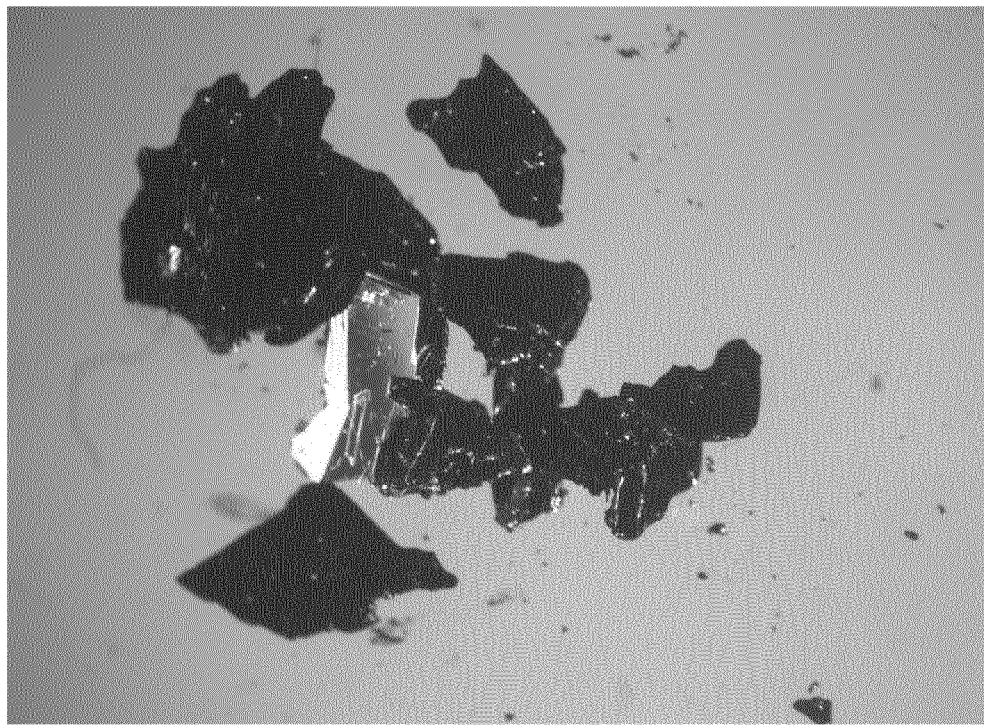
Figure 11B:
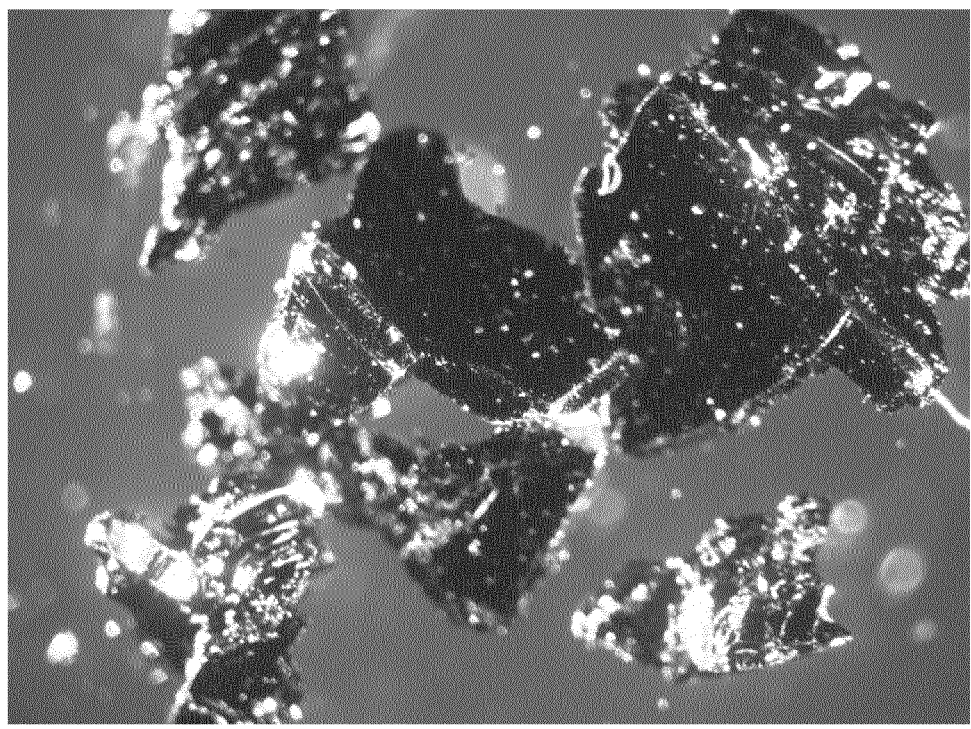

FIGS. 11a and 11b both display microscopic views of compound 29-$PF_6^-$ in the form of large single crystals, obtained with a Zeiss-Stemi 2000-C microscope.

Figure 12A:
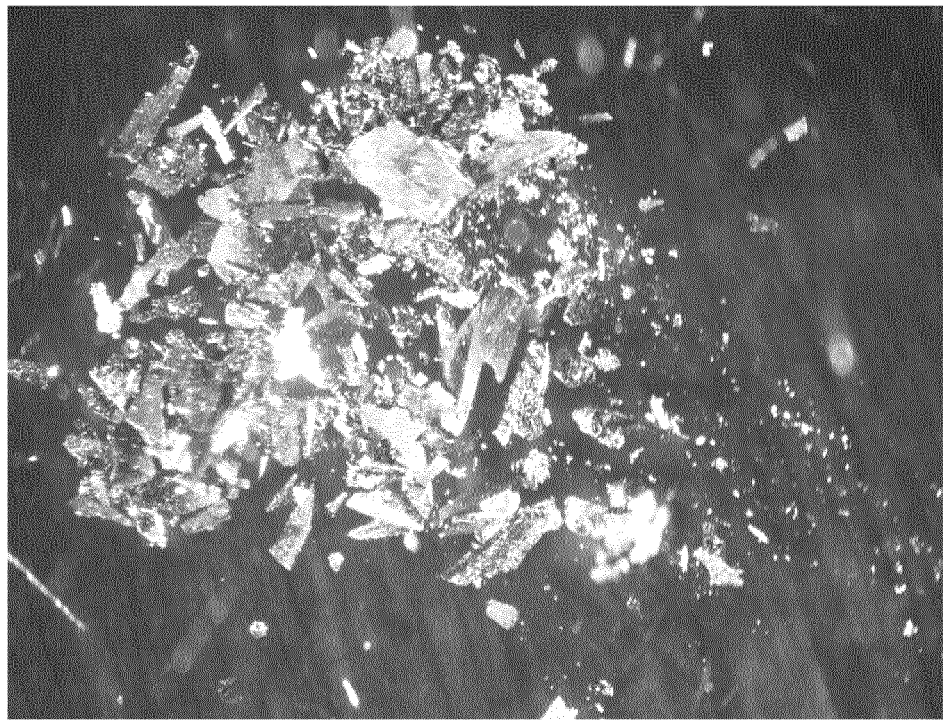
Figure 12B:
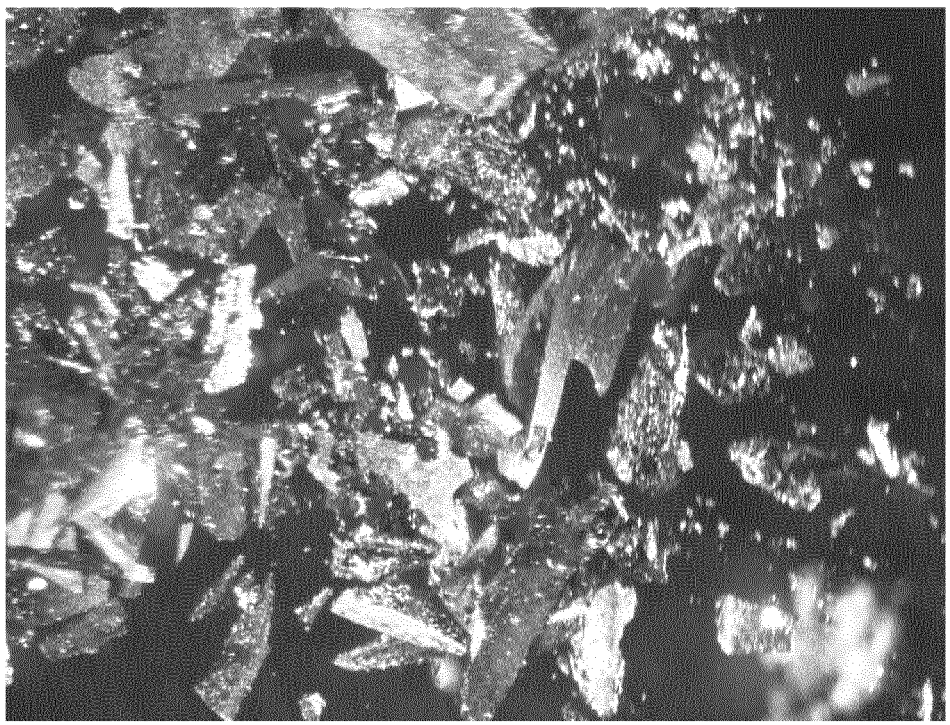

FIGS. 12a and 12b both display microscopic views of compound 30-$PF_6^-$ in a polycrystalline form, obtained with a Zeiss-Stemi 2000-C microscope.

Figure 13A:
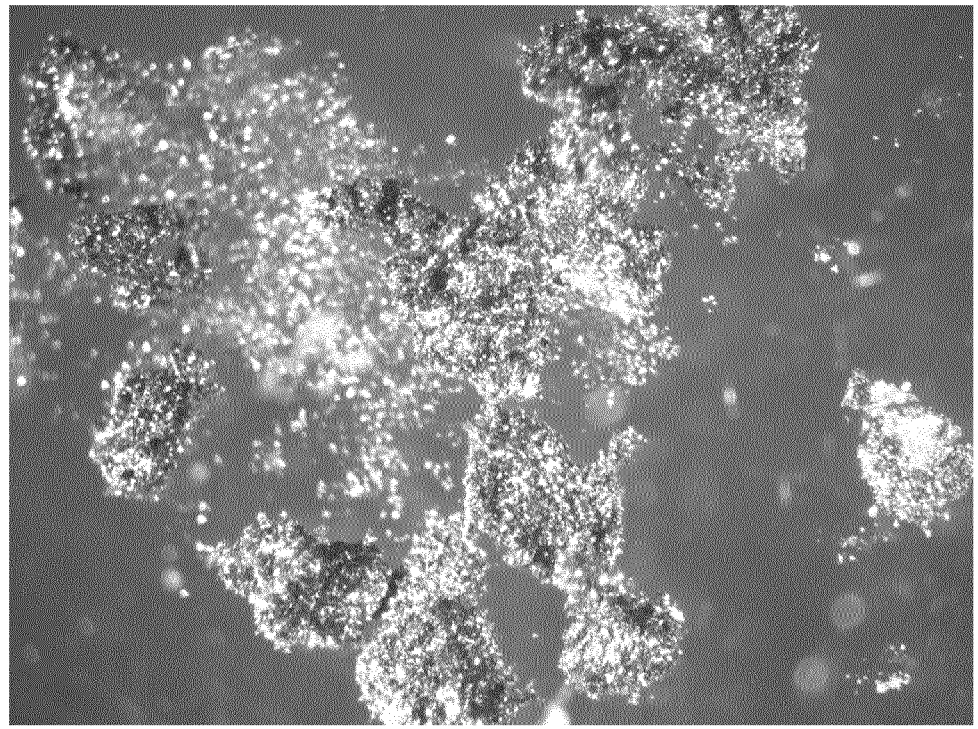
Figure 13B:
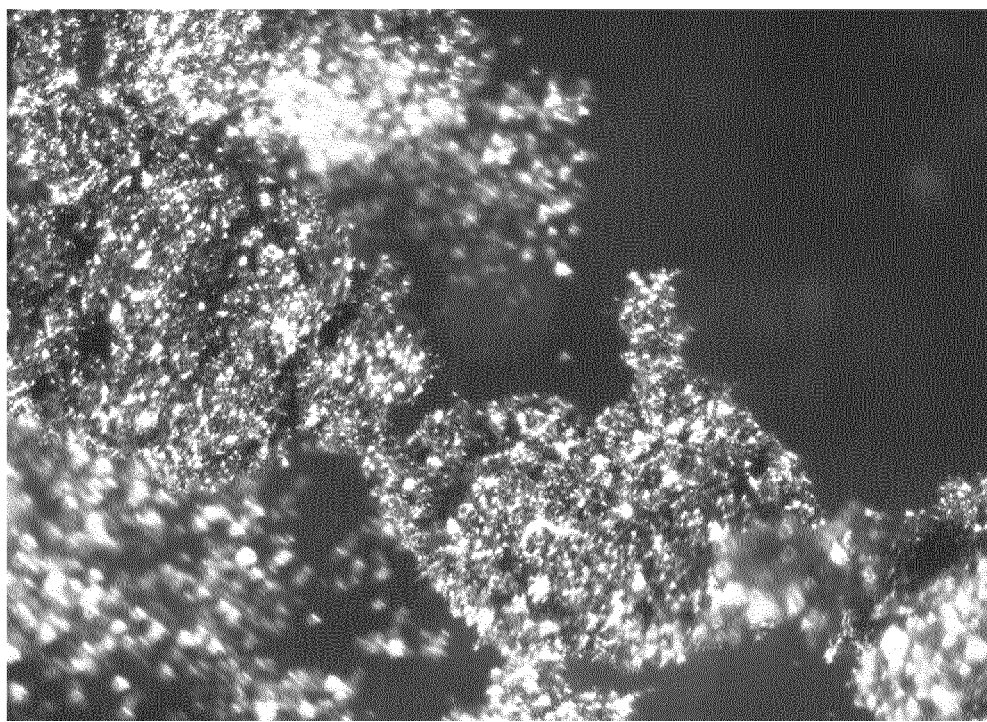

FIGS. 13a and 13b both display microscopic views of compound 32-DDQH⁻ in its microcrystallized form, characterized by its metallic and gold flakes appearance, obtained with a Zeiss-Stemi 2000-C microscope.

Figure 14A:
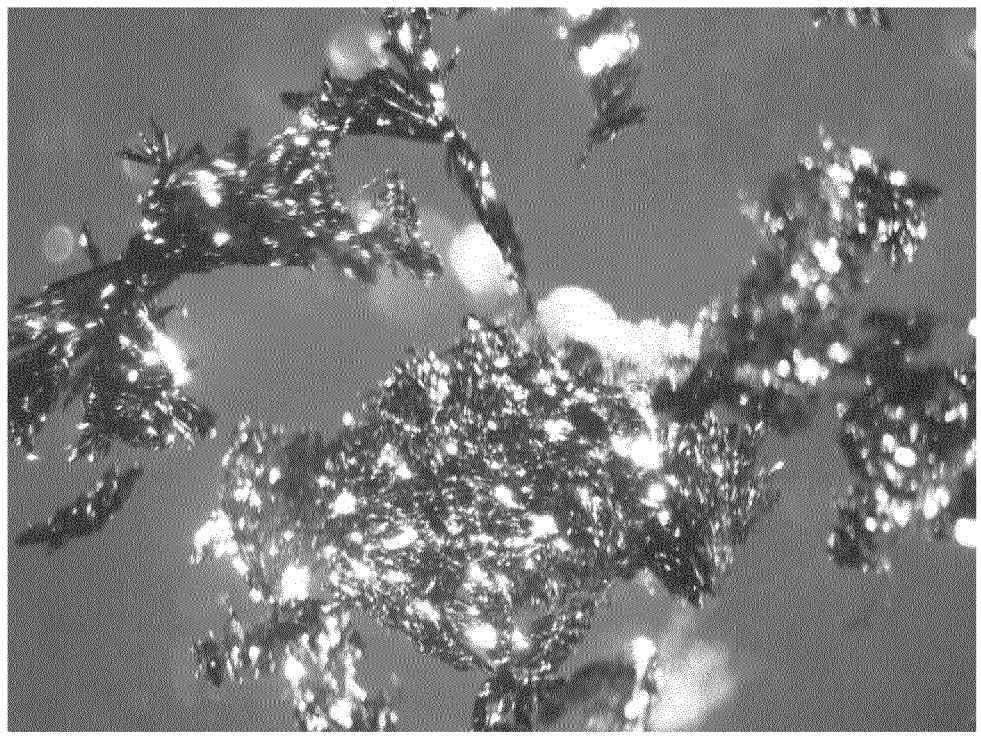
Figure 14B:
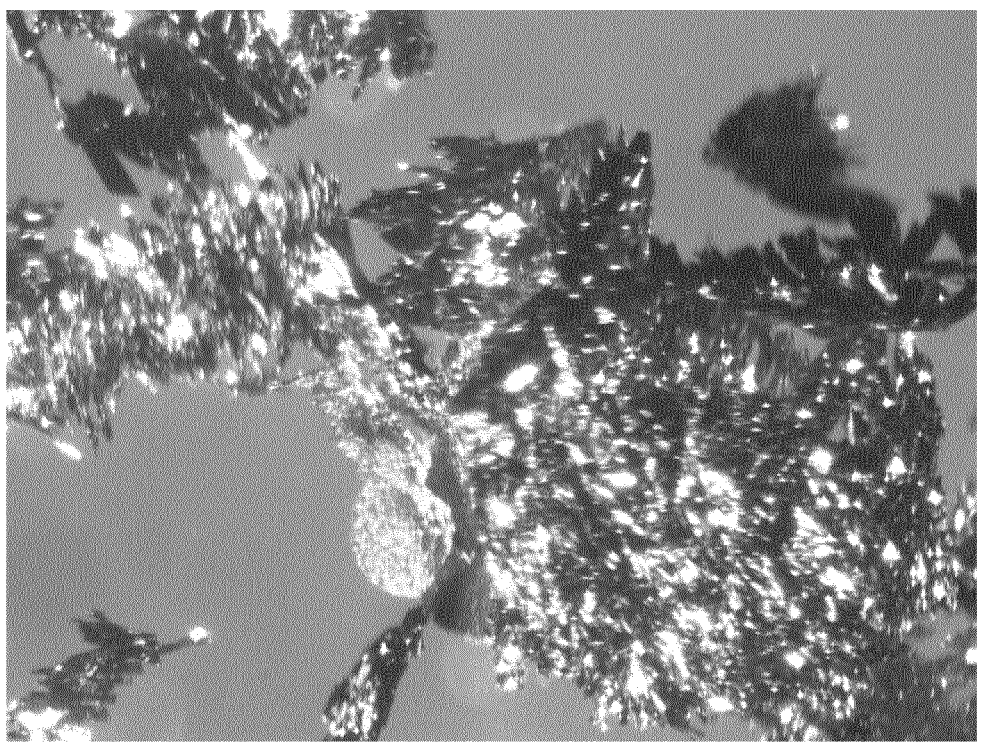

FIGS. 14a and 14b both display microscopic views of compound 32-PF$_6^-$ in a polycrystalline form, obtained with a Zeiss-Stemi 2000-C microscope.

The examples that follow illustrate the invention without limiting its scope in any way.

EXAMPLES

The following abbreviations have been used:
Ac: Acetyl (COCH$_3$)
Bn: Benzyl (CH$_2$Ph)
Bu: Butyl (CH$_2$CH$_2$CH$_2$CH$_3$)
ca.: circa
DDQ: 2,3-Dichloro-5,6-dicyano-1,4-benzoquinone
DMF: Dimethylformamide
EDG: Electron-Donating Group
equiv.: equivalent
ESI: Electrospray ionisation
Et: Ethyl (CH$_2$CH$_3$)
Me: Methyl (CH$_3$)
MS: Mass Spectroscopy
NBS: N-Bromosuccinimide
NIR: Near Infra Red
NMR: Nuclear Magnetic Resonance
Ph: Phenyl (C$_6$H$_5$)
THF: Tetrahydrofuran
TMEDA: Tetramethylethylenediamine
TMSI: Trimethylsilyl iodide
vis: visible
wt: weight I—Synthesis of the Compounds According to the Invention I-1. General Procedures General Procedure A Compounds of the formula A (para-electrodonating ortho-substituted diphenylcarbenium) can be prepared by the following Reaction Scheme 1, wherein X is an EDG:

A meta-disubstituted electrodonating precursor (either commercially available or not) is engaged in a lithiation reaction. Depending on the nature of the starting material, a prior step of para bromination may be necessary, employing either Br$_2$ or NBS as reactive species [Zysman2009]. The lithiated intermediate is quenched with ethyl formate yielding a carbinol intermediate [Patents], itself easily dehydrated to produce the desired carbenium when reacted with acidic species (HA), the nature of which determines the identity of carbenium counteranion (A$^-$). The latter can be changed afterward by anion metathesis.

General Procedure Abis

Compounds of the formula A (para-electrodonating ortho-substituted diphenylcarbenium) can also be prepared by the following Reaction Scheme 2 as a one pot reaction (Scheme 2 a)) or as a two-step reaction (Scheme 2b)), wherein X is an EDG:

Reaction Scheme 2

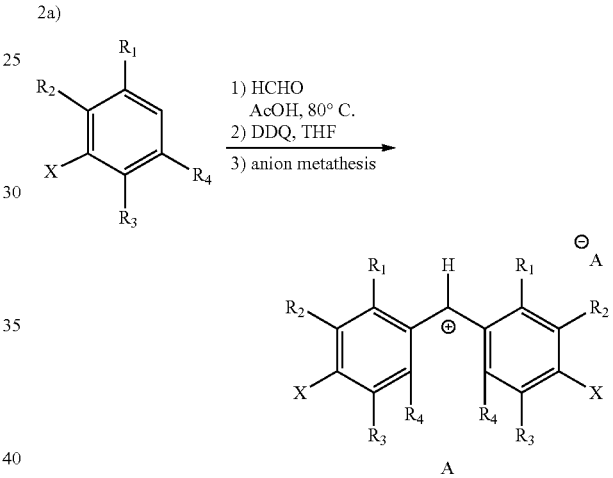

Reaction Scheme 1

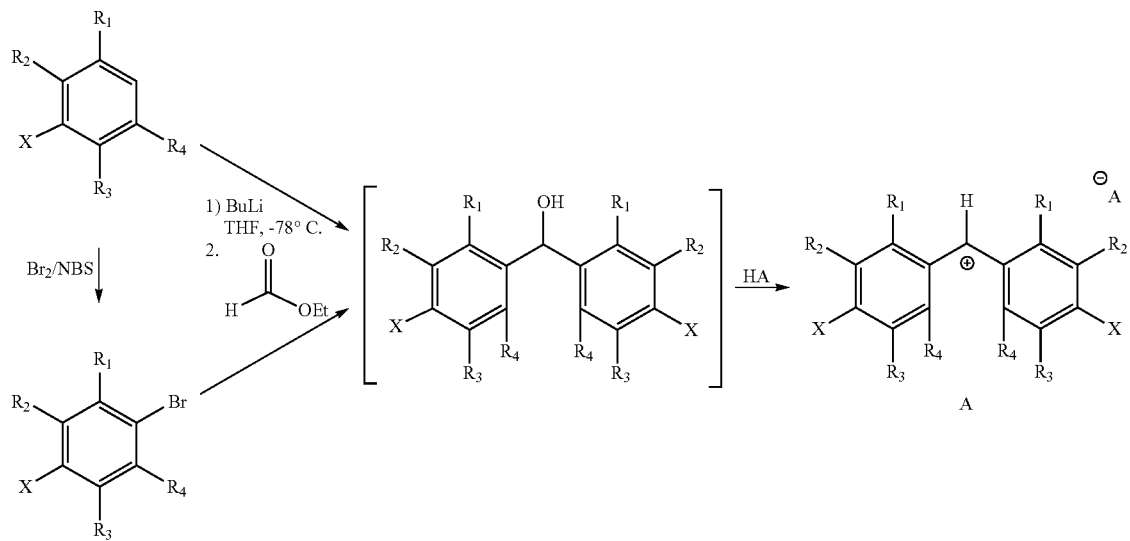

2b)

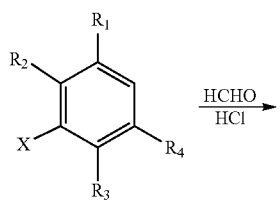

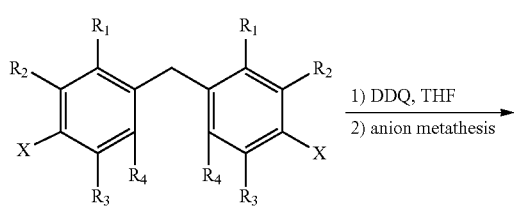

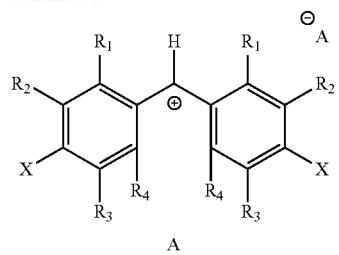

A meta-disubstituted electrodonating precursor (either commercially available or not) is engaged in a formaldehyde-mediated dimerization reaction [Takahashi2002]. The resulting methylene, that often easily crystallizes is then oxidized with DDQ (or another suitable oxidant, which is here more particularly a hydride abstraction reagent) to directly produce the desired carbenium. A final step of metathesis may optionally be required to obtain the desired counteranion ($A^-$).

General Procedure B

Compounds of the formula B (para-diamino ortho-substituted diphenylcarbenium) can be prepared by the following Reaction Scheme 3:

Reaction Scheme 3

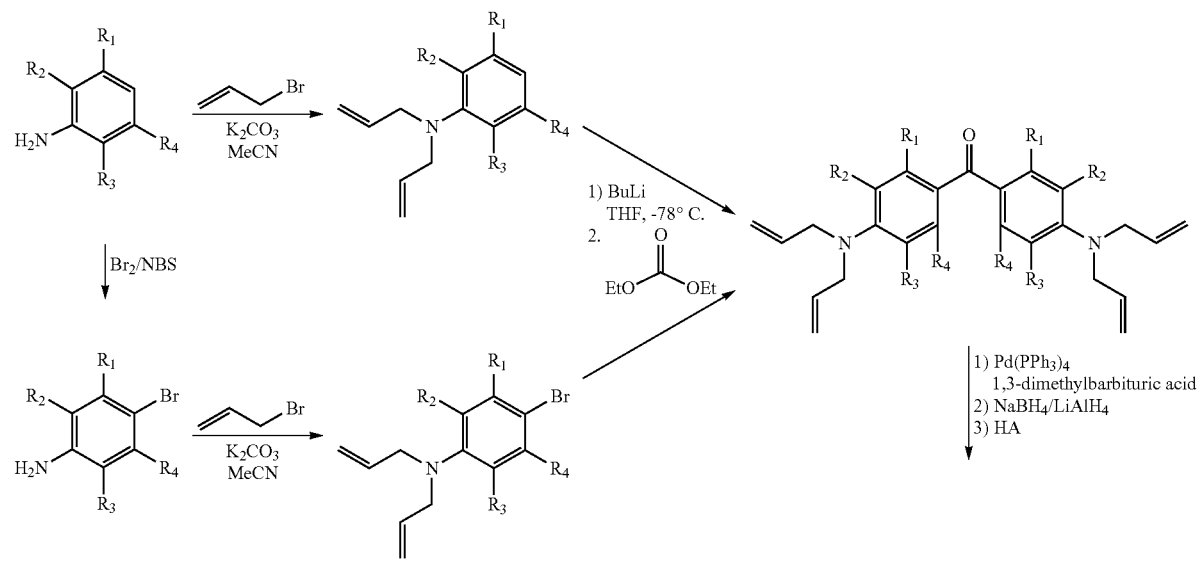

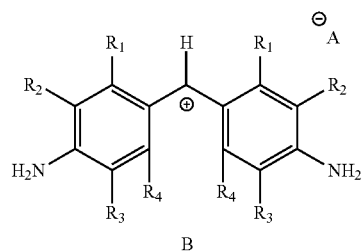

A meta-disubstituted diallylamino precursor (itself synthesized from its corresponding parent aniline, either commercially available or not, according to a classical procedure [Egawa2011]) is engaged in a lithiation reaction. Depending on the nature of the starting material, a step of para bromination prior nitrogen allylation may be necessary, employing either $Br_2$ or NBS as reactive species [Zysman2009]. The lithiated intermediate is quenched with diethyl carbonate yielding a congested bis(diallylamino) benzophenone precursor, which amine groups can be deprotected in presence of palladium tetrakis and 1,3-dimethylbarbituric acid [Egawa2011]. The ketone function can then be reduced (by either $NaBH_4$ or $LiAlH_4$) yielding the corresponding carbinol intermediate that can be itself easily dehydrated to produce the desired carbenium when reacted with acidic species (HA), the nature of which determines the identity of carbenium counteranion ($A^-$). The latter can be changed afterward by anion metathesis.

General Procedure C

Compounds of the formula C (julolidine-type ortho-substituted diphenylcarbenium) can be prepared by the following Reaction Scheme 4:

Reaction Scheme 4

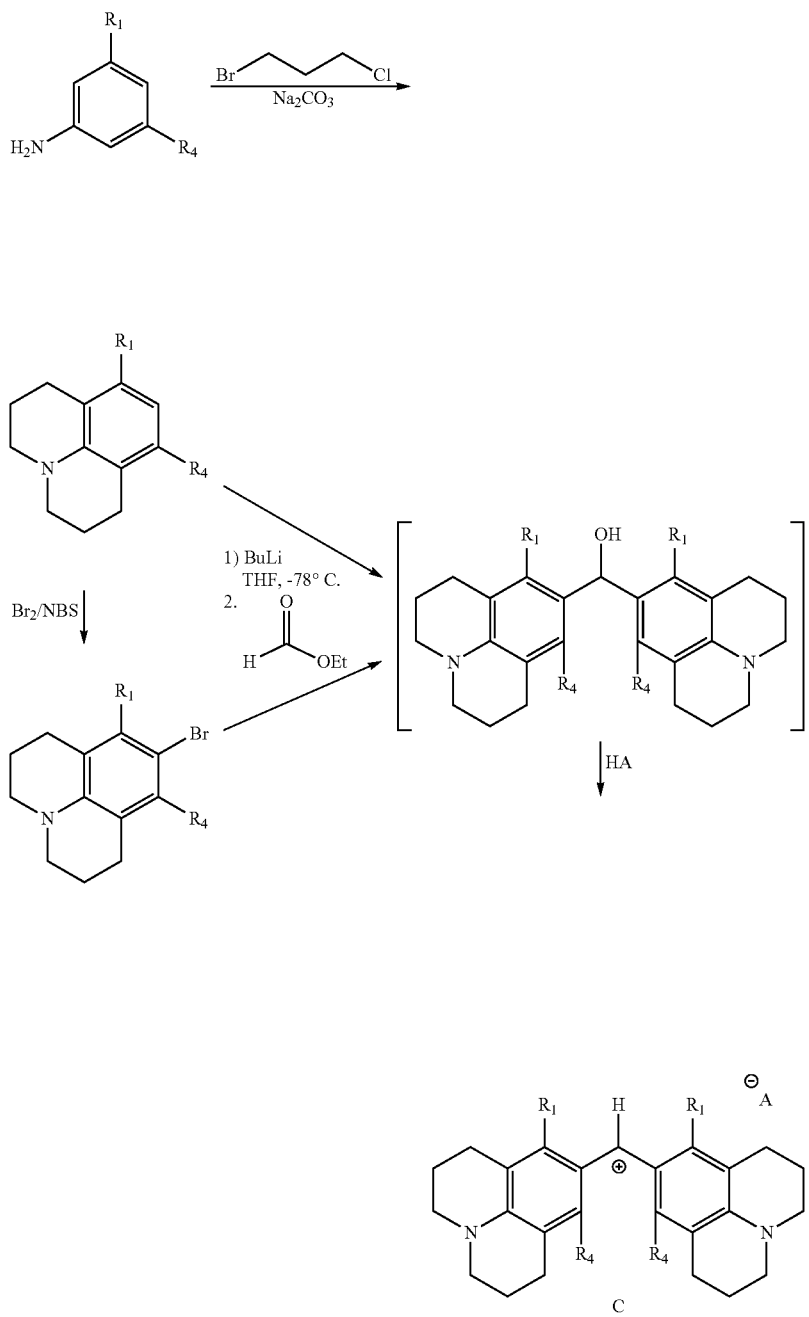

A disubstituted julolidine-type precursor (itself synthesized from its corresponding parent aniline, either commercially available or not, according to a classical procedure [Dance2008]) is engaged in a lithiation reaction. Depending on the nature of the starting material, a prior step of para bromination may be necessary, employing either Br₂ or NBS as reactive species [Zysman2009]. The lithiated intermediate is quenched with ethyl formate yielding a carbinol intermediate [Patents], itself easily dehydrated to produce the desired carbenium when reacted with acidic species (HA), the nature of which determines the identity of carbenium counteranion (A⁻). The latter can be changed afterward by anion metathesis.

General Procedure Cbis

Compounds of the formula C (julolidine-type ortho-substituted diphenylcarbenium) can also be prepared by the following Reaction Scheme 5 as a one pot reaction (Scheme 5 a)) or as a two-step reaction (Scheme 5 b)):

Reaction Scheme 5

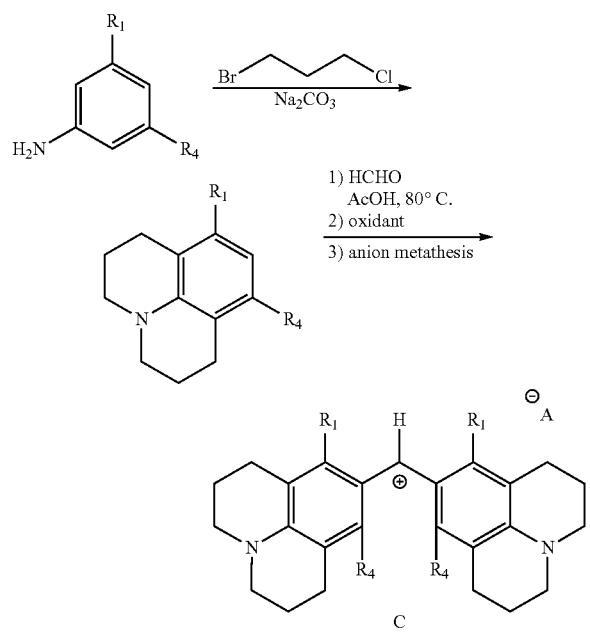

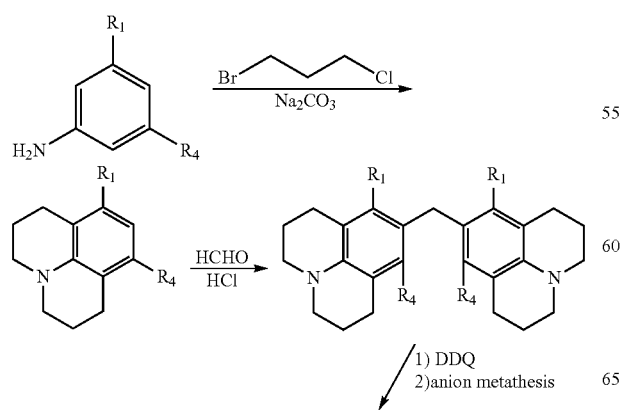

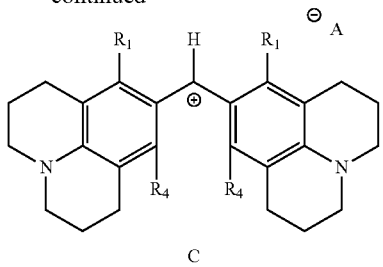

A disubstituted julolidine-type precursor (itself synthesized from its corresponding parent aniline, either commercially available or not, according to a classical procedure [Dance2008]) is engaged in a formaldehyde-mediated dimerization reaction [Takahashi2002]. The resulting methylene, that often easily crystallizes is then oxidized with DDQ (or another suitable oxidant, which is here more particularly a hydride abstraction reagent) to directly produce the desired carbenium. A final step of metathesis may optionally be required to obtain the desired counteranion (A⁻).

General Procedure D

Compounds of the formula D can be obtained from the key benzophenone (KB) precursor prepared by the following Reaction Scheme 6:

Reaction Scheme 6

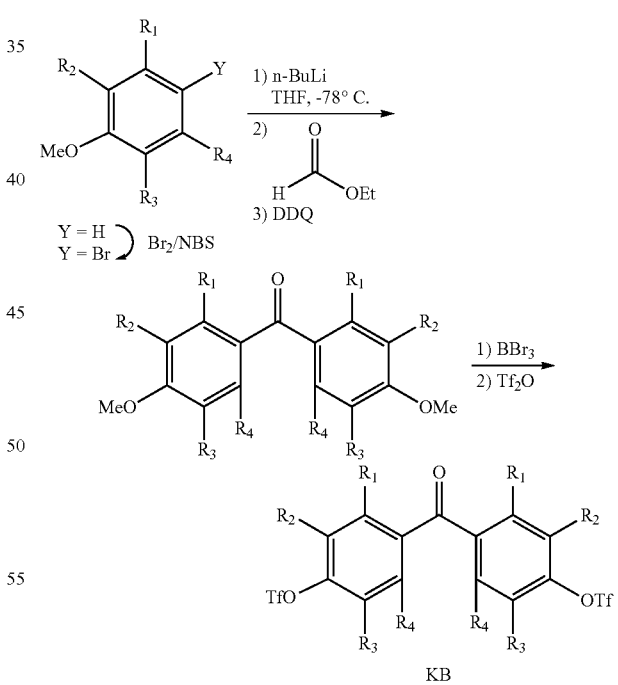

A meta-disubstituted anisole (either commercially available or not) is para-brominated according to a classical procedure employing either Br₂ or NBS as reactive species [Zysman2009]. The resulting bromoanisole is then engaged in a lithiation reaction, and the intermediate is quenched with ethyl formate yielding a carbinol intermediate [Patents] which is subsequently oxidized to the corresponding ketone by using DDQ [Torricelli2013]. The methoxy groups of this benzophenone are demethylated by using $BBr_3$ and the resulting phenol moieties are then reacted with triflic anhydride to give the desired key benzophenone derivative, KB.

Compounds of the formula D (aryl extended ortho-substituted diphenylcarbenium) can then be prepared by the following Reaction Scheme 7, wherein X is an EDG:

Reaction Scheme 7

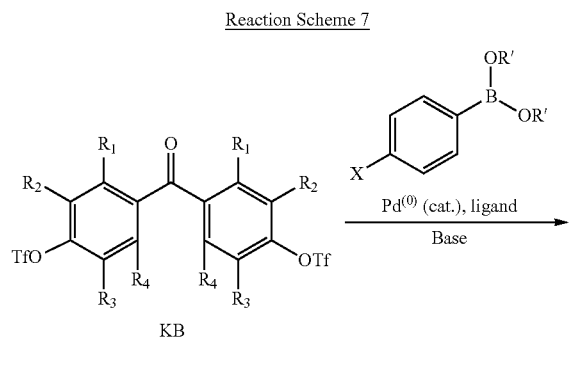

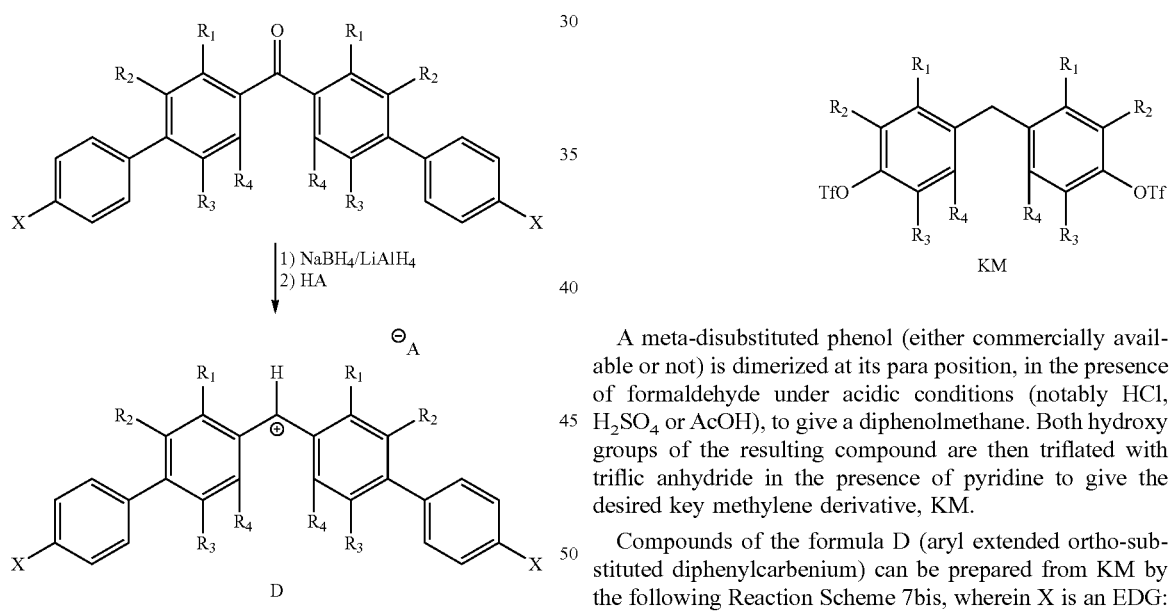

The previously described key benzophenone KB may be engaged in a double Suzuki cross-coupling by reacting with a suitable electron-rich boronic acid/ester (either commercially available or not) in presence of a base and a palladium catalyst. The resulting extended benzophenone can then be reduced (by either $NaBH_4$ or $LiAlH_4$) yielding the corresponding carbinol intermediate that can be itself easily dehydrated to produce the desired carbenium when reacted with acidic species (HA), the nature of which determines the identity of carbenium counteranion ($A^−$). The latter can be changed afterward by anion metathesis.

General Procedure Dbis

Compounds of the formula D can also be obtained from the key methylene (KM) precursor prepared by the following Reaction Scheme 6bis:

Reaction Scheme 6bis

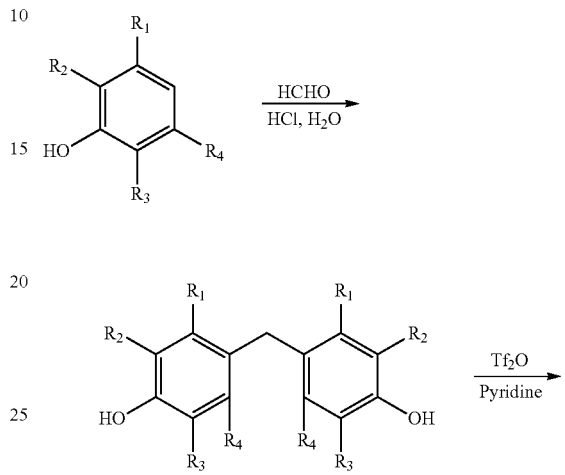

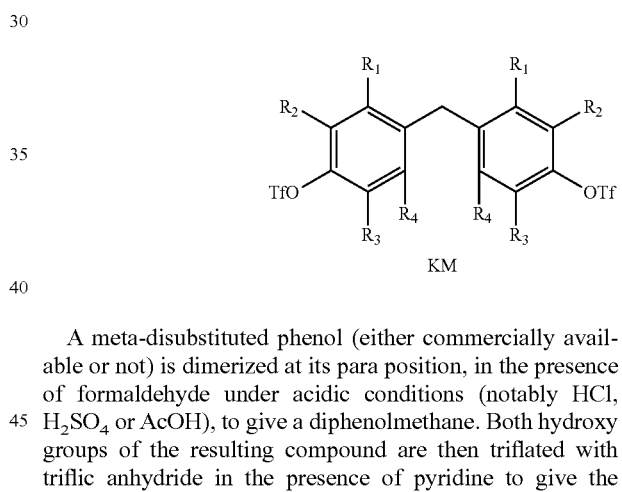

A meta-disubstituted phenol (either commercially available or not) is dimerized at its para position, in the presence of formaldehyde under acidic conditions (notably HCl, $H_2SO_4$ or AcOH), to give a diphenolmethane. Both hydroxy groups of the resulting compound are then triflated with triflic anhydride in the presence of pyridine to give the desired key methylene derivative, KM.

Compounds of the formula D (aryl extended ortho-substituted diphenylcarbenium) can be prepared from KM by the following Reaction Scheme 7bis, wherein X is an EDG:

Reaction Scheme 7bis

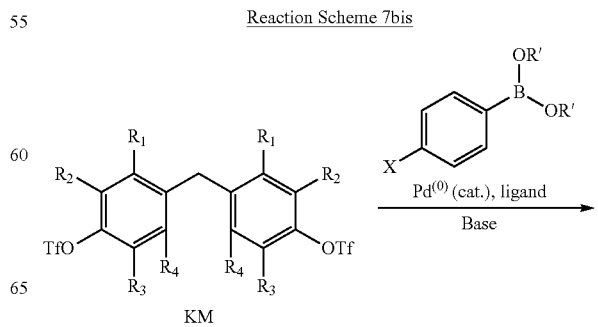

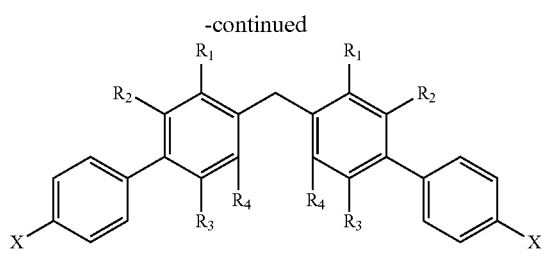

1) DDQ, THF
2) Metathesis

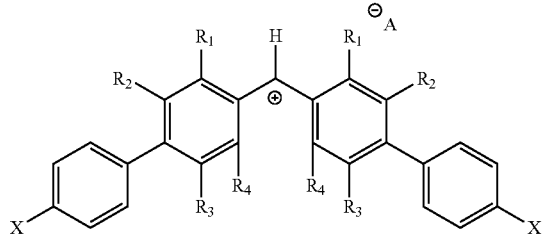

D

The previously described key methylene KM may be engaged in a double Suzuki cross-coupling by reacting with a suitable electron-rich boronic acid/ester (either commercially available or not) in the presence of a base and a palladium catalyst. The resulting extended methylene can then be oxidized with DDQ (or another suitable oxidant, which is here more particularly a hydride abstraction reagent) to directly produce the desired carbenium. A final step of metathesis may optionally be required to obtain the desired counteranion ($A^-$).

General Procedure E

Compounds of the formula E can be obtained from the key benzophenone (KB) precursor prepared by the previously detailed Reaction Scheme 6.

Compounds of the formula E (julolidine extended ortho-substituted diphenylcarbenium) can be prepared by the following Reaction Scheme 8, wherein X is an EDG:

Reaction Scheme 8

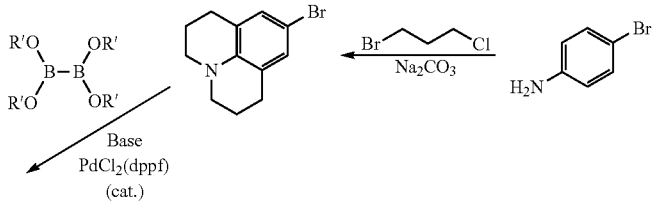

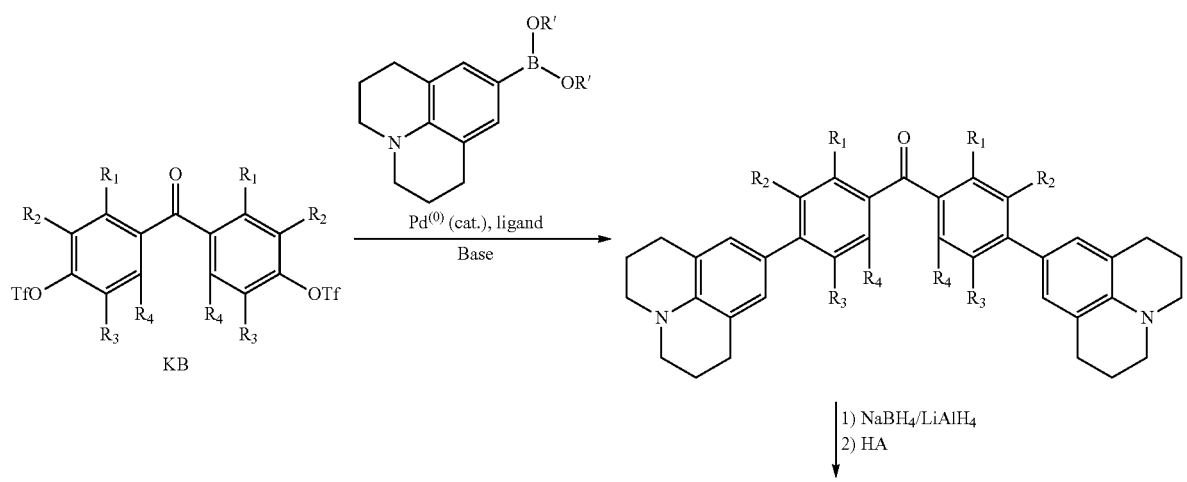

1) NaBH$_4$/LiAlH$_4$
2) HA

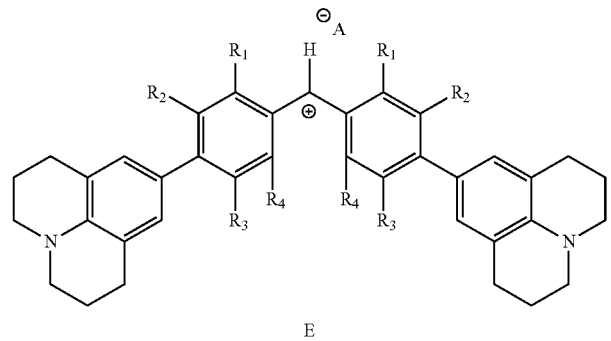

E

The key benzophenone precursor, KB, may be engaged in a double Suzuki cross-coupling by reacting with a julolidine moiety bearing a boronic acid/ester group in presence of a base and a palladium catalyst. The reacting julolidine is previously obtained from a classical Miyaura boration reaction on the bromojulolidine, itself synthesized according to a method described in the literature [Dance2008]. The resulting extended benzophenone can then be reduced (by either $NaBH_4$ or $LiAlH_4$) yielding the corresponding carbinol intermediate that can be itself easily dehydrated to produce the desired carbenium when reacted with acidic species (HA), the nature of which determines the identity of carbenium counteranion ($A^-$). The latter can be changed afterward by anion metathesis.

General Procedure Ebis

Compounds of the formula E can also be obtained from the key methylene (KM) precursor prepared by the previously detailed Reaction Scheme 6bis.

Compounds of the formula E (julolidine extended ortho-substituted diphenylcarbenium) can then be prepared by the following Reaction Scheme 8bis, wherein X is an EDG:

Reaction Scheme 8bis

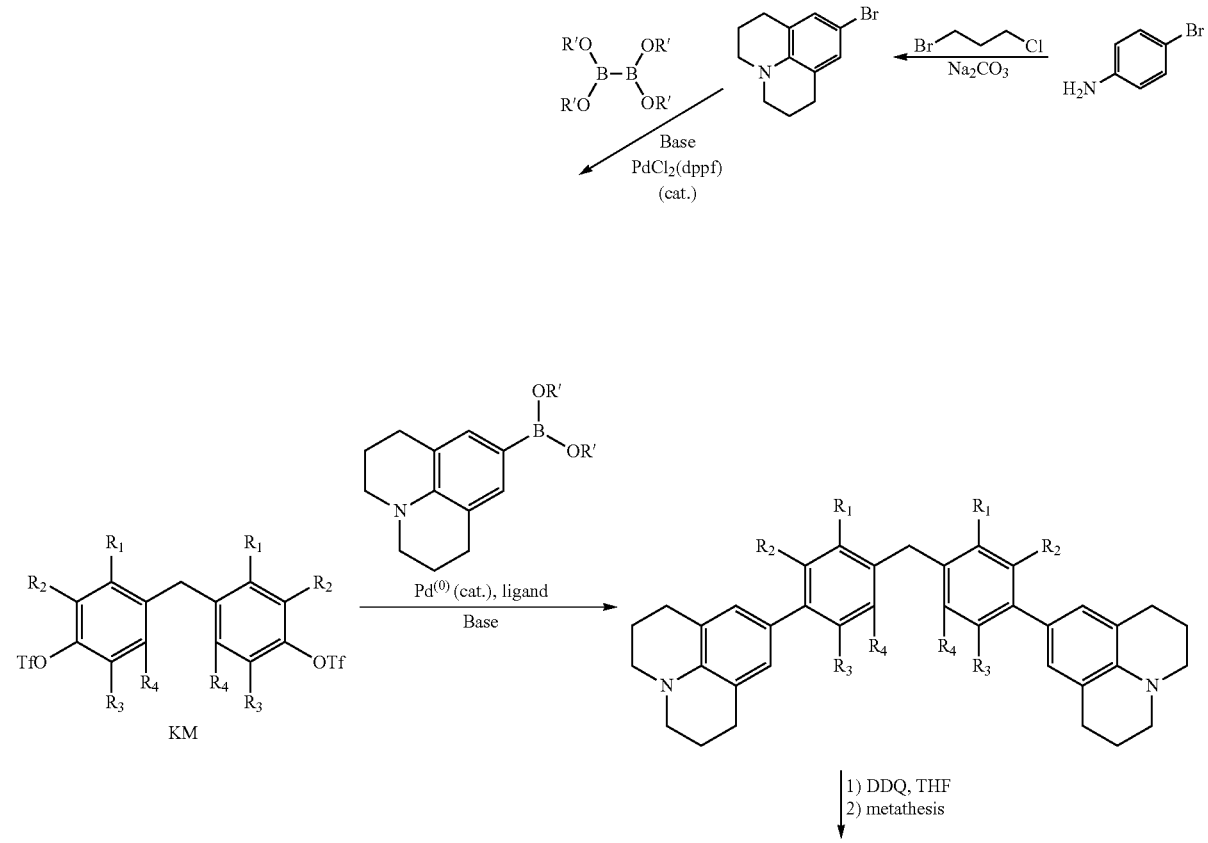

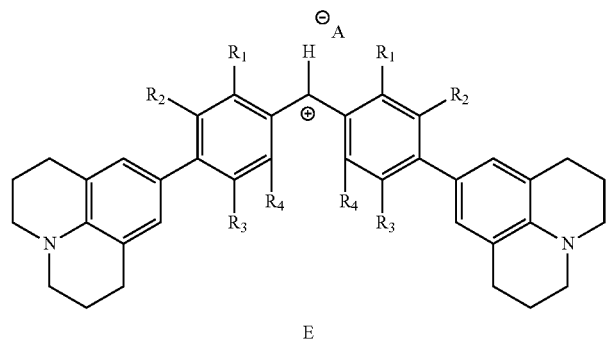

E

The key methylene precursor, KM, may be engaged in a double Suzuki cross-coupling by reacting with a julolidine moiety bearing a boronic acid/ester group in the presence of a base and a palladium catalyst. The resulting extended methylene can then be oxidized with DDQ (or another suitable oxidant, which is here more particularly a hydride abstraction reagent) to directly produce the desired carbenium. A final step of metathesis may optionally be required to obtain the desired counteranion (A⁻).

General Procedure F

Compounds of the formula F can be obtained from the key benzophenone (KB) precursor prepared by the previously detailed Reaction Scheme 6.

Compounds of the formula F (p-X-substituted styryl extended ortho-substituted diphenylcarbenium) can be prepared by the following Reaction Scheme 9, wherein X is an EDG:

Reaction Scheme 9

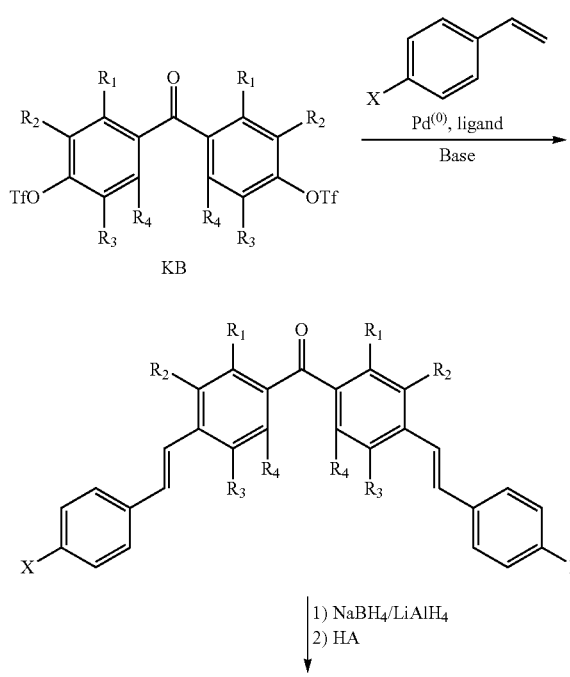

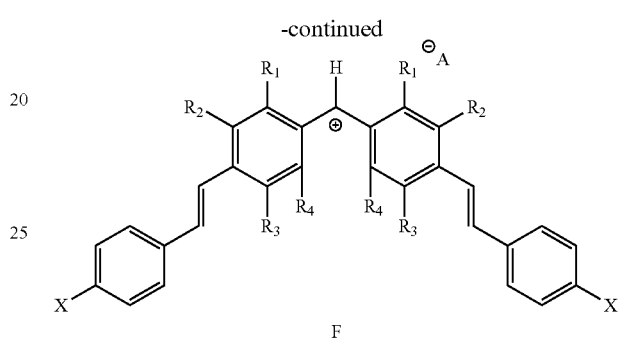

F

The key benzophenone KB may be engaged in a double Heck coupling by reacting with a p-EDG-substituted styryl precursor (either commercially available or not) in presence of a base and a palladium catalyst. The resulting extended benzophenone can then be reduced (by either NaBH₄ or LiAlH₄) yielding the corresponding carbinol intermediate that can be itself easily dehydrated to produce the desired carbenium when reacted with acidic species (HA), the nature of which determines the identity of carbenium counteranion (A⁻). The latter can be changed afterward by anion metathesis.

General Procedure Fbis

Compounds of the formula F can also be obtained from the key methylene (KM) precursor prepared by the previously detailed Reaction Scheme 6bis.

Compounds of the formula F (p-X-substituted styryl extended ortho-substituted diphenylcarbenium) can then be prepared by the following Reaction Scheme 9bis, wherein X is an EDG:

Reaction Scheme 9bis

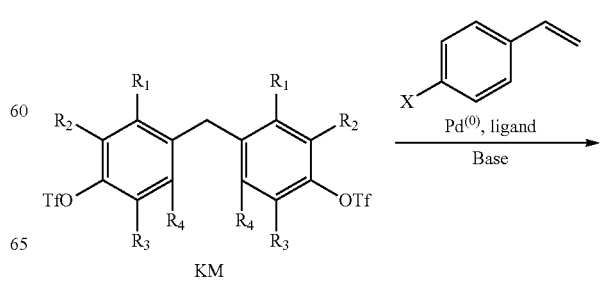

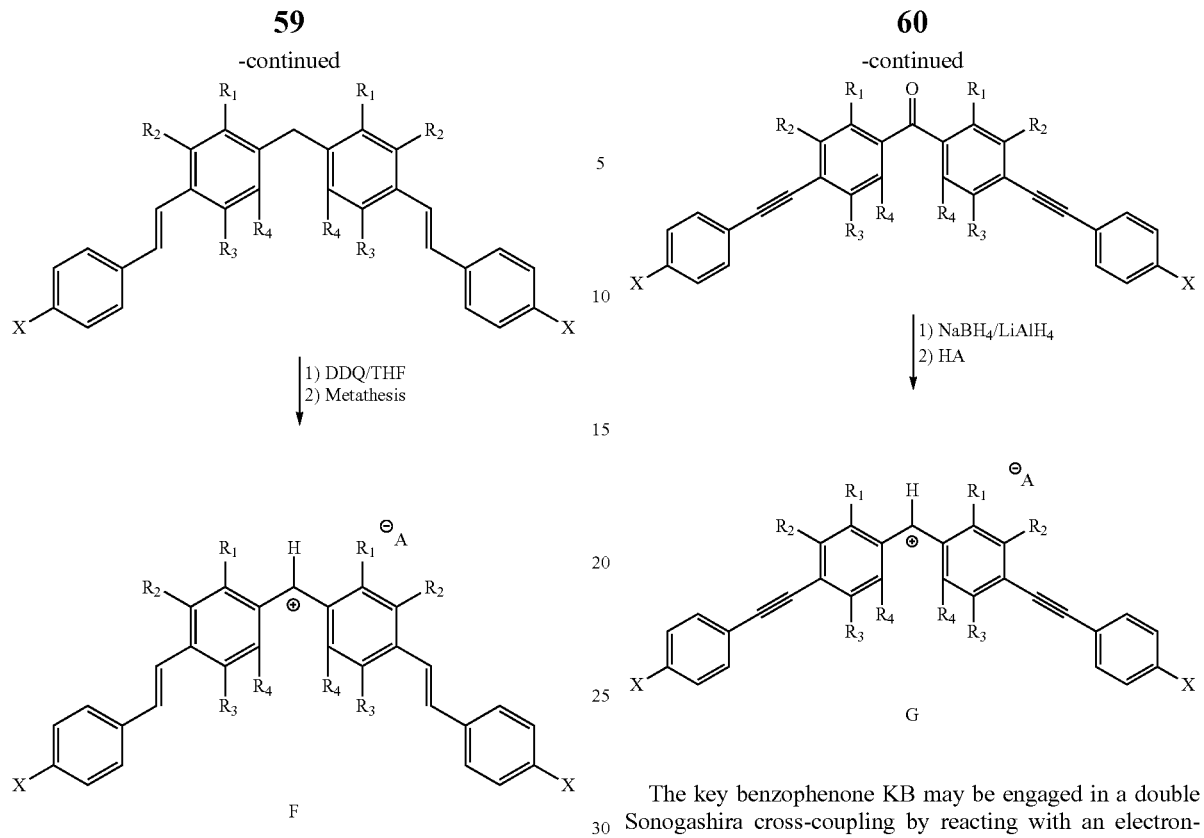

F

The key methylene KM may be engaged in a double Heck coupling by reacting with a p-EDG-substituted styryl precursor (either commercially available or not) in the presence of a base and a palladium catalyst. The resulting extended methylene can then be oxidized with DDQ (or another suitable oxidant, which is here more particularly a hydride abstraction reagent) to directly produce the desired carbenium. A final step of metathesis may optionally be required to obtain the desired counteranion (A⁻).

General Procedure G

Compounds of the formula G can be obtained from the key benzophenone (KB) precursor prepared by the previously detailed Reaction Scheme 6.

Compounds of the formula G (p-X-aryl ethynyl extended ortho-substituted diphenylcarbenium) can be prepared by the following Reaction Scheme 10, wherein X is an EDG:

G

The key benzophenone KB may be engaged in a double Sonogashira cross-coupling by reacting with an electron-rich p-EDG-substituted aryl ethynyl precursor (either commercially available or not) in presence of a base, Cu(I)-salt and a palladium catalyst. The resulting extended benzophenone can then be reduced (by either NaBH₄ or LiAlH₄) yielding the corresponding carbinol intermediate that can be itself easily dehydrated to produce the desired carbenium when reacted with acidic species (HA), the nature of which determines the identity of carbenium counteranion (A⁻). The latter can be changed afterward by anion metathesis.

General Procedure Gbis

Compounds of the formula G can also be obtained from the key methylene (KM) precursor prepared by the previously detailed Reaction Scheme 6bis.

Compounds of the formula G (p-X-aryl ethynyl extended ortho-substituted diphenylcarbenium) can be prepared by the following Reaction Scheme 10 Obis, wherein X is an EDG:

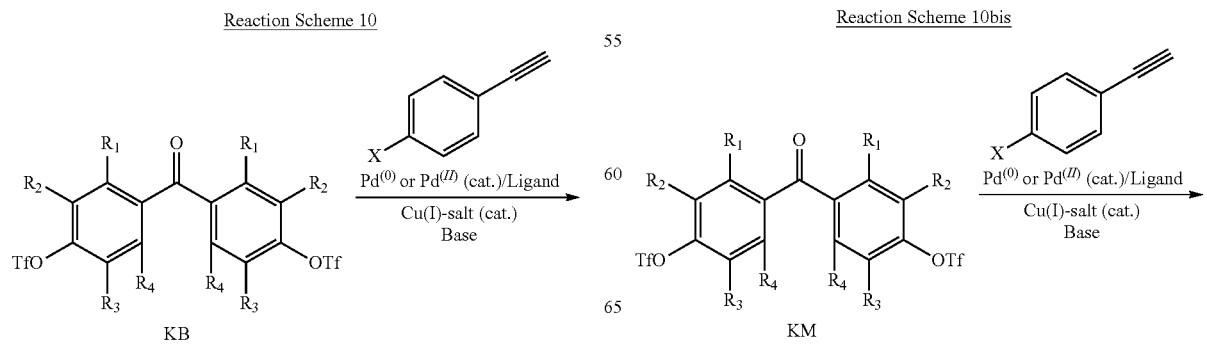

-continued

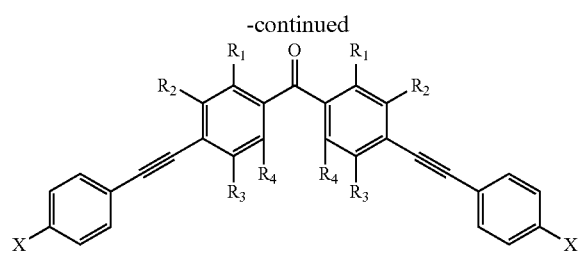

1) DDQ, THF
2) Metathesis

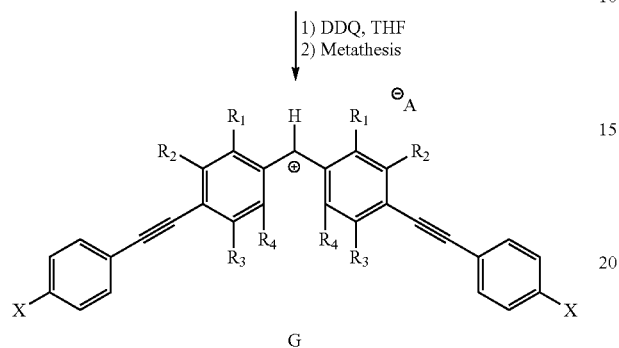

G

The key methylene KM may be engaged in a double Sonogashira cross-coupling by reacting with an electron-rich p-EDG-substituted aryl ethynyl precursor (either commercially available or not) in presence of a base, Cu(I)-salt and a palladium catalyst. The resulting extended methylene can then be oxidized with DDQ (or another suitable oxidant, which is here more particularly an hydride abstraction reagent) to directly produce the desired carbenium. A final step of metathesis may optionally be required to obtain the desired counteranion (A⁻).

General Procedure H

Compounds of the formula H (hindered ipso-aryl ortho-substituted diphenylcarbenium) can be prepared by the following Reaction Scheme 11, wherein X is an EDG:

Reaction Scheme 11

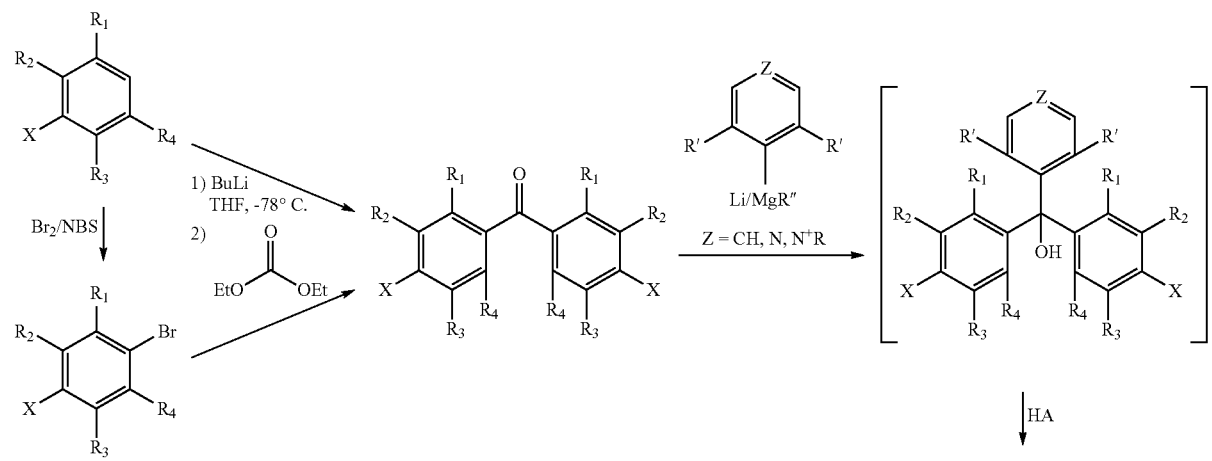

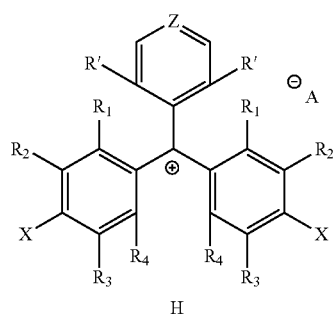

H

A meta-disubstituted electrodonating precursor (either commercially available or not) is engaged in a lithiation reaction. Depending on the nature of the starting material, a prior step of para bromination may be necessary, employing either Br$_2$ or NBS as reactive species [Zysman2009]. The lithiated intermediate is quenched with diethyl carbonate yielding a benzophenone which is further engaged in presence of a hindered organolithium/Grignard reactant [Wu2008]. The tertiary alcohol intermediate thus obtained is itself easily dehydrated to produce the desired carbenium when reacted with acidic species (HA), the nature of which determines the identity of carbenium counteranion (A$^-$). The latter can be changed afterward by anion metathesis.

General Procedure I

Compounds of the formula I (SiR$_2$-bridged ortho-substituted diphenylcarbenium) can be prepared by the following Reaction Scheme 12:

Reaction Scheme 12

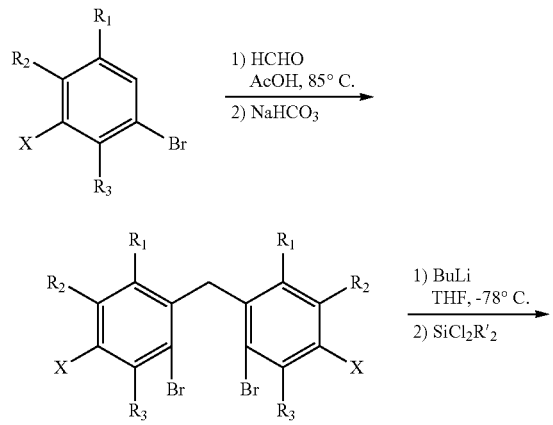

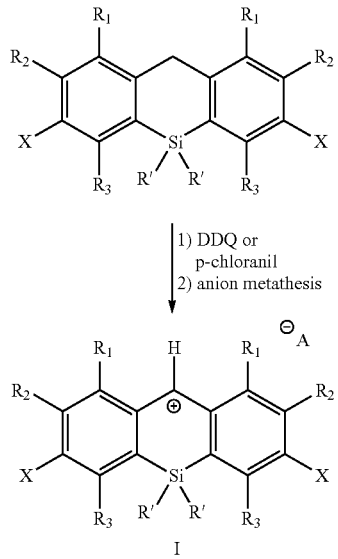

A meta-brominated meta-substituted electrodonating precursor (either commercially available or not) is engaged in a formaldehyde-mediated dimerization reaction to give the corresponding dibromo diarylmethane [Koide2011]. The bromine atoms are then exchanged in presence of BuLi in order to produce the corresponding dilithium intermediate which is quenched by addition of a disubstituted silicon dichloride reagent [Koide2011]. The resulting bridged diarylmethane is then oxidized with DDQ or p-chloranil (or another suitable oxidant, which is here more particularly an hydride abstraction reagent) to directly produce the desired carbenium. A final step of metathesis is required to obtain the desired counteranion (A$^-$).

General Procedure J

Compounds of the formula J (CMe$_2$-bridged ortho-substituted diphenylcarbenium) can be prepared by the following Reaction Scheme 13:

Reaction Scheme 13

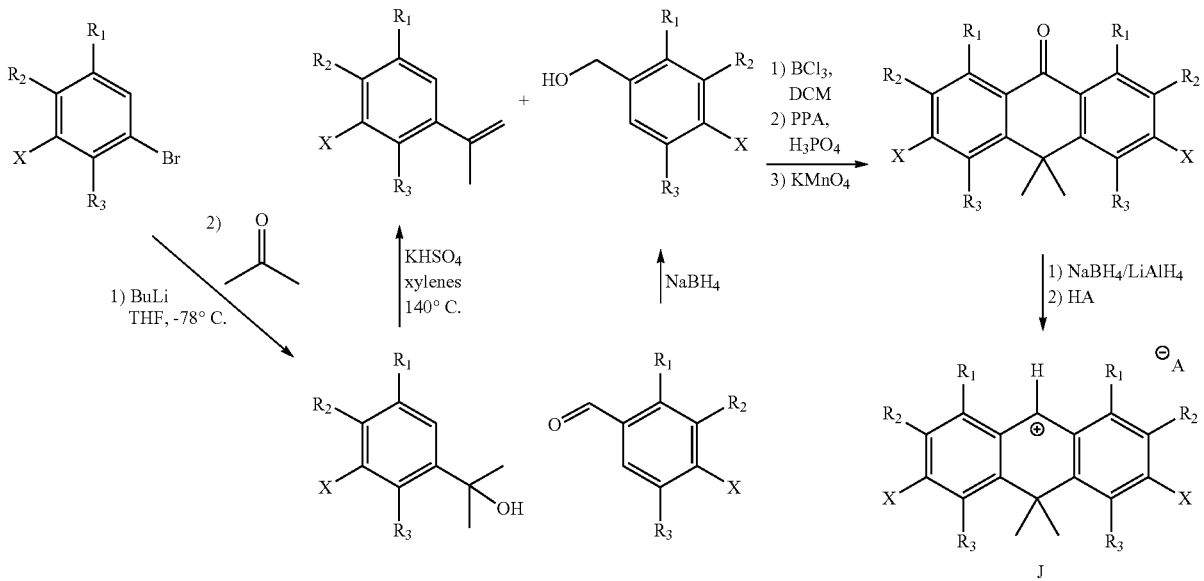

A meta-brominated meta-substituted electrodonating precursor (either commercially available or not) is engaged in a halogen-metal exchange reaction to produce the corresponding lithiated intermediate which is quenched by addition of dry acetone. The resulting tertiary alcohol is then dehydrated by heating in presence of KHSO₄ to give a methylene exo compound. The latter molecule is engaged with a closely related counterpart (but bearing a benzylic alcohol moiety) in a sequence of reactions allowing coupling and bridging of these two parts [Pastierik2014] and final oxidation with proper oxidant (e.g. KMnO₄) to yield the totally symmetric CMe₂-bridged benzophenone. This ketone is then reduced (by either NaBH₄ or LiAlH₄) yielding the corresponding carbinol intermediate that can be itself easily dehydrated to produce the desired carbenium when reacted with acidic species (HA), the nature of which determines the identity of carbenium counteranion (A⁻). The latter can be changed afterward by anion metathesis.

General Procedure K

Compounds of the formula K (three and more atoms-bridged ortho-substituted diphenylcarbenium) can be prepared by the following Reaction Scheme 14:

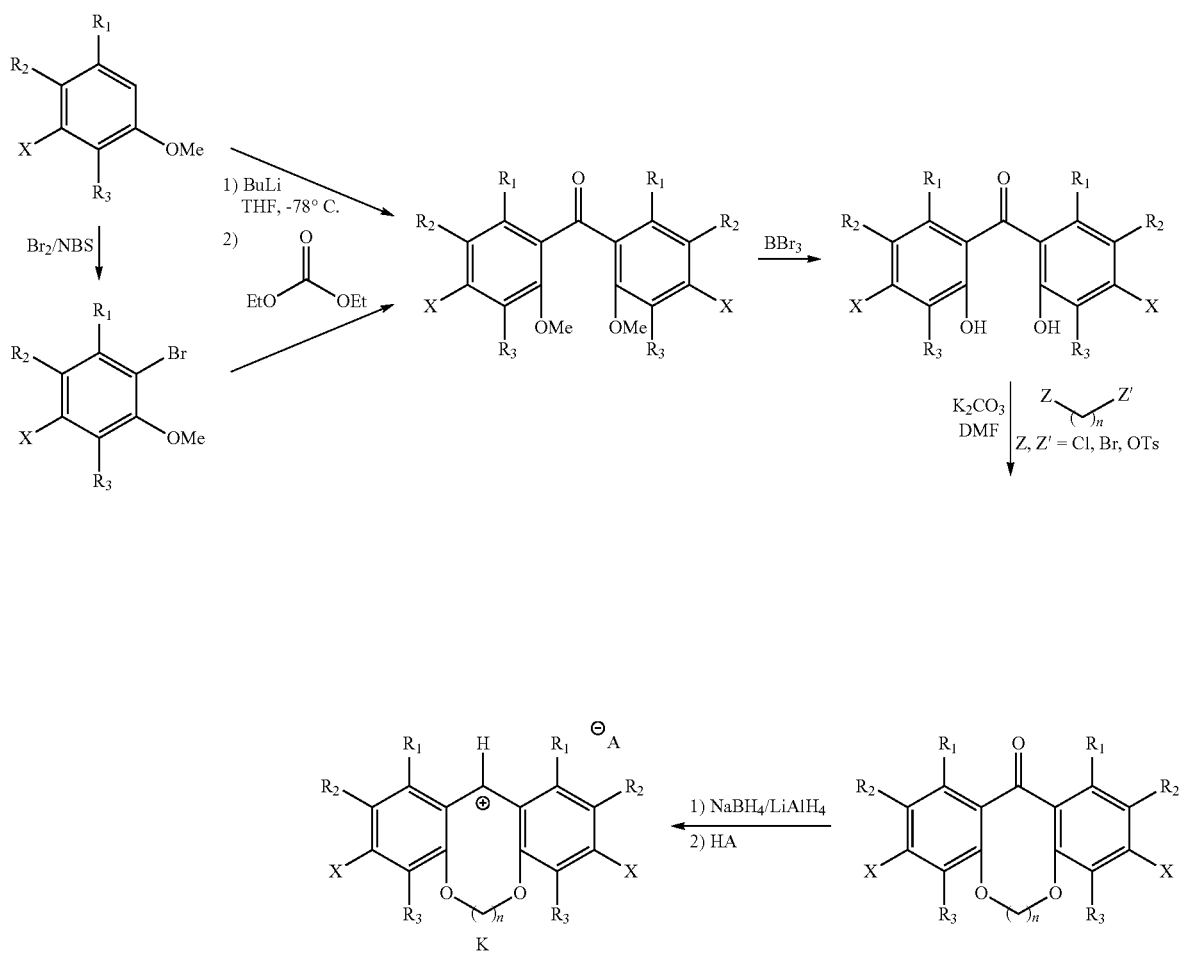

Reaction Scheme 14

A meta-methoxylated meta-substituted electrodonating precursor (either commercially available or not) is engaged in a lithiation reaction. Depending on the nature of the starting material, a prior step of para bromination may be necessary, employing either Br₂ or NBS as reactive species [Zysman2009]. The lithiated intermediate is quenched with diethyl carbonate yielding a dimethoxy benzophenone, which methoxy groups are subsequently demethylated by using BBr₃. The resulting phenol moieties are then bridged together through an aliphatic chain of length controlled by the nature of the reagent employed (e.g.: CH₂BrCl for n=1, TsO—(CH₂)₂-OTs for n=2) [Sorrell1997]. The resulting bridged benzophenone can then be reduced (by either NaBH₄ or LiAlH₄) yielding the corresponding carbinol intermediate that can be itself easily dehydrated to produce the desired carbenium when reacted with acidic species (HA), the nature of which determines the identity of carbenium counteranion (A⁻). The latter can be changed afterward by anion metathesis.

General Procedure Kbis

Compounds of the formula K (three and more atoms-bridged ortho-substituted diphenylcarbenium) can alternatively be prepared by the following Reaction Scheme 14bis:

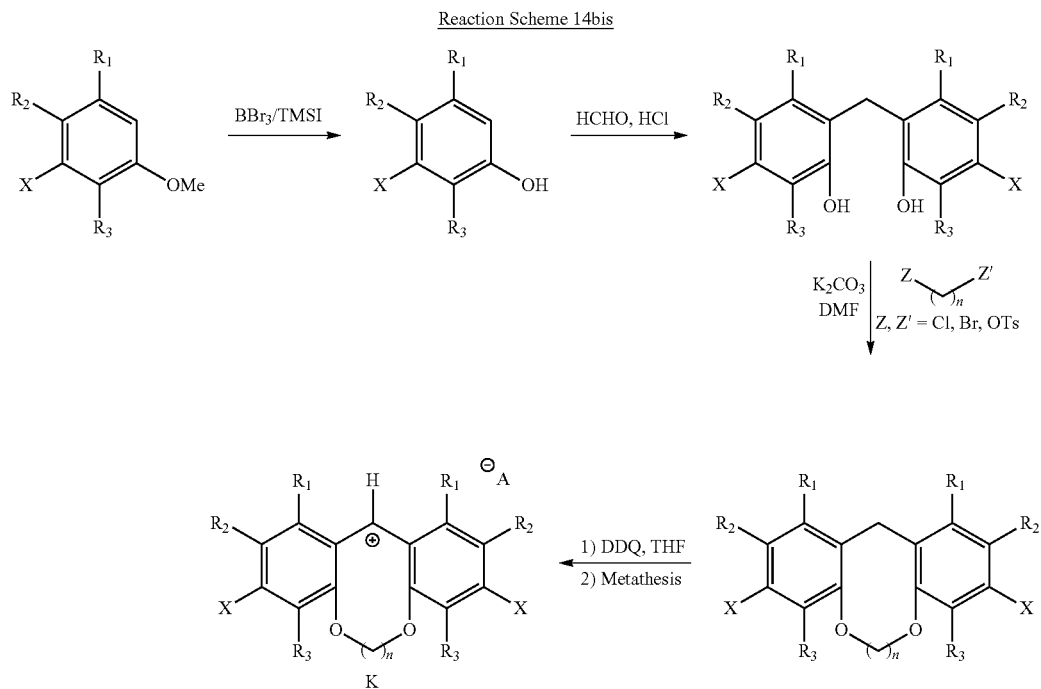

Reaction Scheme 14bis

A meta-methoxylated meta-substituted electrodonating precursor (either commercially available or not) is engaged in the presence of a demethylating agent (e.g. $BBr_3$ or TMSI) to give the corresponding phenol. The resulting compound was then dimerized at its para position, in the presence of formaldehyde under acidic conditions (notably HCl, $H_2SO_4$ or AcOH), to give a diphenolmethane. The hydroxyl groups are then bridged together through an aliphatic chain of length controlled by the nature of the reagent employed (e.g.: $CH_2BrCl$ for n=1, TsO—$(CH_2)_2$-OTs for n=2) [Sorrell1997]. The resulting bridged methylene can then be oxidized with DDQ (or another suitable oxidant, which is here more particularly an hydride abstraction reagent) to directly produce the desired carbenium. A final step of metathesis may optionally be required to obtain the desired counteranion ($A^-$).

General Procedure L

Compounds of the formula L (hindered ipso-alkyl ortho-substituted diphenylcarbenium) can be prepared by the following Reaction Scheme 15, wherein X is an EDG:

Reaction Scheme 15

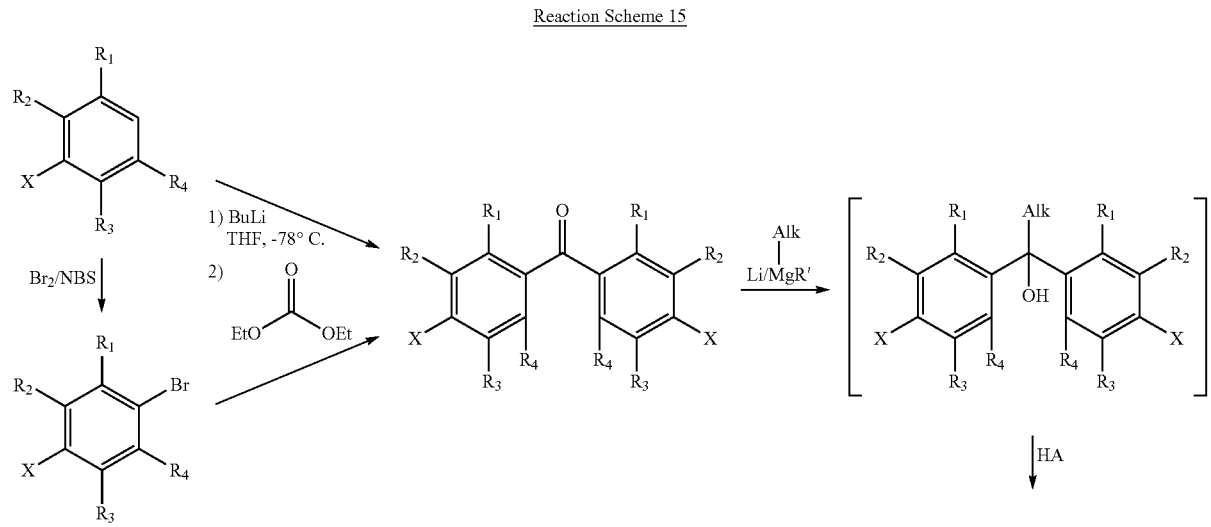

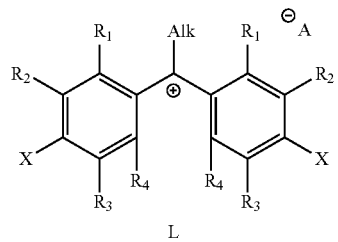

A meta-disubstituted electrodonating precursor (either commercially available or not) is engaged in a lithiation reaction. Depending on the nature of the starting material, a prior step of para bromination may be necessary, employing either $Br_2$ or NBS as reactive species [Zysman2009]. The lithiated intermediate is quenched with diethyl carbonate yielding a benzophenone which is further engaged in presence of an alkyl (either linear, branched or cyclic) organometallics. The tertiary alcohol intermediate thus obtained is itself easily dehydrated to produce the desired carbenium when reacted with acidic species (HA), the nature of which determines the identity of carbenium counteranion ($A^-$). The latter can be changed afterward by anion metathesis.

This procedure may be applied to acyclic or cyclic, substituted or unsubstituted alkyl groups. Therefore, the substituent "Alk" in the above reaction scheme 15 encompasses ($C_1$-$C_6$)alkyl, ($C_1$-$C_6$)haloalkyl, aryl-($C_1$-$C_6$)alkyl, heteroaryl-($C_1$-$C_6$)alkyl, cycloalkyl, cycloalkyl-($C_1$-$C_6$)alkyl, heterocycle and heterocycle-($C_1$-$C_6$)alkyl groups.

General Procedure M

Compounds of the formula M (hindered ipso-cyano ortho-substituted diphenylcarbenium) can be prepared by the following Reaction Scheme 16, wherein X is an EDG:

Reaction Scheme 16

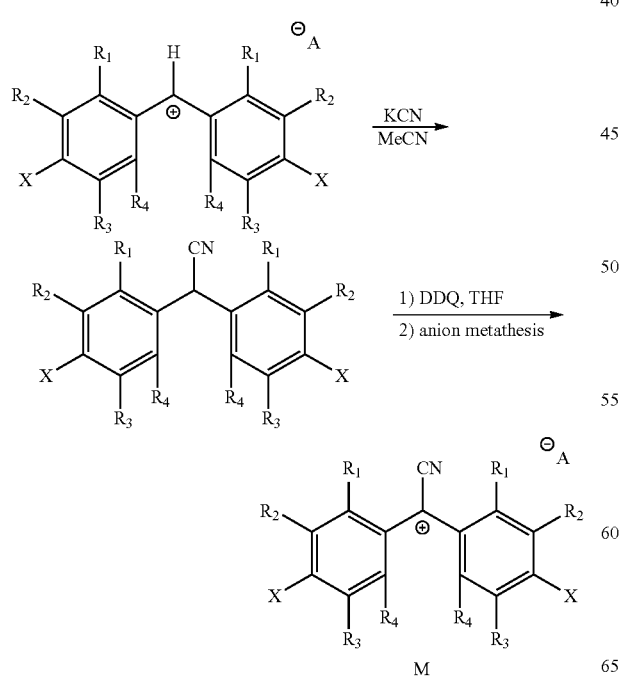

A methylium compound para-disubstituted with electrodonating groups X is engaged in a cyanation reaction, employing either KCN or another cyanide salt. The resulting neutral cyano compound can then be oxidized with DDQ (or another suitable oxidant, which is here more particularly a hydride abstraction reagent) to directly produce the desired carbenium. A final step of metathesis may optionally be required to obtain the desired counteranion ($A^-$).

References cited in the above described general procedures:

[Zysman2009]: Zysman-Colman, E., Arias, K., Siegel, J. S. Can. J. Chem., 2009, 87, 440-447. [Patents]: CA 2311064; U.S. Pat. No. 6,670,512

[Torricelli2013]: Torricelli, F., Bosson, J., Besnard, C., Chekini, M., Biirgi, T., Lacour, J. Angew. Chem. Int. Ed. 2013, 52, 1796-1800.

[Egawa2011]: Egawa, T., Koide, Y., Hanaoka, K., Komatsu, T., Terai, T., Nagano, T. Chem. Commun., 2011, 47, 4162-4164.

[Takahashi2002]: Takahashi, H., Kashiwa, N., Hashimoto, Y., Nagasawa, K. Tetrahedron Lett. 2002, 43, 2935-2938.

[Dance2008]: Dance, Z. E. X., Ahrens, M. J., Vega, A. M., Ricks, A. B., McCamant, D. W., Ratner, M. A., Wasielewski, M. R. J. Am. Chem. Soc. 2008, 130, 830-832.

[Wu2008]: Wu, L., Burgess, K. J. Org. Chem. 2008, 73, 8711-8718.

[Koide2011]: Koide, Y., Urano, Y., Hanaoka, K., Terai, T., Nagano, T. ACS Chem. Biol. 2011, 6, 600-608.

[Sorrell1997]: Sorrell, T. N., Yuan, H. J. Org. Chem. 1997, 62, 1899-1902.

[Pastierik2014]: Pastierik, T., Šebej, P., Medalová, J., Štacko, P., Klán, P. J. Org. Chem. 2014, 79, 3374-3382.

I-2. Examples of Syntheses of Compounds According to the Invention

I-2.i. Synthesis of Compounds 1, 2 and 3 According to General Procedure A

Compound 1-$PF_6^-$

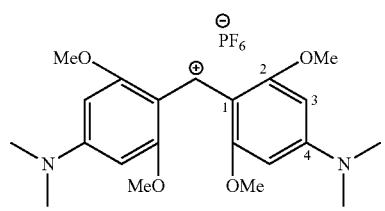

Bis(4-(dimethylamino)-2,6-dimethoxyphenyl)methylium hexafluorophosphate

To a solution of 3,5-dimethoxy-N,N-dimethylaniline (4.19 g, 23.15 mmol) in dry THF (40 mL) was added TMEDA (0.37 mL, 2.47 mmol, 0.1 equiv.). The solution was then cooled to −78° C., before dropwise addition of a 2.3 M n-BuLi solution in hexane (10.1 mL, 23.12 mmol, 1 equiv.). The suspension was stirred a few minutes at −78° C., then left to warm to room temperature and stirred for another 4 hours. The reaction mixture was then cooled to −78° C. and diluted with THF (60 mL) before dropwise addition of ethylformate (1.0 mL, 11.63 mmol, 0.48 equiv.). The mixture was stirred at room temperature under argon atmosphere overnight, then quenched with water and extracted with $CH_2Cl_2$. The organic layers were gathered, filtered on filter paper, and concentrated in vacuo without prior drying with $MgSO_4$. The crude oil thus obtained was dissolved in a minimum amount of EtOH, before dropwise addition of acidic solution made up of an aqueous solution of $HPF_6$ (60% in wt; 4.69 mL, 1.2 equiv.) diluted with EtOH (8 mL). To the dark blue solution was added a large amount of $Et_2O$ mixture (ca. 800 mL) whilst stirring vigorously. The supernatant was separated from the precipitate, which was dissolved in a minimum of MeCN (ca. 100 mL). To this solution was added a large amount of $Et_2O$ mixture (ca. 800 mL) whilst stirring vigorously. The dark blue precipitate was filtered off further purified by successive precipitation with $Et_2O$ from $CH_2Cl_2$ solutions to give the pure product. This compound was finally crystallized by slow vapor diffusion of $Et_2O$ into a MeCN solution of the chromophore (FIG. 2), affording shiny large columnar crystals with a gold-like metallic luster (FIGS. 4a, 4b and 4c) (2.14 g, 35.7% vs starting aniline derivative).

$^1H$ NMR (400 MHz, $CD_3CN$): δ 3.25 (s, 12H, $N(CH_3)_2$); 3.84 (s, 12H, $OCH_3$); 5.90 (s, 4H, $H_3$); 8.35 (s, 1H, $H_{(C+)}$).
$^{13}C$ NMR (100 MHz, $CD_3CN$): δ 41.5 ($N(CH_3)_2$); 57.0 ($OCH_3$); 89.6 ($C_3$); 112.1 ($C_1$); 143.4 ($CH^+$); 160.4 ($C_4$); 165.1 ($C_2$).

M=518.4301 g·mol$^{-1}$.

ESI-MS: m/z: calculated for $C_{21}H_{29}N_2O_4$: 373.2 $[M-PF_6]^+$; found 373.2 $[M-PF_6]^+$.
ESI-HRMS: m/z: calculated for $C_{21}H_{29}N_2O_4$: 373.2127 $[M-PF_6]^+$; found 373.2139 $[M-PF_6]^+$.
UV-vis-NIR ($CH_3CN$) $\lambda_{max}$/nm (ε/L mol$^{-1}$ cm$^{-1}$): 583 (88 000) (as can be seen in FIG. 1).

Crystal data: for $C_{21.33}H_{29.25}F_6N_{2.17}O_4P$, monoclinic, $P2_1$, a=15.2786(7), b=40.2601(16), c=24.1341(10) Å, α=90.000, β=102.7317(13), γ=90.000; V=14480.3, Z=24.

Compound 2-$PF_6^-$

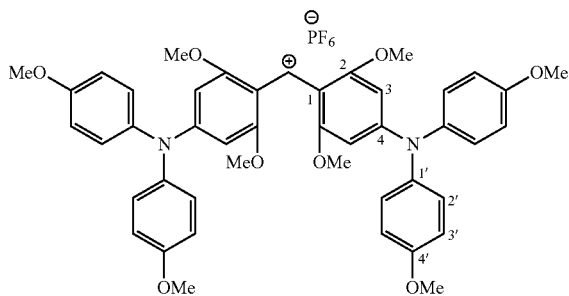

Bis(4-(dimethylamino)-2,6-dimethoxyphenyl)methylium hexafluorophosphate

To a solution of 3,5-dimethoxy-N,N-bis(4-methoxyphenyl)aniline (4.28 g, 11.7 mmol) in dry THF (20 mL) was added TMEDA (0.18 mL, 1.17 mmol, 0.1 equiv.). The solution was then cooled to −78° C., before dropwise addition of a 2.5 M n-BuLi solution in hexane (4.68 mL, 11.7 mmol, 1 equiv.). The suspension was stirred a few minutes at −78° C., then left to warm to room temperature and stirred for another 4 hours. The reaction mixture was then cooled to −78° C. and diluted with THF (40 mL) before dropwise addition of ethylformate (0.50 mL, 3.86 mmol, 0.5 equiv.). The mixture was stirred at room temperature under argon atmosphere overnight, then quenched with water and extracted with $CH_2Cl_2$. The organic layers were gathered, filtered on filter paper, and concentrated in vacuo without prior drying with $MgSO_4$. The crude oil thus obtained was dissolved in a minimum amount of EtOH, before dropwise addition of an acidic solution made up of an aqueous solution of $HPF_6$ (60% in wt; 2.4 mL, 1.2 equiv.) diluted with EtOH (8 mL). The dark blue-green solution was poured into a large amount of a Petroleum Ether/$Et_2O$ mixture (1:1 ratio; ca. 800 mL) whilst stirring vigorously. This operation was repeated as long as the supernatant remained green. The greenish-blue precipitate was filtered off and dissolved in a minimum amount of $CH_2Cl_2$ before being re-precipitated with a large amount of $Et_2O$. The supernatant that contains the target product was separated from the solid (precipitate), which is essentially a by-product. The combined blue layers were concentrated under reduced pressure to afford the expected product as a dark blue solid. Several recrystallizations were performed from a $CH_2Cl_2$/$Et_2O$ mixture, giving the pure product as greenish iridescent crystalline plates with a bronze luster (FIG. 5) (0.622 g, 12% vs starting aniline derivative).

$^1H$ NMR (400 MHz, $CD_3CN$): δ 3.59 (s, 12H, $OCH_3$ ($C_2$)); 3.81 (s, 12H, $OCH_3(C_{4'})$); 5.81 (s, 4H, $H_3$); 6.99-7.03 (m, 8H, $H_{3'}$); 7.25-7.29 (m, 8H, $H_{2'}$); 8.38 (s, 1H, $H_{(C+)}$).
$^{13}C$ NMR (100 MHz, $CD_3CN$): δ 56.3 ($OCH_3(C_{4'})$); 56.9 ($OCH_3$·($C_2$)); 93.0 ($C_3$); 114.3 ($C_1$); 116.2 ($C_{3'}$); 129.7 ($C_{2'}$); 137.6 ($CH^+$); 145.0 ($C_{1'}$); 160.0 ($C_{4'}$); 161.2 ($C_4$). 165.3 ($C_2$).

M=886.8116 g·mol$^{-1}$.

ESI-MS: m/z: calculated for $C_{45}H_{45}N_2O_8$: 741.3 $[M-PF_6]^+$; found 741.3 $[M-PF_6]^+$. ESI-HRMS: m/z: calculated for $C_{45}H_{45}N_2O_8$: 741.3176 $[M-PF_6]^+$; found 741.3141 $[M-PF_6]^+$.
UV-vis-NIR ($CH_3CN$) $\lambda_{max}$/nm (ε/L mol$^{-1}$ cm$^{-1}$): 630 (73 500) (as can be seen in FIG. 1).

Crystal data: for $C_{45}H_{45}F_6N_2O_8P$, triclinic, P1, a=10.2521 (3), b=10.7538(3), c=20.7783(6) Å, α=95.3451(9), β=98.3170(8), γ=108.9112(8); V=2120.21, Z=2.

Compound 3 Precursor

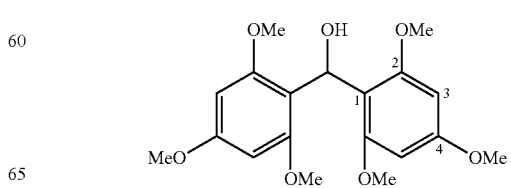

Bis(2,4,6-trimethoxyphenyl)methanol

To a solution of 1,3,5-trimethoxybenzene (5.50 g, 32.7 mmol) in THF (12 mL) was added hexane (5 mL) and TMEDA (0.49 mL, 3.27 mmol). To the solution thus obtained cooled at −78° C. was dropwise added a 2.5 M solution of n-butyllithium in hexane (15.7 mL, 39.2 mmol). The milky solution was stirred at room temperature for 4 h then cooled again at −78° C., diluted with THF (15 mL). To the cold solution was dropwise added ethylformate (1.32 mL, 1.64 mmol). The reaction mixture was stirred overnight at room temperature. To the solution cooled at 0° C. was added $H_2O$ (20 mL) and a 0.5 M aqueous solution of HCl (20 mL). The mixture was filtered off to afford the expected product as an off-white solid (1.135 g, 20%).

$^1$H NMR (400 MHz, $CDCl_3$): δ 3.75 (s, 12H, $OCH_3$); 3.77 (s, 6H, $OCH_3$); 5.39 (d, $^3J_{OH-CH}$=10.29 Hz, 1H, OH); 6.09 (s, 4H, $H_3$); 6.51 (d, $^3J_{5-OH}$=10.29 Hz, 1H, CH).

$^{13}$C NMR (100 MHz, $CDCl_3$): δ 55.3 ($OCH_3(C_4)$); 56.1 ($OCH_3(C_2)$); 64.1 ($C_3$); 113.9 ($C_1$); 159.1 ($C_2$); 159.8 ($C_4$).

ESI-MS: m/z: calculated for $C_{19}H_{24}O_7$: 364.2 $[M]^+$; found 364.0 $[M]^+$.

Compound 3-PF6−

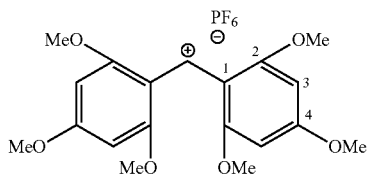

Bis(2,4,6-trimethoxyphenyl)methylium hexafluorophosphate

To bis(2,4,6-trimethoxyphenyl)methanol (1.00 g, 2.75 mmol) dissolved in ethanol was dropwise added an aqueous solution of $HPF_6$ (60% in wt, 0.5 mL). The colorless solution became dark red. A mixture (1:1 ratio) of petroleum ether and diethyl ether (200 mL) was added. The precipitate as a dark red solid was filtered off and was then dissolved in a minimum amount of acetone. A large amount of diethyl ether (500 mL) was added to this solution to give a dark red precipitate, which was filtered off. The solid was finally recrystallized from a mixture of $CH_2Cl_2$ and EtOAc, giving the pure expected product as dark-red needles with a slight silver-blue luster (0.773 g, 57%).

$^1$H NMR (400 MHz, $CD_3CN$): δ 3.94 (s, 12H, $OCH_3$ ($C_2$)); 4.08 (m, 6H, $OCH_3(C_4)$); 6.26 (s, 4H, $H_3$); 8.96 (s, 1H, H+).

$^{13}$C NMR (100 MHz, $CD_3CN$): δ 58.1 ($OCH_3(C_2)$); 58.4 ($OCH_3(C_4)$); 98.2 ($C_3$); 116.3 ($C_1$); 154.8 ($CH^+$); 167.7 ($C_2$); 176.6 ($C_4$).

M=492.3465 g $mol^{-1}$.

UV-vis-NIR ($CH_3CN$) $\lambda_{max}$/nm (ε/L $mol^{-1}$ $cm^{-1}$): 518.5 (39 500).

Crystal data: for $C_{19}H_{23}F_6O_6P$, orthorhombic, Pbca, a=23.5779(7), b=7.3015(2), c=24.9654(7) Å, α=90.000, β=90.000, γ=90.000; V=4297.89, Z=8.

I-2.ii. Synthesis of Compounds 1, 2, and 27 to 31 According to General Procedure Abis Synthesis of Diarylmethylene Precursors General procedure: In a two-necked 50 mL round-bottom flask fitted with a reflux condenser, was placed a properly substituted aniline (6.7 mmol) diluted by addition of methanol (8 mL). Hydrochloric acid (0.34 mL, 37%) was then added dropwise to this solution, before addition of formalin (0.25 mL, 37% in water), and the resulting mixture was refluxed overnight under argon atmosphere. After completion of the reaction followed by TLC, the mixture was allowed to cool to room temperature and neutralized by slow addition of a 1M aqueous solution of $NaHCO_3$ until pH 8 was reached. The mixture was then poured into 20 mL of distilled water and the resulting aqueous layer extracted three times with chloroform (3×40 mL). The organic layers were then combined, dried over $MgSO_4$ and filtered before removal of the solvent under reduced pressure. The residue was finally purified by flash chromatography to give the target methylene compound that often easily crystallizes.

Compound 1 Precursor

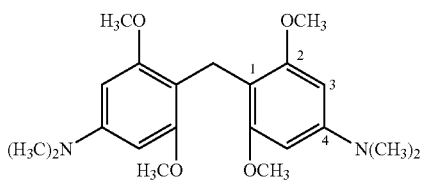

4,4'-methylenebis(3,5-dimethoxy-N,N-dimethylaniline)

The above general procedure was applied to 3,5-dimethoxy-N,N-dimethylaniline [Lee2009](3.11 g, 17.16 mmol). The title compound was purified via the Biotage Isolera One (silica-packed snap cartridge; 0-30% EtOAc/cyclohexane) and recrystallized as prismatic colorless crystals from a $CH_2Cl_2/Et_2O$ mixture (1.62 g, 50.3%).

$^1$H NMR (400 MHz, $CDCl_3$) δ 5.94 (s, 4H, $H_3$), 3.82 (s, 2H, $CH_2$), 3.71 (s, 12H, $OCH_3$), 2.90 (s, 12H, $N(CH_3)_2$).

$^{13}$C NMR (100 MHz, $CDCl_3$) δ 159.5 ($C_2$), 149.9 ($C_4$), 109.8 ($C_1$), 91.4 ($C_3$), 56.4 ($OCH_3$), 41.2 ($N(CH_3)_2$), 16.6 ($CH_2$).

HRMS: m/z: calcd for $C_{21}H_{30}N_2NaO_4$: 397.2098 $[M+Na]^+$; found: 397.2110 $[M+Na]^+$; calcd for $C_{42}H_{60}N_4NaO_8$: 771.4303 $[2M+Na]^+$; found: 771.4315 $[2M+Na]^+$.

Compound 2 Precursor

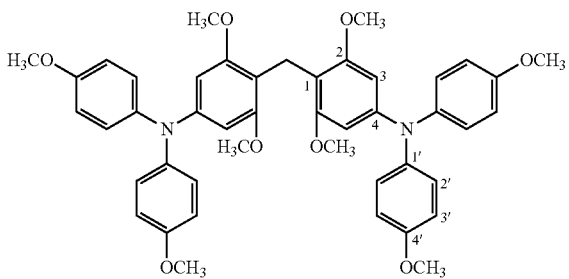 [SMILES: COc1ccc(N(c2ccc(OC)cc2)c2cc(OC)c(Cc3c(OC)cc(N(c4ccc(OC)cc4)c4ccc(OC)cc4)cc3OC)c(OC)c2)cc1]

4,4'-methylenebis(3,5-dimethoxy-N,N-bis(4-methoxyphenyl)aniline)

The above general procedure was applied to 3,5-dimethoxy-N,N-bis(4-methoxyphenyl)aniline [DellaPelle2014] (3.01 g, 8.24 mmol). The title compound was purified via the Biotage Isolera One (silica-packed snap cartridge; 0-10% EtOAc/cyclohexane) to give a white microcrystalline solid (0.75 g, 24.5%).

$^1$H NMR (300 MHz, CDCl$_3$): δ 7.10-6.98 (m, 8H, H$_{2'}$), 6.87-6.77 (m, 8H, H$_{3'}$), 6.16 (s, 4H, H$_3$), 3.88 (s, 2H, CH$_2$), 3.80 (s, 12H, OCH$_3$(C$_{4'}$)), 3.56 (s, 12H, OCH$_3$(C$_2$)).

$^{13}$C NMR (75 MHz, CDCl$_3$): δ 159.1 (C2). 155.3 (C$_{4'}$). 147.2 (C$_4$). 141.6 (C$_{1'}$), 126.0 (C$_{2'}$), 114.5 (C$_{3'}$), 113.2 (C$_1$), 99.5 (C$_3$), 56.1 (OCH$_3$(C$_2$)), 55.5 (OCH$_3$(C$_{4'}$)), 17.1 (CH$_2$).

HRMS: m/z: calcd for C$_{45}$H$_{46}$N$_2$NaO$_8$: 765.3146 [M+Na]$^+$; found: 765.3167 [M+Na]$^+$.

Compound 27 Precursor

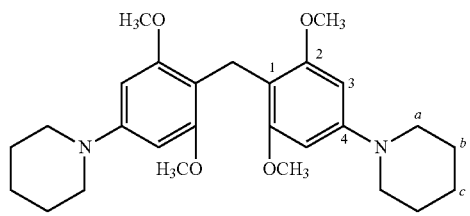 [SMILES: COc1cc(N2CCCCC2)cc(OC)c1Cc1c(OC)cc(N2CCCCC2)cc1OC]

Bis(2,6-dimethoxy-4-(piperidin-1-yl)phenyl)methane

The above general procedure was applied to 1-(3',5'-dimethoxyphenyl)piperidine [Lü2011](3.91 g, 17.67 mmol). The title compound was purified via the Biotage Isolera One (silica-packed snap cartridge; 0-30% EtOAc/cyclohexane) and recrystallized as prismatic colorless crystals from a CH$_2$Cl$_2$/Et$_2$O mixture (2.37 g, 59%).

$^1$H NMR (400 MHz, CDCl$_3$) δ 6.13 (s, 4H, H$_3$), 3.82 (s, 2H, CH$_2$), 3.68 (s, 12H, OCH$_3$), 3.08 (t, $^3J_{a-b}$=5.4 Hz, 8H, H$_a$), 1.74-1.67 (m, 8H, H$_b$), 1.59-1.51 (m, 4H, H$_c$).

$^{13}$C NMR (100 MHz, CDCl$_3$) δ 159.2 (C$_2$), 151.6 (C$_4$), 112.1 (C$_1$), 94.9 (C$_3$), 56.3 (OCH$_3$), 51.7 (C$_a$), 26.2 (C$_b$), 24.5 (C$_c$), 16.9 (CH$_2$).

HRMS: m/z: calcd for C$_{27}$H$_{39}$N$_2$O$_4$: 455.2904 [M+H]$^+$; found: 455.2922 [M+H]$^+$. Crystal data: for C$_{27}$H$_{38}$N$_2$O$_4$, monoclinic, C2/c, a=18.2443(6), b=13.1592(4), c=10.8058(3) Å, α=90.000, β=108.358(2), γ=90.000; V=2462.23, Z=4.

Compound 28 Precursor

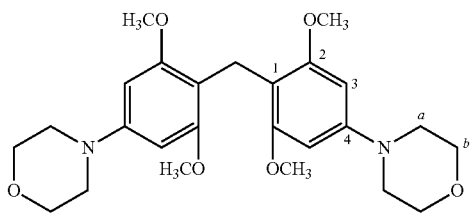 [SMILES: COc1cc(N2CCOCC2)cc(OC)c1Cc1c(OC)cc(N2CCOCC2)cc1OC]

Bis(2,6-dimethoxy-4-morpholinophenyl)methane

The above general procedure was applied to 4-(3',5'-dimethoxyphenyl)morpholine [Lü2011](7.57 g, 33.90 mmol). The title compound was purified via the Biotage Isolera One (silica-packed snap cartridge; 0-30% EtOAc/cyclohexane) and recrystallized as prismatic colorless crystals from AcOEt (3.55 g, 45.7%).

$^1$H NMR (400 MHz, CDCl$_3$) δ 6.09 (s, 4H, H$_3$), 3.87-3.82 (m, 10H, H$_b$+CH$_2$), 3.69 (s, 12H, OCH$_3$), 3.11 (t, $^3J_{a-b}$=4.8 Hz, 8H, H$_a$).

$^{13}$C NMR (100 MHz, CDCl$_3$) δ 159.3 (C$_2$), 150.5 (C$_4$), 112.4 (C$_1$), 93.8 (C$_3$), 67.1 (H$_b$), 56.2 (OCH$_3$), 50.2 (H$_a$), 16.8 (CH$_2$).

HRMS: m/z: calcd for C$_{25}$H$_{35}$N$_2$O$_6$: 459.2490 [M+H]$^+$; found: 459.2502 [M+H]$^+$. Crystal data: for C$_{25}$H$_{34}$N$_2$O$_6$(H$_2$O)$_{0.25}$, monoclinic, P2/c, a=10.9761(8), b=13.8118(11), c=16.4099(11) Å, α=90.000, β=104.133(2), γ=90.000; V=2412.44, Z=4.

Compound 29 Precursor

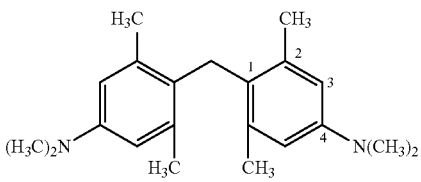

4,4'-methylenebis(N,N,3,5-tetramethylaniline)

The above general procedure was applied to commercially available N,N,3,5-tetramethylaniline (5.8 g, 38.86 mmol). The title compound was purified via the Biotage Isolera One (silica-packed snap cartridge; 0-30% EtOAc/cyclohexane) and recrystallized as prismatic colorless crystals from CH$_2$Cl$_2$/Et$_2$O (5.31 g, 88%).

$^1$H NMR (300 MHz, CDCl$_3$) δ 6.41 (s, 4H, H$_3$), 3.92 (s, 2H, CH$_2$), 2.91 (s, 12H, N(CH$_3$)$_2$), 2.11 (s, 12H, CH$_3$).

$^{13}$C NMR (75 MHz, CDCl$_3$) δ 148.7 (C$_4$), 137.6 (C$_2$), 127.4 (C$_1$), 113.6 (C$_3$), 41.0 (N(CH$_3$)$_2$), 30.1 (CH$_2$), 21.5 (CH$_3$).

HRMS: m/z: calcd for C$_{21}$H$_{31}$N$_2$: 311.2482 [M+H]$^+$; found: 311.2480 [M+H]$^+$.

Crystal data: for C$_{21}$H$_{30}$N$_2$, orthorhombic, Pbca, a=13.7462(4), b=12.3537(3), c=21.7385(6) Å, α=90.000, β=90.000, γ=90.000; V=3691.55(17), Z=8.

Compound 30 Precursor

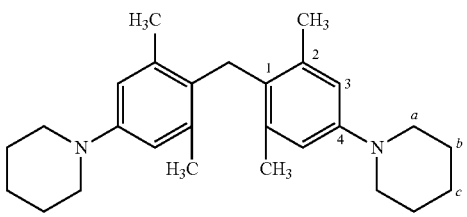 [SMILES: Cc1cc(N2CCCCC2)cc(C)c1Cc1c(C)cc(N2CCCCC2)cc1C]

Bis(2,6-dimethyl-4-(piperidin-1-yl)phenyl)methane

The above general procedure was applied to 1-(3,5-dimethylphenyl)piperidine [Hatakeyama2010] (7.30 g, 38.56 mmol). The title compound was purified by simply washing the crude product with Et$_2$O and then recrystallized as prismatic colorless crystals from AcOEt (4.5 g, 59.8%).

$^1$H NMR (400 MHz, CDCl$_3$) δ 6.58 (s, 4H, H$_3$), 3.91 (s, 2H, CH$_2$), 3.09 (t, $^3$J$_{a-b}$=5.4 Hz, 8H, H$_a$), 2.08 (s, 12H, CH$_3$), 1.75-1.66 (m, 8H, H$_b$), 1.59-1.51 (m, 4H, H$_c$).

$^{13}$C NMR (100 MHz, CDCl$_3$) δ 150.0 (C$_4$), 137.5 (C$_2$), 129.7 (C$_1$), 117.2 (C$_3$), 51.2 (C$_a$), 30.4 (CH$_2$), 26.1 (C$_b$), 24.5 (C$_c$), 21.4 (CH$_3$).

HRMS: m/z: calcd for C$_{27}$H$_{39}$N$_2$: 391.3108 [M+H]$^+$; found: 391.3104 [M+H]$^+$.

Crystal data: for C$_{27}$H$_{38}$N$_2$, monoclinic, P2$_1$/c, a=11.4761 (5), b=21.1140(8), c=19.6436(9) Å, α=90.000, β=105.544 (2), γ=90.000; V=4585.68, Z=8.

Compound 31 Precursor

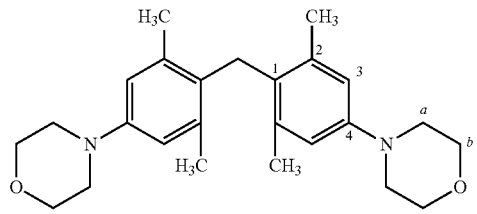 [SMILES: Cc1cc(N2CCOCC2)cc(C)c1Cc1c(C)cc(N2CCOCC2)cc1C]

Bis(2,6-dimethyl-4-morpholinophenyl)methane

The above general procedure was applied to 4-(3,5-dimethylphenyl)morpholine [Wolfe2000](5.13 g, 26.82 mmol). Crude product was washed with cyclohexane and recrystallized to afford the title compound as prismatic colorless crystals from CH$_2$Cl$_2$/Et$_2$O (3.25 g, 61.4%).

$^1$H NMR (400 MHz, CDCl$_3$) δ 6.56 (s, 4H, H$_3$), 3.93 (s, 2H, CH$_2$), 3.86 (t, $^3$J$_{b-a}$=4.8 Hz, 8H, H$_b$), 3.12 (t, $^3$J$_{a-b}$=4.8 Hz, 8H, H$_a$), 2.10 (s, 12H, CH$_3$).

$^{13}$C NMR (100 MHz, CDCl$_3$) δ 149.0 (C$_4$), 137.8 (C$_2$), 130.2 (C$_1$), 116.3 (C$_3$), 67.1 (C$_b$), 49.8 (C$_a$), 30.5 (CH$_2$), 21.5 (CH$_3$).

HRMS: m/z: calcd for C$_{25}$H$_{35}$N$_2$O$_2$: 395.2693 [M+H]$^+$; found: 395.2705 [M+H]$^+$.

Synthesis of Target Compounds from the Above Precursors:

General procedure for the synthesis of target compounds: To a vigorously stirred solution of the proper methylene compound in a minimum amount of THF was dropwise added a solution of oxidant (here more particularly an hydride abstraction reagent) in THF, preferably 2,3-dichloro-5,6-dicyano-1,4-benzoquinone (DDQ) (1.0 equivalent). After stirring for approximately 2.5 h at room temperature, the reaction mixture was concentrated under reduced pressure and then dropwise added (after previous filtration through a pipette plugged with cotton wool) to a saturated solution of the desired counteranion, e.g. potassium hexafluorophosphate (metathesis of DDQH$^-$/PF$_6^-$). This suspension was stirred for 20 minutes before filtration of the dark precipitate, which was taken up in CH$_2$Cl$_2$. The resulting deeply (blue-)colored organic layer was washed with a minimum amount of distilled water (until giving a colorless aqueous layer) and concentrated under reduced pressure. The residue was finally purified by slow vapor crystallization. Noticingly, the final metathesis may be avoided to afford the methylium compound associated to a counteranion derived from the reduced form of the oxidant sooner utilized, e.g. DDQH$^-$.

Compound 27-DDQH$^-$

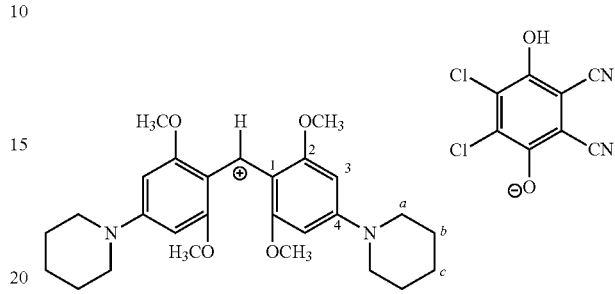

Bis(2,6-dimethoxy-4-(piperidin-1-yl)phenyl)methylium 2,3-dichloro-5,6-dicyano-4-hydroxyphenolate The above general procedure for the synthesis of target compounds was applied to the previously described bis(2,6-dimethoxy-4-(piperidin-1-yl)phenyl)methane (2.48 g, 5.45 mmol) to yield the title compound that was simply filtered from the reaction mixture to give a shiny microcrystalline solid (affording a blue solution) (2.79 g, 75%) that was recrystallized from CH$_3$CN/Et$_2$O as greenish iridescent crystalline plates with a bronze luster.

$^1$H NMR (300 MHz, DMSO-d$_6$) δ 8.13 (s, 1H, CH$^+$), 6.13 (s, 4H, H$_3$), 3.82 (s, 12H, OCH$_3$), 3.77-3.65 (m, 8H, H$_a$), 1.76-1.57 (m, 12H, H$_b$+H$_c$).

$^{13}$C NMR (75 MHz, DMSO-d$_6$) δ 163.9 (C$_2$), 158.0 (C$_4$), 140.1 (CH$^+$), 111.0 (C$_1$), 89.2 (C$_3$), 56.4 (OCH$_3$), 48.6 (C$_a$), 25.9 (C$_b$), 23.8 (C$_c$).

Compound 27-PF$_6^-$

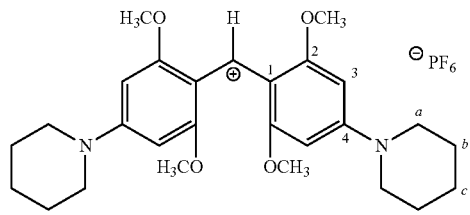 [SMILES: COc1cc(N2CCCCC2)cc(OC)c1[CH+]c1c(OC)cc(N2CCCCC2)cc1OC ; "PF6"]

Bis(2,6-dimethoxy-4-(piperidin-1-yl)phenyl)methylium hexafluorophosphate

A small quantity (1.79 g, 2.64 mmol) of the previously described bis(2,6-dimethoxy-4-(piperidin-1-yl)phenyl) methylium 2,3-dichloro-5,6-dicyano-4-hydroxy-phenolate was engaged in a metathesis step using potassium hexafluorophosphate The title compound was purified by discarding remaining impurities loosely soluble in CH$_2$Cl$_2$ and recrystallized by slow diffusion of Et$_2$O in a concentrated CH$_3$CN solution to yield the desired carbenium as greenish iridescent crystalline plates with a bronze luster (1.0 g, 63.3%).

¹H NMR (400 MHz, CD₃CN) δ 8.26 (s, 1H, CH⁺), 6.03 (s, 4H, H₃), 3.82 (s, 12H, OCH₃), 3.71-3.66 (m, 8H, H$_a$), 1.76-1.68 (m, 12H, H$_b$+H$_c$).

¹³C NMR (100 MHz, CDCl₃) δ 165.4 (C₂), 159.5 (C₄), 142.2 (CH⁺), 112.5 (C₁), 90.2 (C₃), 57.0 (OCH₃), 49.9 (C$_a$), 26.9 (C$_b$), 24.9 (C$_c$).

HRMS (ESI+): m/z: calcd for C₂₇H₃₇N₂O₄: 453.2748 [M-PF₆]⁺; found: 453.2745 [M-PF₆]⁺.

HRMS (ESI−): m/z: calcd for F₆P: 144.9647 [PF₆]⁻; found: 145.0529 [PF₆]⁻.

UV-vis-NIR (CH₃CN) λmax/nm (ε/L mol⁻¹ cm⁻¹): 592 (92 419) (as can be seen in FIG. 6).

Compound 28-PF₆⁻

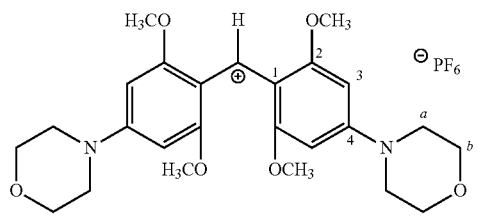 [SMILES: COc1cc(N2CCOCC2)cc(OC)c1[CH+]c1c(OC)cc(N2CCOCC2)cc1OC ; "PF6"]

Bis(2,6-dimethoxy-4-morpholinophenyl)methylium hexafluorophosphate

The above general procedure for the synthesis of target compounds was applied to bis(2,6-dimethoxy-4-morpholinophenyl)methane (1.00 g, 2.18 mmol). The title compound was purified by discarding remaining impurities loosely soluble in CH₂Cl₂ and recrystallized by slow diffusion of Et₂O in a concentrated CH₃CN solution to yield the desired carbenium as shiny large columnar crystals with a green metallic luster (1.02 g, 77.7%).

¹H NMR (300 MHz, CD₃CN) δ 8.34 (s, 1H, CH⁺), 6.04 (s, 4H, H₃), 3.84 (s, 12H, OCH₃), 3.82-3.77 (dd, ³J$_{a-b}$=4.5 Hz, 8H, H$_b$), 3.69-3.65 (dd, ³J$_{b-a}$=4.5 Hz, 8H, H$_a$).

¹³C NMR (100 MHz, CDCl₃) δ 165.5 (C₂), 160.4 (C₄), 143.7 (CH⁺), 113.3 (C₁), 90.4 (C₃), 67.1 (C$_b$), 57.1 (OCH₃), 48.7 (C$_a$).

HRMS (ESI+): m/z: calcd for C₂₅H₃₃N₂O₆: 457.2333 [M-PF₆]⁺; found: 457.2351 [M-PF₆]⁺.

HRMS (ESI−): m/z: calcd for F₆P: 144.9647 [PF₆]⁻; found: 145.0727 [PF₆]⁻.

UV-vis-NIR (CH₃CN) λmax/nm (ε/L mol⁻¹ cm⁻¹): 586 (79 860) (as can be seen in FIG. 6).

Crystal data: for C₂₅H₃₃F₆N₂O₆P·CH₃CN, monoclinic, P2₁/c, a=12.2406(3), b=16.9800(3), c=15.1295(3) Å, α=90.000, β=109.7300(10), γ=90.000; V=2959.9, Z=4.

Compound 29-DDQH⁻

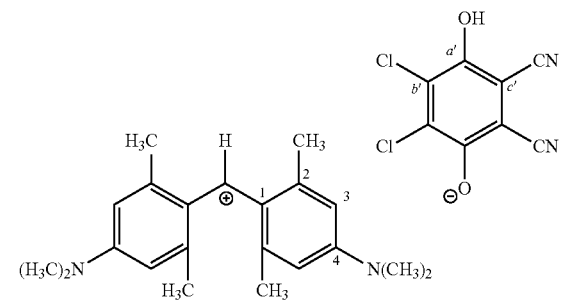

Bis(4-(dimethylamino)-2,6-dimethylphenyl)methylium 2,3-dichloro-5,6-dicyano-4-hydroxyphenolate The above general procedure for the synthesis of target compounds was applied to 4,4′-methylenebis(N,N,3,5-tetramethylaniline) (5.99 g, 19.29 mmol) to yield the title compound that was simply filtered from the reaction mixture to give a brown solid (affording a blue solution) (7.0 g, 67.5%) that that appears under microscope as shiny tiny crystals with a gold-like metallic luster.

¹H NMR (400 MHz, DMSO-d₆) δ 8.35 (s, 1H, CH⁺), 6.77 (s, 4H, H₃), 3.27 (s, 12H, N(CH₃)₂), 2.20 (s, 12H, CH₃).

¹³C NMR (100 MHz, DMSO-d₆) δ 155.8 (CH⁺), 155.7 (C₄), 145.9 (C₂), 128.8 (C₁), 114.2 (C₃), 40.6 (N(CH₃)₂), 21.2 (CH₃).

HRMS (ESI+): m/z: calcd for C₂₁H₂₉N₂: 309.2325 [M-DDQH]⁺; found: 309.2313 [M-DDQH]⁺.

HRMS (ESI−): m/z: calcd for C₈HCl₂N₂O₂: 226.9421 [DDQH]⁻; found: 227.1023 [DDQH]⁻.

Compound 29-PF₆⁻

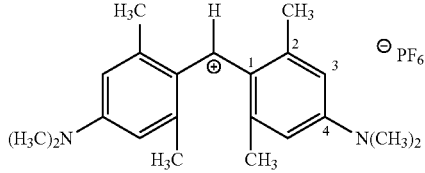

Bis(4-(dimethylamino)-2,6-dimethylphenyl)methylium hexafluorophosphate

A small quantity (2.0 g, 3.73 mmol) of the previously described bis(4-(dimethylamino)-2,6-dimethylphenyl)methylium 2,3-dichloro-5,6-dicyano-4-hydroxyphenolate was engaged in a metathesis step using potassium hexafluorophosphate. The crude product was washed with chloroform and AcOEt and recrystallized from CH₂Cl₂/Et₂Ot to give the title compound as shiny large crystalline plates with a gold-like metallic luster (1.1 mg, 65%).

¹H NMR (300 MHz, CD₃CN) δ 8.39 (s, 1H, CH⁺), 6.67 (s, 4H, H₃), 3.23 (s, 12H, N(CH₃)₂), 2.22 (s, 12H, CH₃).

¹³C NMR (100 MHz, CD₃CN) δ 157.8 (CH⁺), 157.4 (C₄), 147.8 (C₂), 130.2 (C₁), 115.2 (C₃), 41.4 (N(CH₃)₂), 21.8 (CH₃).

HRMS (ESI+): m/z: calcd for $C_{21}H_{29}N_2$: 309.2325 $[M-PF_6]^+$; found: 309.2333 $[M-PF_6]^+$.

HRMS (ESI−): m/z: calcd for $F_6P$: 144.9647 $[PF_6]^-$; found: 145.0845 $[PF_6]^-$.

UV-vis-NIR ($CH_3CN$) λmax/nm (ε/L $mol^{-1}$ $cm^{-1}$): 644 (46 507) (as can be seen in FIG. 6).

Crystal data: for $C_{21}H_{29}F_6N_2P$, triclinic, P1, a=11.4808 (6), b=17.1376(10), c=18.2833(11) Å, α=110.738(2), β=92.232(2), γ=98.955(2); V=3305.95, Z=6.

Compound 30-$PF_6^-$:

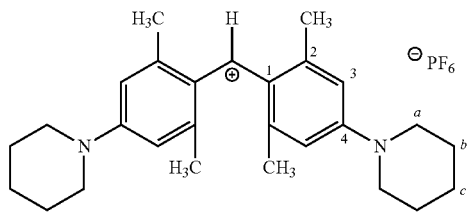 [SMILES: Cc1cc(N2CCCCC2)cc(C)c1[CH+]c1c(C)cc(N2CCCCC2)cc1C ; "PF6"]

Bis(2,6-dimethyl-4-(piperidin-1-yl)phenyl)methylium hexafluorophosphate

The above general procedure for the synthesis of target compounds was applied to bis(2,6-dimethyl-4-(piperidin-1-yl)phenyl)methane (2.60 g, 6.66 mmol). The crude product was washed with EtOAc to give the title compound as greenish iridescent crystalline plates with a bronze luster (2.0 g, 56.2%).

$^1$H NMR (400 MHz, $CDCl_3$) δ 8.26 (s, 1H, $CH^+$), 6.82 (s, 4H, $H_3$), 3.68-3.62 (m, 8H, $H_a$), 2.19 (s, 12H, $CH_3$), 1.76-1.69 (m, 12H, $H_{b,c}$).

$^{13}$C NMR (100 MHz, $CDCl_3$) δ 156.6 ($CH^+$), 156.0 ($C_4$), 147.5 ($C_2$), 131.1 ($C_1$), 116.2 ($C_3$), 50.5 ($C_a$), 27.0 ($C_b$), 24.8 ($C_c$), 21.8 ($CH_3$).

HRMS (ESI+): m/z: calcd for $C_{27}H_{37}N_2$: 389.2951 $[M-PF_6]^+$; found: 389.2948 $[M-PF_6]^+$.

HRMS (ESI−): m/z: calcd for $F_6P$: 144.9647 $[PF_6]^-$; found: 145.0831 $[PF_6]^-$.

UV-vis-NIR ($CH_3CN$) λmax/nm (ε/L $mol^{-1}$ $cm^{-1}$): 655.5 (31 067) (as can be seen in FIG. 6).

Compound 31-$PF_6^-$

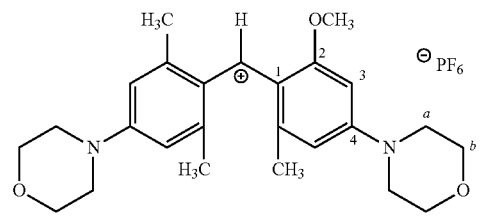 [SMILES: COc1cc(N2CCOCC2)cc(C)c1[CH+]c1c(C)cc(N2CCOCC2)cc1C ; "PF6"]

Bis(2,6-dimethyl-4-morpholinophenyl)methylium hexafluorophosphate

The above general procedure for the synthesis of target compounds was applied to bis(2,6-dimethyl-4-morpholinophenyl)methane (2.35 g, 5.96 mmol). The title compound was purified by discarding remaining impurities loosely soluble in $CH_2Cl_2$ and by washing the resulting crude product with a THF/$Et_2O$ mixture to yield a lustrous solid (1.5 g, 46.7%).

$^1$H NMR (300 MHz, $CD_3CN$) δ 8.35 (s, 1H, $CH^+$), 6.82 (s, 4H, $H_3$), 3.85-3.78 (m, 8H, $H_b$), 3.64-3.59 (m, 8H, $H_a$), 2.21 (s, 12H, $CH_3$).

$^{13}$C NMR (75 MHz, $CDCl_3$) δ 157.6 ($C_4$), 157.1 ($CH^+$), 147.6 ($C_2$), 131.8 ($C_1$), 116.3 ($C_3$), 67.2 ($C_b$), 49.4 ($C_a$), 21.8 ($CH_3$).

HRMS (ESI+): m/z: calcd for $C_{25}H_{33}N_2O_2$: 393.2537 $[M-PF_6]^+$; found: 393.2526 $[M-PF_6]^+$; calcd for $C_{26}H_{37}N_2O_3$: 425.2799 $[M-PF_6+MeOH]^+$; found: 425.2772 $[M-PF_6+MeOH]^+$. HRMS (ESI−): m/z: calcd for $F_6P$: 144.9647 $[PF_6]^-$; found: 145.0865 $[PF_6]^-$.

I-2.iii. Synthesis of Compounds 8 and 11 According to General Procedure Cbis

Synthesis of Julolidine-Type Diarylmethylene Precursors

General procedure: in a two-necked 50 mL round-bottom flask fitted with a reflux condenser, was placed a properly substituted aniline (7.65 mmol) diluted by addition of a 17 mL MeCN/$CH_2Cl_2$/$H_2O$ (12:4:1) mixture. Hydrochloric acid (0.25 mL, 37%) was then added dropwise to this solution, before addition of formalin (0.25 mL, 37% in water), and the resulting mixture was refluxed overnight under argon atmosphere. After completion of the reaction followed by TLC, the mixture was allowed to cool to room temperature and neutralized by slow addition of a 1M aqueous solution of $NaHCO_3$ until pH 8 was reached. The mixture was then poured into 20 mL of distilled water and the resulting aqueous layer extracted three times with chloroform (3×40 mL). The organic layers were then combined, dried over $MgSO_4$ and filtered before removal of the solvent under reduced pressure. The residue was finally purified by flash chromatography to give the target methylene compound that often easily crystallizes.

Compound 8 Precursor

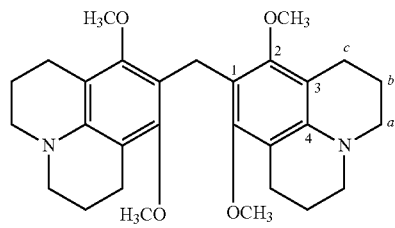 [SMILES: COc1c(Cc2c(OC)c3c4c(c2OC)CCCN4CCC3)c(OC)c2c3c1CCCN3CCC2]

Bis(8,10-dimethoxy-2,3,6,7-tetrahydro-1H, 5H-pyrido[3,2,1-ij]quinolin-9-yl) methane The above general procedure was applied to 8,10-dimethoxyjulolidine [U.S. Pat. No. 4,471,041] (0.50 g, 2.14 mmol). The title compound was purified via the Biotage Isolera One (silica-packed snap cartridge; 40-100% $CH_2Cl_2$/cyclohexane then 0-10% EtOAc/$CH_2Cl_2$) and recrystallized as prismatic colorless crystals from $CH_2Cl_2$/$Et_2O$ (0.23 g, 45%).

$^1$H NMR (300 MHz, $CDCl_3$) δ 3.90 (s, 2H, $CH_2$), 3.49 (s, 12H, $OCH_3$), 3.07 (t, $^3J_{a-b}$=5.7 Hz, 8H, $H_a$), 2.72 (t, $^3J_{c-b}$=6.6 Hz, 8H, $H_c$), 1.96-1.86 (m, 8H, $H_b$).

$^{13}$C NMR (75 MHz, CDCl$_3$) δ 155.5 (C$_2$), 142.1 (C$_4$), 116.5 (C$_1$), 111.2 (C$_3$), 60.1 (OCH$_3$), 50.3 (C$_a$), 22.1 (C$_c$), 21.8 (C$_b$), 19.1 (CH$_2$).

HRMS: m/z: calcd for C$_{29}$H$_{38}$N$_2$NaO$_4$: 501.2724 [M+Na]$^+$; found: 501.2737 [M+Na]$^+$. Crystal data: for C$_{29}$H$_{38}$N$_2$O$_4$, orthorhombic, Pbca, a=17.4380(4), b=9.0985 (2), c=31.4390(8) Å, α=90.000, β=90.000, γ=90.000; V=4988.1, Z=8.

Compound 11 Precursor

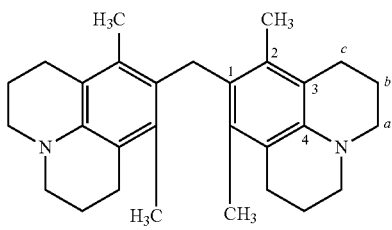 [SMILES: Cc1c(Cc2c(C)c3c4c(c2C)CCCN4CCC3)c(C)c2c3c1CCCN3CCC2]

Bis(8,10-dimethyl-2,3,6,7-tetrahydro-1H,5H-pyrido [3,2,1-ij]quinolin-9-yl)methane The above general procedure was applied to 8,10-dimethyljulolidine [Dance2008] (1.54 g, 7.65 mmol). The title compound was purified via the Biotage Isolera One (silica-packed snap cartridge; 30-100% CH$_2$Cl$_2$/cyclohexane then 0-15% EtOAc/CH$_2$Cl$_2$) (0.54 g, 34%).

$^1$H NMR (400 MHz, CDCl$_3$) δ 4.03 (s, 2H, CH$_2$), 3.02 (t, $^3J_{a-b}$=5.4 Hz, 8H, H$_a$), 2.64 (t, $^3J_{c-b}$=6.8 Hz, 8H, H$_c$), 2.04-1.98 (m, 8H, H$_b$), 1.97 (s, 12H, CH$_3$).

$^{13}$C NMR (100 MHz, CDCl$_3$) δ 142.0 (C$_4$), 133.0 (C$_2$), 129.0 (C$_1$), 119.0 (C$_3$), 50.5 (C$_a$), 32.2 (CH$_2$), 26.2 (C$_c$), 23.1 (C$_b$), 16.2 (CH$_3$).

HRMS: m/z: calcd for C$_{29}$H$_{39}$N$_2$: 415.3108 [M+H]$^+$; found: 415.3115 [M+H]$^+$.

Synthesis of Julolidine-Type Diarylmethylene Target Compounds:

General procedure for the synthesis of target compounds is the same as in the previous section: To a vigorously stirred solution of the proper methylene compound in a minimum amount of THF was dropwise added a solution of oxidant (here more particularly an hydride abstraction reagent) in THF, preferably 2,3-dichloro-5,6-dicyano-1,4-benzoquinone (DDQ) (1.0 equivalent). After stirring for approximately 2.5 h at room temperature, the reaction mixture was concentrated under reduced pressure and then dropwise added (after previous filtration through a pipette plugged with cotton wool) to a saturated solution of the desired counteranion, e.g. potassium hexafluorophosphate (metathesis of DDQH$^-$/PF6$^-$). This suspension was stirred for 20 minutes before filtration of the dark precipitate, which was taken up in CH$_2$Cl$_2$. The resulting deeply (blue-)colored organic layer was washed with a minimum amount of distilled water (until giving a colorless aqueous layer) and concentrated under reduced pressure. The residue was finally purified by slow vapor crystallization. Noticingly, the final metathesis may be avoided to afford the methylium compound associated to a counteranion derived from the reduced form of the oxidant sooner utilized, e.g. DDQH$^-$.

Compound 8-PF$_6^-$

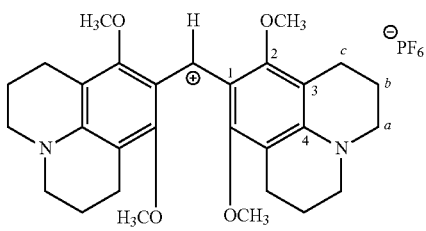 [SMILES: COc1c([CH+]c2c(OC)c3c4c(c2OC)CCCN4CCC3)c(OC)c2c3c1CCCN3CCC2 ; "PF6"]

Bis(8,10-dimethoxy-2,3,6,7-tetrahydro-1H, 5H-pyrido[3,2,1-ij]quinolin-9-yl)methylium hexafluorophosphate The general procedure as above was applied to bis(8,10-dimethoxy-2,3,6,7-tetrahydro-1H,5H-pyrido[3,2,1-ij]quinolin-9-yl)methane (0.23 g, 0.48 mmol) to give pure title compound as a lustrous solid after several recrystallizations (0.045 g, 15%).

$^1$H NMR (300 MHz, CD$_3$CN) δ 8.29 (s, 1H, CH$^+$), 3.69 (s, 12H, OCH$_3$), 3.56-3.49 (m, 8H, H$_a$), 2.81-2.74 (m, 8H, H$_c$), 2.14-2.09 (m, 8H, H$_b$).

Compound 11-PF$_6^-$

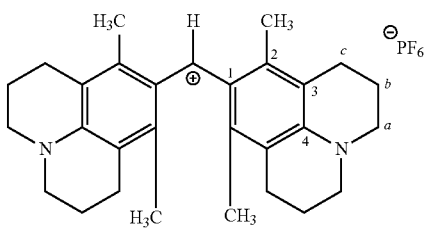 [SMILES: Cc1c([CH+]c2c(C)c3c4c(c2C)CCCN4CCC3)c(C)c2c3c1CCCN3CCC2 ; "PF6"]

Bis(8,10-dimethyl-2,3,6,7-tetrahydro-1H,5H-pyrido [3,2,1-ij]quinolin-9-yl)methylium hexafluorophosphate The general procedure as above was applied to bis(8,10-dimethyl-2,3,6,7-tetrahydro-1H,5H-pyrido[3,2,1-ij]quinolin-9-yl)methane (0.5 g, 1.20 mmol) to give pure title compound as a lustrous solid after several recrystallizations (0.134 g, 20%).

$^1$H NMR (300 MHz, CD$_3$CN) δ 8.26 (s, 1H, CH$^+$), 3.48-3.41 (m, 8H, H$_a$), 2.71-2.63 (m, 8H, H$_c$), 2.04 (s, 12H, CH$_3$), 2.03-1.91 (m, 8H, H$_b$).

HRMS (ESI+): m/z: calcd for C$_{29}$H$_{37}$N$_2$: 413.2951 [M-PF$_6$]$^+$; found: 413.2959 [M-PF$_6$].

HRMS (ESI-): m/z: calcd for F$_6$P: 144.9647 [PF$_6$]$^-$; found: 145.0901 [PF$_6$]$^-$.

I-2.iv. Synthesis of Compounds 32 According to General Procedure M

Synthesis of Diarylcyanomethylene Precursors

General procedure for the synthesis of precursors: To a vigorously stirred solution of the proper methylium compound in a minimum amount of MeCN was portionwise added KCN (or another cyanide salt) (1.0 equivalent). After stirring for approximately 3-4 h at room temperature, the resulting colorless reaction mixture was filtered if appearance of a precipitate and then concentrated under reduced pressure. The residue was taken up in $CH_2Cl_2$ and the organic layer washed with distilled water before concentration under reduced pressure to give the target compound with no need of further purification.

Compound 32 Precursor

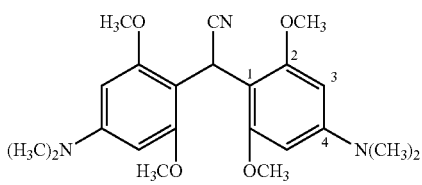

2,2-Bis(4-(dimethylamino)-2,6-dimethoxyphenyl) acetonitrile

The above general procedure was applied to bis(4-(dimethylamino)-2,6-dimethoxyphenyl)methylium hexafluorophosphate (0.279 g, 0.54 mmol) to yield the title compound as colorless microcrystals (0.213 g, 99%).

$^1$H NMR (400 MHz, $CDCl_3$) δ 5.87 (s, 4H, $H_3$), 5.86 (s, 1H, CH), 3.77 (s, 12H, $OCH_3$), 2.93 (s, 12H, $N(CH_3)_2$).

$^{13}$C NMR (100 MHz, $CDCl_3$) δ 159.1 ($C_2$), 151.2 ($C_4$), 121.7 (CN), 103.4 ($C_1$), 90.3 ($C_3$), 56.2 ($OCH_3$), 40.8 ($N(CH_3)_2$), 21.3 (CH).

HRMS: m/z: calcd for $C_{22}H_{29}N_3NaO_4$: 422.2050 $[M+Na]^+$; found: 422.2064 $[M+Na]^+$; calcd for $C_{44}H_{58}N_6NaO_8$: 821.4208 $[2M+Na]^+$; found: 821.4268 $[2M+Na]^+$.

Synthesis of Diarylcyanomethyliums Target Compounds

General procedure for the synthesis of target diarylcyanomethyliums: To a vigorously stirred solution of the proper cyanomethylene compound in a minimum amount of THF was dropwise added a solution of oxidant (here more particularly an hydride abstraction reagent) in THF, preferably 2,3-dichloro-5,6-dicyano-1,4-benzoquinone (DDQ) (1.0 equivalent). After stirring for approximately 2.5 h at room temperature, the reaction mixture was concentrated under reduced pressure and then dropwise added (after previous filtration through a pipette plugged with cotton wool) to a saturated solution of the desired counteranion, e.g. potassium hexafluorophosphate (metathesis of $DDQH^-$/$PF_6^-$). This suspension was stirred for 20 minutes before filtration of the dark precipitate, which was taken up in $CH_2Cl_2$. The resulting deeply (green-)colored organic layer was washed with a minimum amount of distilled water (until giving a colorless aqueous layer) and concentrated under reduced pressure. The residue can finally be further purified by slow vapor crystallization. Noticingly, the final metathesis may be avoided to afford the methylium compound associated to a counteranion derived from the reduced form of the oxidant sooner utilized, e.g. $DDQH^-$.

Compound 32-$DDQH^-$

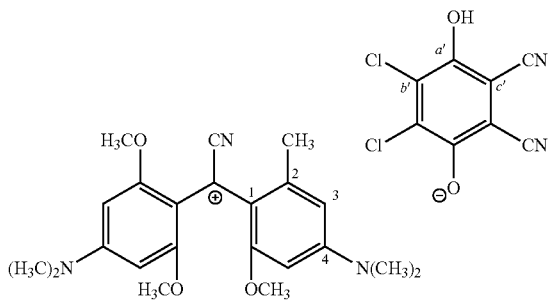

Cyanobis(4-(dimethylamino)-2,6-dimethoxyphenyl) methylium 2,3-dichloro-5,6-dicyano-4-hydroxyphenolate The above general procedure for the synthesis of target diarylcyanomethyliums was applied to 2,2-bis(4-(dimethylamino)-2,6-dimethoxyphenyl)-acetonitrile (0.2 g, 0.50 mmol) to yield the title compound that was simply filtered from the reaction mixture to give a reddish brown solid (affording a green solution) that appears under microscope as shiny tiny crystals with a gold-like metallic luster (0.220 g, 70.3%).

$^1$H NMR (300 MHz, DMSO-$d_6$) δ 6.06 (s, 4H, $H_3$), 3.80 (s, 12H, $OCH_3$), 3.37 (s, 12H, $N(CH_3)_2$).

$^{13}$C NMR (75 MHz, DMSO-$d_6$) δ 161.5 ($C_2$), 157.9 ($C_4$), 118.4 ($CN_{DDQH}$), 117.0 ($CN_{DDQH}$), 115.7 ($C_1$), 90.4 ($C_3$), 56.6 ($OCH_3$), 41.4 ($N(CH_3)_2$).

HRMS (ESI+): m/z: calcd for $C_{22}H_{28}N_3O_4$: 398.2074 $[M-DDQH]^+$; found: 398.2088 $[M-DDQH]^+$.

HRMS (ESI-): m/z: calcd for $C_8HCl_2N_2O_2$: 226.9421 $[DDQH]^-$; found: 226.0912 $[DDQH]^-$.

Compound 32-$PF_6^-$

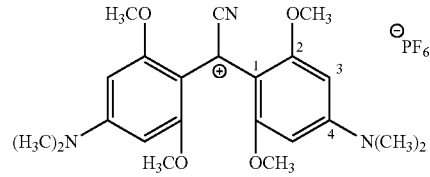

Cyanobis(4-(dimethylamino)-2,6-dimethoxyphenyl) methylium hexafluorophosphate

A small quantity of the previously described cyanobis(4-(dimethylamino)-2,6-dimethoxyphenyl)methylium 2,3-dichloro-5,6-dicyano-4-hydroxyphenolate (50 mg, 0.08 mmol) was engaged in a metathesis step using potassium hexafluorophosphate. The crude product was washed with chloroform to give the title compound as iridescent crystalline plates with a copper-like metallic luster (30 mg, 69%).

$^1$H NMR (300 MHz, $CD_3CN$) δ 5.94 (s, 4H, $H_3$), 3.79 (s, 12H, $OCH_3$), 3.29 (s, 12H, $N(CH_3)_2$).

$^{13}$C NMR (75 MHz, CD$_3$CN) δ 163.3 (C$_2$), 159.9 (C$_4$), 117.4 (C$_1$), 91.1 (C$_3$), 57.1 (OCH$_3$), 42.0 (N(CH$_3$)$_2$).

HRMS (ESI+): m/z: calcd for C$_{22}$H$_{28}$N$_3$O$_4$: 398.2074 [M-PF$_6$]$^+$; found: 398.2085 [M-PF$_6$]$^+$.

HRMS (ESI−): m/z: cal cd for F$_6$P: 144.9647 [PF$_6$]$^-$. found: 145.0862 [PF$_6$]$^-$.

UV-vis-NIR (CH$_3$CN) λmax/nm (ε/L mol$^{-1}$ cm$^{-1}$): 704.5 (33 444) (as can be seen in FIG. 6).

References reporting the preparation and characterization of some starting materials used in the above described general procedures:

[Lee2009]: Lee, B. K., Biscoe, M. R., Buchwald, S. L. *Tetrahedron Lett.*, 2009, 50, 3672-3674.

[DellaPelle2014]: Della Pelle, A. M., Homnick, P. J., Bae, Y., Lahti, P. M., Thayumanavan, S. *J. Phys. Chem. C*, 2014, 118, 1793-1799.

[Yang1999]: Yang, S.-C., Hung, C.-W. *Synthesis*, 1999, 10, 1747-1752.

[Lü2011] Lü, B., Li, P., Fu, C., Xue, L., Lin, Z., Ma, S. *Adv. Synth. Catal.*, 2011, 353, 100-112.

[Hatakeyama2010]: Hatakeyama, T., Yoshimoto, Y., Ghorai, S. K., Nakamura, M. *Org. Lett.*, 2010, 12, 1516-1519.

[Wolfe2000]: Wolfe, J. P., Tomori, H., Sadighi, J. P., Jin, J., Buchwald, S. L. *J. Org. Chem.*, 2000, 65, 1158-1174.

[Saitoh2004] Saitoh, T., Yoshida, S., Ichikawa, *J. Org. Lett.*, 2004, 6, 4563-4565. [U.S. Pat. No. 4,471,041]

[Dance2008]: Dance, Z. E. X., Ahrens, M. J., Vega, A. M., Ricks, A. B., McCamant, D. W., Ratner, M. A., Wasielewski, M. R. *J. Am. Chem. Soc.* 2008, 130, 830-832.

II—Optical Properties of the Compounds According to the Invention

II-1. Absorption Properties

Measurement of the molar extinction coefficients of compounds 1-PF$_6$$^-$, 2-PF$_6$$^-$, 27-PF$_6$$^-$, 28-PF$_6$$^-$, 29-PF$_6$$^-$, 30-PF$_6$$^-$ and 32-PF$_6$$^-$ was carried as follows: for each compound, three independent 10$^{-5}$ mol·L$^{-1}$ acetonitrile solutions (200 mL) were prepared, and absorbances were measured in a 1 cm optical path quartz cuvettes (against reference 1 cm optical path quartz cuvette containing pure acetonitrile) in a double-beam Cary 500 spectrophotometer (Varian).

As it appears on FIGS. 1 and 6, the compounds according to the invention are characterized by a single sharp absorption band in the visible region of the electromagnetic spectrum, and a high molar extinction coefficient. Appropriate chemical modulations allow the absorption bands of the compounds according to the invention to span over an extended region of the visible electromagnetic spectrum (hence allowing display of numerous metal-like effects).

Accordingly, chromophoric properties of compounds of the invention are directly observed from these solutions. For example, an intense deep blue color is observed for 1-PF$_6$$^-$, 27-PF$_6$$^-$ and 28-PF$_6$$^-$ dissolved in acetonitrile, whereas an intense deep green color is observed for 32-PF$_6$$^-$ dissolved in the same solvent (not shown).

II-2. Other Optical Properties

FIG. 3 represents a photograph of the gold-like reflective mirror formed on the wall of a round-bottom flask after simple evaporation of a concentrated solution of 1-PF$_6$$^-$ in acetonitrile, hence showing the propensity of the molecule to self-assemble to yield a well-shaped coating that displays optical properties of interest (e.g. obtaining of a reflective metal-like luster).

FIG. 4*a* represents a photograph (macroscopic view) of typical microcrystalline sample of 1-PF$_6$$^-$, showing a golden-like glittering/sparkling behavior to the naked eye.

FIGS. 4*b* and 4*c* represent micrographs of typical single crystals of compound 1-PF$_6$$^-$, taken under non-polarized light. FIG. 4*b* shows the hexagonal shape of gold-like reflective single crystals.

FIG. 5 represents a micrograph of typical polycrystalline aggregates of greenish-blue chromophore 2-PF$_6$$^-$ exhibiting the iridescent behavior of the crystals observed to the naked eye (under non-polarized light).

FIGS. 7*a* and 7*b* are micrographs of typical greenish iridescent crystalline plates of compound 27-DDQH$^-$ exhibiting the bronze luster of the crystals observed to the naked eye (under non-polarized light).

FIGS. 8*a* and 8*b* are micrographs of typical greenish iridescent crystalline plates of compound 27-PF$_6$$^-$ exhibiting the bronze luster of the crystals observed to the naked eye (under non-polarized light).

FIGS. 9*a* and 9*b* are micrographs of typical large columnar crystals of compound 28-PF$_6$$^-$, taken under non-polarized light. FIG. 9*b* shows the hexagonal shape of green reflective single crystals.

FIGS. 10*a* and 10*b* are micrographs showing typical tiny crystals of compound 29-DDQH$^-$ showing a golden-like glittering/sparkling behavior to the naked eye (under non-polarized light).

FIGS. 11*a* and 11*b* are micrographs of typical large crystalline plates of compound 29-PF$_6$$^-$ exhibiting the gold luster of the crystals observed to the naked eye (under non-polarized light). FIGS. 12*a* and 12*b* are micrographs of typical greenish iridescent crystalline plates of compound 30-PF$_6$$^-$ exhibiting the bronze luster of the crystals observed to the naked eye (under non-polarized light).

FIGS. 13*a* and 13*b* are micrographs showing typical tiny crystals of compound 32-DDQH$^-$ displaying a golden-like glittering/sparkling behavior to the naked eye (under non-polarized light).

FIGS. 14*a* and 14*b* are micrographs of typical iridescent crystalline plates of compound 32-PF$_6$$^-$ exhibiting the copper luster of the crystals observed to the naked eye (under non-polarized light).

Elaboration and characterization of films made of compounds of the invention: spin coating and quantitative reflectance measurements The compounds according to the invention are soluble in most organic polar solvents. For example, an acetonitrile (CH$_3$CN) solution of a compound of the invention (for example at a concentration of 1 mg/mL) can be prepared.

This solution is spin-coated onto a substrate, and after solvent evaporation under ambient conditions, a uniform film exhibiting a reflective appearance is obtained.

Films of different thicknesses can be spin-coated by varying the spin-coating speed or acceleration or duration, or by varying the volume of the solution that is deposited onto the substrate. Also, several layers of films can be superimposed by repeating successive steps of spin coating as above.

Doctor blade technique may also represent an alternative and efficient mode of preparation of films made of compounds of the invention.

The invention claimed is:

1. A metallic effect purely organic pigment material, comprising a self-assembly of a compound of following general formula (I):

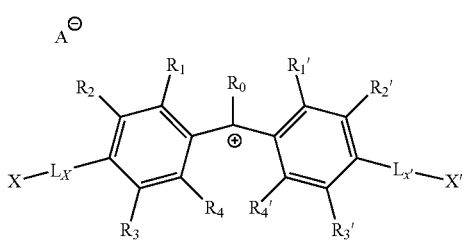

wherein:
$R_0$ represents a hydrogen atom;
$R_1=R_4=R_1'=R_4'$, and $R_1$ represents a $(C_1-C_6)$alkyl, $(C_1-C_6)$haloalkyl, phenyl, cycloalkyl comprising from 3 to 7 carbon atoms, $(CH_2)_m OR_{24}$, or $OR_{26}$, wherein m is equal to 1, 2 or 3;
or
$R_4$ and $R_4'$ form together a bond or a chain selected from the group consisting of $-C(R_{74}R_{75})-$, $-(CH_2)_n-$, wherein:
n is equal to 2 or 3,
$R_{74}$, $R_{75}$ each represent, independently of each other, a hydrogen atom or a $(C_1-C_6)$alkyl;
$R_2=R_2'$, $R_3=R_3'$, and $R_2$ and $R_3$ each represents, a hydrogen atom;
$L_X=L_{X'}$, and $L_X$ represents a bond, or a group selected from the group consisting of:

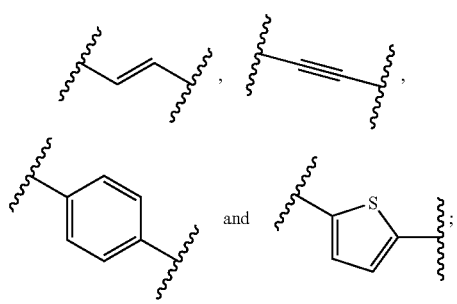

$X=X'$, and X represents $NR_{50}R_{51}$ heterocycle, heteroaryl or aryl, wherein:
said heterocycle and heteroaryl group comprise at least one heteroatom bearing a lone pair of electrons conjugated with $C^+$, and are optionally substituted by one or more groups selected from a halogen atom, $(C_1-C_6)$alkyl, $(C_1-C_6)$haloalkyl, $OR_{56}$, $SR_{57}$ and $NR_{58}R_{59}$, and
said aryl is para-substituted by a group selected from $NR_{60}R_{61}$, and optionally substituted by one or more groups selected from a halogen atom, $(C_1-C_6)$alkyl, $(C_1-C_6)$haloalkyl, $OR_{66}$, $SR_{67}$ and $NR_{68}R_{69}$;
or
$L_X=L_{X'}$ and $L_X$ represents a bond; $X=X'$ and X represents $NR_{50}'R_{51}'$; and
$R_2$ and $NR_{50}'$, and $R_2'$ and $NR_{50}'$ form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$;
and
$R_3$ and $NR_{51}'$, and $R_3'$ and $NR_{51}'$ form together with the carbon atoms that carry them a heterocycle or heteroaryl group, said group being optionally substituted by one or more groups selected from a halogen atom, $(C_1-C_6)$alkyl, $(C_1-C_6)$haloalkyl, $OR_{81}$, $SR_{82}$ and $NR_{83}R_{84}$;
and $R_{50}'$, $R_{51}'$, $R_{52}'$ and $R_{53}'$ represent respectively $R_{50}$, $R_{51}$, $R_{52}$ and $R_{53}$ when they are not linked with $R_2$ or $R_3$;
and
$R_{24}$, $R_{26}$, $R_{50}$, $R_{51}$, $R_{56}$ to $R_{59}$, $R_{66}$ to $R_{69}$ and $R_{81}$ to $R_{84}$ each represents, independently of each other, a hydrogen atom, a $(C_1-C_6)$alkyl, $(C_1-C_6)$haloalkyl or aryl, said group being optionally substituted by one or more groups selected from a halogen atom, a $(C_1-C_6)$alkyl, $(C_1-C_6)$haloalkyl, $OR_{85}$, $SR_{86}$ and $NR_{87}R_{88}$ group, wherein $R_{85}$ to $R_{88}$ each represent, independently of each other, a hydrogen atom or a $(C_1-C_6)$alkyl group;
and
$A^-$ represents a monovalent or multivalent, organic or inorganic anion.

2. The metallic effect purely organic pigment material according to claim 1, wherein said compound is selected from the group consisting of:

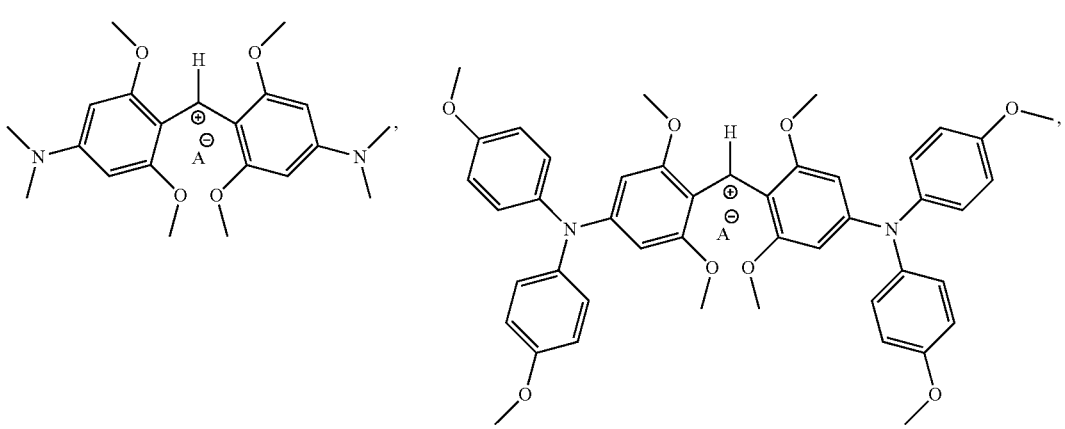

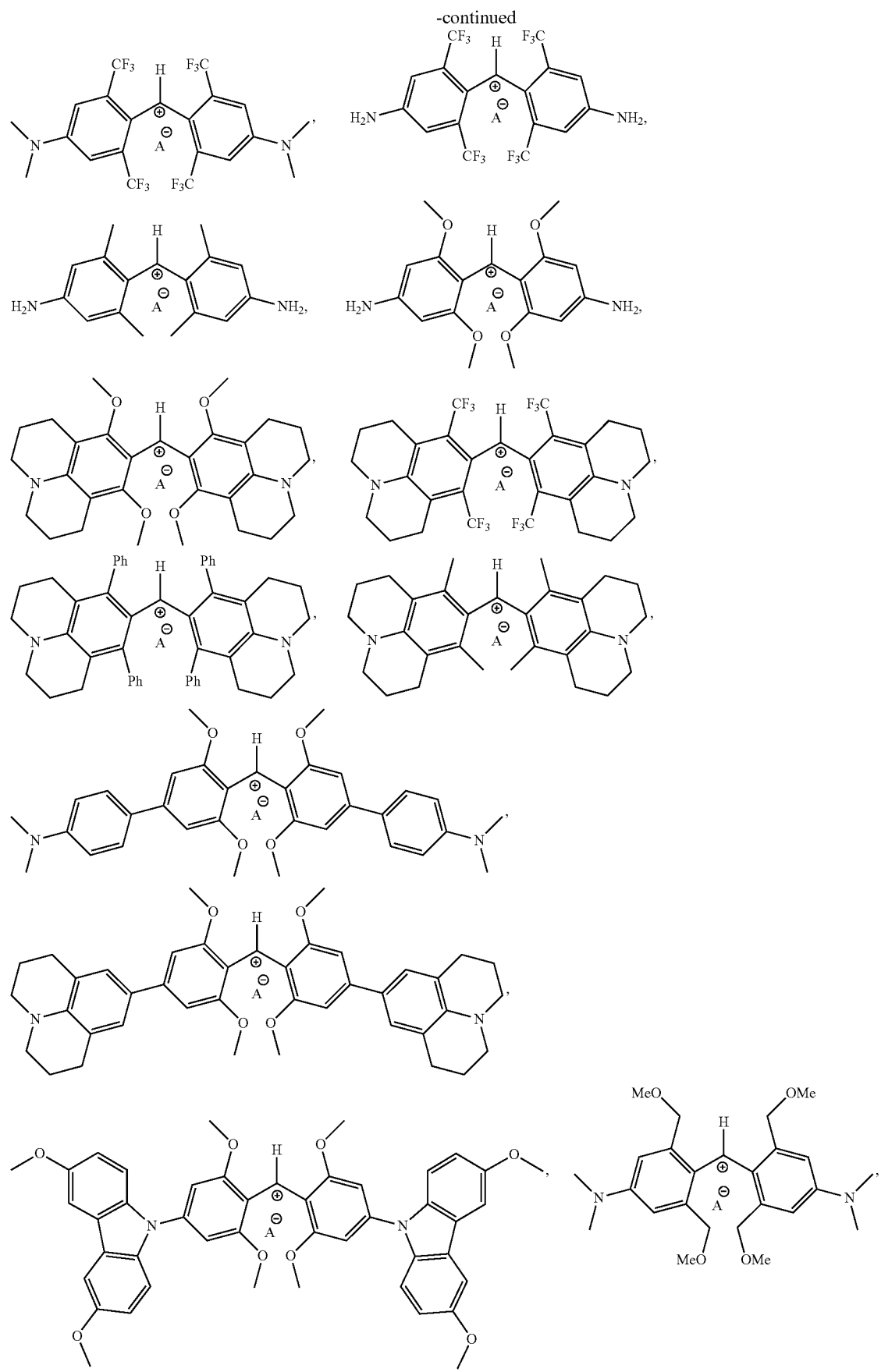

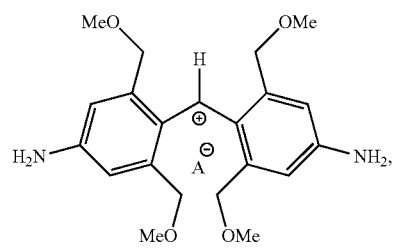
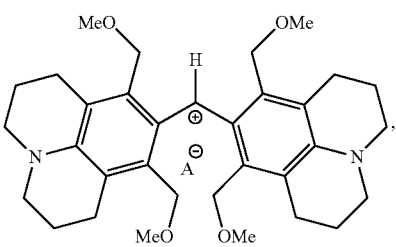
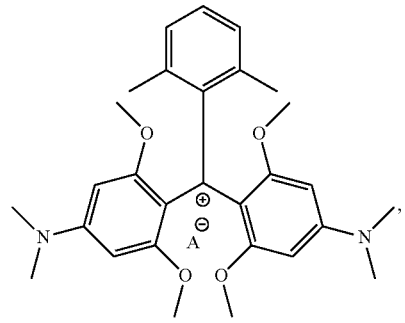
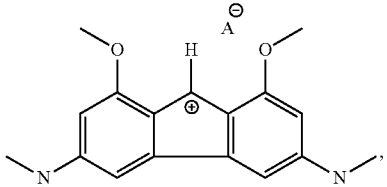
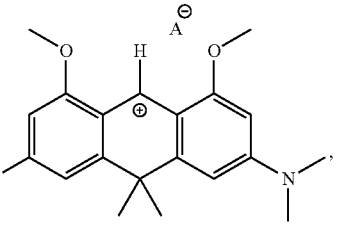
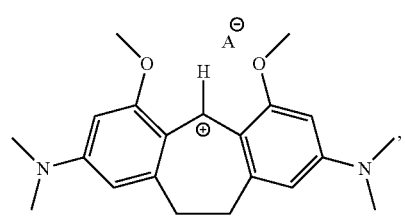
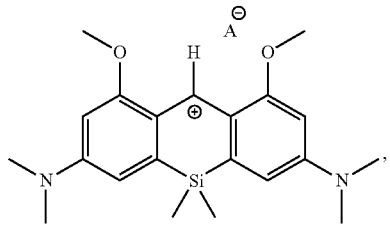
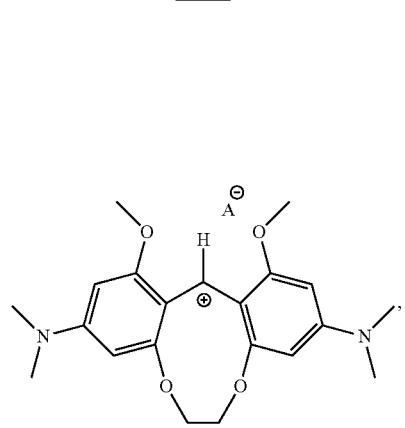
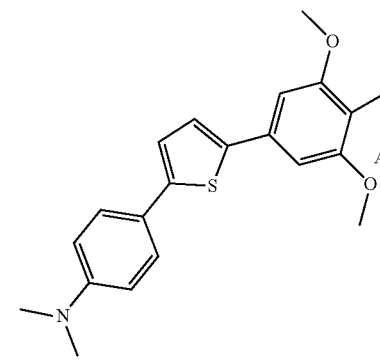
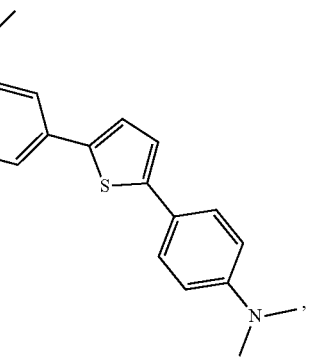
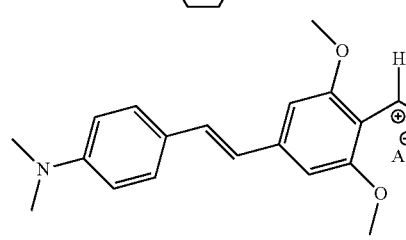
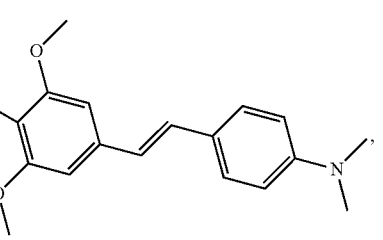
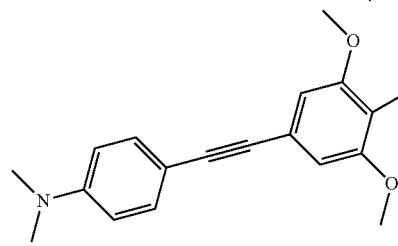
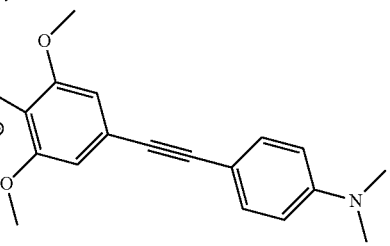

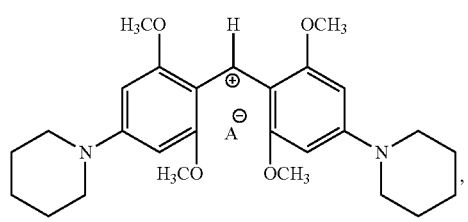

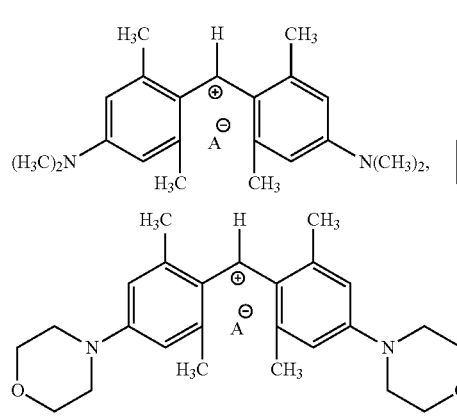
and

-continued

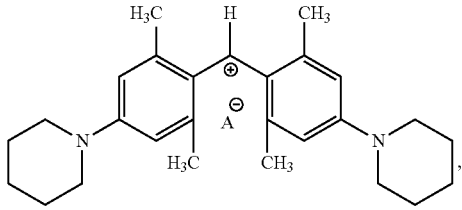

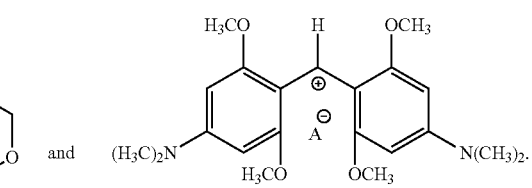

3. The metallic effect purely organic pigment material according to claim 1, wherein said compound is a compound of formula (I) wherein:

$L_X=L_{X'}$, and $L_X$ represents a bond.

4. The metallic effect purely organic pigment material according to claim 1, wherein $A^-$ represents a hexafluorophosphate, tetrafluoroborate, tetraphenylborate, DDQH$^-$, halide or triflate anion.

5. The metallic effect purely organic pigment material according to claim 1, wherein said metallic effect purely organic pigment material is a pigment.

6. The metallic effect purely organic pigment material according to claim 1, wherein said metallic effect purely organic pigment material is a metal-like reflective coating.

7. The metallic effect purely organic pigment material according to claim 1, wherein $R_1$ represents a $(C_1-C_6)$alkyl, $(C_1-C_6)$haloalkyl, phenyl, $CH_2OR_{24}$, or $OR_{26}$.

* * * * *